US010604523B2

(12) United States Patent
Andrés-Gil et al.

(10) Patent No.: US 10,604,523 B2
(45) Date of Patent: Mar. 31, 2020

(54) 1-ARYL-4-METHYL-[1,2,4]TRIAZOLO [4,3-A]QUINOXALINE DERIVATIVES

(75) Inventors: José Ignacio Andrés-Gil, Toledo (ES); Peter Jacobus Johannes Antonius Buijnsters, Beerse (BE); Andrés Avelino Trabanco-Suárez, Toledo (ES); Meri De Angelis, Munich (DE); Greta Constantia Peter Vanhoof, Beerse (BE); Jérôme Emile Georges Guillemont, Val de Reuil (FR); Frederik Jan Rita Rombouts, Beerse (BE); Maarten Vliegen, Beerse (BE); Guy Maurits R. Bormans, Leuven (BE); Sofie Jeanne Leopoldine Celen, Leuven (BE)

(73) Assignee: Janssen Pharmaceutica NV, Beerse (BE)

( * ) Notice: Subject to any disclaimer, the term of this patent is extended or adjusted under 35 U.S.C. 154(b) by 304 days.

(21) Appl. No.: 14/128,835

(22) PCT Filed: Jun. 26, 2012

(86) PCT No.: PCT/EP2012/062381
§ 371 (c)(1),
(2), (4) Date: Dec. 23, 2013

(87) PCT Pub. No.: WO2013/000924
PCT Pub. Date: Jan. 3, 2013

(65) Prior Publication Data

US 2014/0147386 A1 May 29, 2014

(30) Foreign Application Priority Data

Jun. 27, 2011 (EP) .................................... 11171519

(51) Int. Cl.

| | |
|---|---|
| ***A61K 51/00*** | (2006.01) |
| ***A61M 36/14*** | (2006.01) |
| ***C07D 487/04*** | (2006.01) |
| ***A61K 31/4985*** | (2006.01) |
| ***A61K 45/06*** | (2006.01) |
| ***A61K 51/04*** | (2006.01) |
| ***G01N 33/60*** | (2006.01) |

(52) U.S. Cl.
CPC ........ *C07D 487/04* (2013.01); *A61K 31/4985* (2013.01); *A61K 45/06* (2013.01); *A61K 51/0463* (2013.01); *G01N 33/60* (2013.01)

(58) Field of Classification Search
CPC .. C07D 487/04; A61K 31/4985; A61K 45/06; A61K 51/0463; G01N 33/60
USPC ........................................................ 424/1.89
See application file for complete search history.

(56) References Cited

U.S. PATENT DOCUMENTS

| | | | |
|---|---|---|---|
| 4,242,513 | A | 12/1980 | Hoover et al. |
| 4,713,381 | A | 12/1987 | Ao et al. |
| 5,137,876 | A | 8/1992 | MacCoss et al. |
| 5,317,019 | A | 5/1994 | Bender et al. |
| 5,360,796 | A | 11/1994 | Hansen et al. |
| 5,486,525 | A | 1/1996 | Summers et al. |
| 5,498,774 | A | 3/1996 | Mitsudera et al. |
| 5,559,106 | A | 9/1996 | Jacobsen et al. |
| 5,683,998 | A | 11/1997 | Shibayama et al. |
| 6,054,587 | A | 4/2000 | Reddy et al. |
| 6,245,769 | B1 | 6/2001 | Arvanitis et al. |
| 6,248,755 | B1 | 6/2001 | Chapman et al. |
| 6,352,990 | B1 | 3/2002 | McCarthy et al. |
| 6,403,588 | B1 | 6/2002 | Hayakawa et al. |
| 6,589,947 | B1 | 7/2003 | Hamanaka et al. |
| 6,777,395 | B2 | 8/2004 | Bhat et al. |

(Continued)

FOREIGN PATENT DOCUMENTS

| | | | |
|---|---|---|---|
| CA | 2398956 | A1 | 8/2001 |
| CA | 2668738 | A1 | 7/2008 |

(Continued)

OTHER PUBLICATIONS

Vyas et al. Ind. J. Het. Chem. 2005, 361-362.*
Netscher et al. Eur. J. Org. Chem. 2007, 1176-1183.*
Lasne et al. Top. Curr. Chem. 2002, 202-258.*
Kingsbury et al. J. Med. Chem. 1991, 98-107.*
International Search Report for PCT/EP2012/062381 dated Sep. 19, 2012.
Aggarwal R et al_European Journal of Medicinal Chemistry, Editions Scientific Elsevier, Paris, FR, 46(12), 6083-6088, (2011).
Andres J et al., Bioorganic & Medicinal Chemistry Letters,785-790, 2013.
Belanger, et al. "Discovery of imidazo[1,2-a]pyrazine-based Aurora kinase inhibitors", Bioorganic & Medicinal Chemistry Letters (2010), 20(17), 5170-5174.
Belanger, et al. "Discovery of orally bioavailable imidazo[1,2-a]pyrazine-based Aurora kinase inhibitors", Bioorganic & Medicinal Chemistry Letters (2010), 20(22), 6739-6743.

(Continued)

*Primary Examiner* — Michael G Hartley
*Assistant Examiner* — Sean R Donohue

(57) ABSTRACT

The present invention relates to novel 1-aryl-4-methyl-[1,2,4]triazolo[4,3-a]-quinoxaline derivatives as inhibitors of phosphodiesterase 2 (PDE2) and to a lesser extent of phosphodiesterase 10 (PDE10) or as inhibitors of both, phosphodiesterases 2 and 10. The invention is also directed to pharmaceutical compositions comprising such compounds, to processes for preparing such compounds and compositions, and to the use of such compounds and compositions for the prevention and treatment of disorders in which PDE2 is involved, or disorders in which both PDE2 and PDE10 are involved, such as neurological and psychiatric disorders, and endocrinological or metabolic diseases. The present invention also relates to radiolabelled compounds which may be useful for imaging and quantifying the PDE2 enzyme in tissues, using positron-emission tomography (PET). The invention is also directed to compositions comprising such compounds, to processes for preparing such compounds and compositions, to the use of such compounds and compositions for imaging a tissue, cells or a host, in vitro or in vivo and to precursors of said compounds.

2 Claims, No Drawings

(56) References Cited

U.S. PATENT DOCUMENTS

| | | | | |
|---|---|---|---|---|
| 6,806,268 | B2 | 10/2004 | Gall et al. | |
| 6,844,341 | B2 | 1/2005 | Thomas et al. | |
| 6,855,719 | B1 | 2/2005 | Thomas et al. | |
| 6,900,217 | B2 | 5/2005 | Chen et al. | |
| 6,936,617 | B2 | 8/2005 | Hutchison et al. | |
| 6,992,080 | B2 | 1/2006 | Dwyer et al. | |
| 6,992,188 | B1 | 1/2006 | Chen et al. | |
| 7,074,801 | B1 | 7/2006 | Yoshida et al. | |
| 7,078,405 | B2 | 7/2006 | Hibi et al. | |
| 7,078,410 | B2 | 7/2006 | Berg et al. | |
| 7,105,533 | B2 | 9/2006 | Campbell et al. | |
| 7,132,426 | B2 | 11/2006 | Jones et al. | |
| 7,148,353 | B2 | 12/2006 | Fang et al. | |
| 7,186,714 | B2 | 3/2007 | Gudmundsson et al. | |
| 7,186,740 | B2 | 3/2007 | Paruch et al. | |
| 7,186,832 | B2 | 3/2007 | Sun et al. | |
| 7,189,723 | B2 | 3/2007 | Mitchell et al. | |
| 7,196,095 | B2 | 3/2007 | Biftu et al. | |
| 7,244,740 | B2 | 7/2007 | Gudmundsson et al. | |
| 7,259,164 | B2 | 8/2007 | Mitchell et al. | |
| 7,306,631 | B2 | 12/2007 | Glenn et al. | |
| 7,312,341 | B2 | 12/2007 | DeSimone et al. | |
| 7,320,995 | B2 | 1/2008 | Bonjouklian et al. | |
| 7,348,359 | B2 | 3/2008 | Gardinier et al. | |
| 7,393,848 | B2 | 7/2008 | Currie et al. | |
| 7,405,295 | B2 | 7/2008 | Currie et al. | |
| 7,417,041 | B2 | 8/2008 | Blumberg et al. | |
| 7,491,716 | B2 | 2/2009 | Engler et al. | |
| 7,504,404 | B2 | 3/2009 | McArthur et al. | |
| 7,511,040 | B2 | 3/2009 | Belanger et al. | |
| 7,557,103 | B2 | 7/2009 | Collins et al. | |
| 7,563,797 | B2 | 7/2009 | Araldi et al. | |
| 7,572,807 | B2 | 8/2009 | Li et al. | |
| 7,576,085 | B2 | 8/2009 | Guzi et al. | |
| 7,622,584 | B2 | 11/2009 | Kim et al. | |
| 7,666,880 | B2 | 2/2010 | Lee et al. | |
| 7,674,801 | B2 | 3/2010 | Basarab et al. | |
| 8,716,282 | B2 | 5/2014 | Pastor-Fernandez et al. | |
| 8,859,543 | B2 | 10/2014 | Bartolome-Nebreda et al. | |
| 2001/0041673 | A1 | 11/2001 | Fossa | |
| 2002/0049208 | A1 | 4/2002 | Bakthavatchalam et al. | |
| 2003/0027820 | A1 | 2/2003 | Gall et al. | |
| 2004/0014957 | A1 | 1/2004 | Eldrup et al. | |
| 2004/0058938 | A1 | 3/2004 | Cullmann et al. | |
| 2004/0204347 | A1 | 10/2004 | Turski et al. | |
| 2005/0031588 | A1 | 2/2005 | Sommadossi et al. | |
| 2005/0079176 | A1 | 4/2005 | Pierson et al. | |
| 2005/0079387 | A1 | 4/2005 | Lee et al. | |
| 2005/0165232 | A1 | 7/2005 | Beresis et al. | |
| 2005/0234029 | A1 | 10/2005 | Dodic et al. | |
| 2005/0245520 | A1 | 11/2005 | Dodic et al. | |
| 2005/0288295 | A1 | 12/2005 | Currie et al. | |
| 2006/0094699 | A1 | 5/2006 | Kampen et al. | |
| 2006/0100235 | A1 | 5/2006 | Andersen et al. | |
| 2006/0135517 | A1 | 6/2006 | Lee et al. | |
| 2006/0154105 | A1 | 7/2006 | Yamamoto et al. | |
| 2006/0178367 | A1 | 8/2006 | Currie et al. | |
| 2006/0258722 | A1 | 11/2006 | Yasuma et al. | |
| 2007/0004736 | A1 | 1/2007 | Kubo et al. | |
| 2007/0049591 | A1 | 3/2007 | Pinkerton et al. | |
| 2007/0078136 | A1 | 4/2007 | Vaccaro et al. | |
| 2007/0099925 | A1 | 5/2007 | Calderwood et al. | |
| 2007/0105864 | A1 | 5/2007 | Guzi et al. | |
| 2007/0117804 | A1 | 5/2007 | Zhao et al. | |
| 2007/0149535 | A1 | 6/2007 | Berset et al. | |
| 2007/0185063 | A1 | 8/2007 | Storer et al. | |
| 2007/0197507 | A1 | 8/2007 | Morgan et al. | |
| 2007/0219205 | A1 | 9/2007 | Brenchley et al. | |
| 2008/0021217 | A1 | 1/2008 | Borchardt et al. | |
| 2008/0045536 | A1 | 2/2008 | Vaccaro et al. | |
| 2008/0070894 | A1 | 3/2008 | Kawamura et al. | |
| 2008/0102028 | A1 | 5/2008 | Morel et al. | |
| 2008/0103136 | A1 | 5/2008 | Sato et al. | |
| 2008/0113978 | A1 | 5/2008 | Barbosa et al. | |
| 2008/0161341 | A1 | 7/2008 | Calderwood et al. | |
| 2008/0167314 | A1 | 7/2008 | Uchikawa et al. | |
| 2008/0207634 | A1 | 8/2008 | Gudmundsson et al. | |
| 2008/0221092 | A1 | 9/2008 | Bluhm et al. | |
| 2008/0242862 | A1 | 10/2008 | Calderwood et al. | |
| 2008/0255358 | A1 | 10/2008 | Bamford et al. | |
| 2008/0300242 | A1 | 12/2008 | Kuntz et al. | |
| 2008/0305081 | A1 | 12/2008 | Hashihayata et al. | |
| 2008/0318975 | A1 | 12/2008 | Wagner et al. | |
| 2009/0005374 | A1 | 1/2009 | Melvin et al. | |
| 2009/0023737 | A1 | 1/2009 | Xu et al. | |
| 2009/0054409 | A1 | 2/2009 | Andrews et al. | |
| 2009/0124625 | A1 | 5/2009 | Bessis et al. | |
| 2009/0143367 | A1* | 6/2009 | Malamas et al. | 514/221 |
| 2009/0143376 | A1 | 6/2009 | Milburn et al. | |
| 2009/0153035 | A1 | 6/2009 | Shin et al. | |
| 2009/0156604 | A1 | 6/2009 | Holder et al. | |
| 2009/0175852 | A1 | 7/2009 | Ciavarri et al. | |
| 2009/0176778 | A1 | 7/2009 | Schmitz et al. | |
| 2009/0203732 | A1 | 8/2009 | Dhanak et al. | |
| 2009/0209573 | A1 | 8/2009 | Wu et al. | |
| 2009/0215818 | A1 | 8/2009 | Adams et al. | |
| 2009/0270436 | A1 | 10/2009 | Iino et al. | |
| 2009/0317361 | A1 | 12/2009 | Cho et al. | |
| 2009/0325953 | A1 | 12/2009 | Sahoo et al. | |
| 2010/0029633 | A1 | 2/2010 | Allen et al. | |
| 2010/0029638 | A1 | 2/2010 | Melvin et al. | |
| 2010/0063068 | A1 | 3/2010 | Pracitto et al. | |
| 2010/0160280 | A1* | 6/2010 | Allen et al. | 514/210.2 |
| 2012/0302564 | A1* | 11/2012 | Lankau et al. | 514/233.2 |

FOREIGN PATENT DOCUMENTS

| | | | |
|---|---|---|---|
| CL | 3212-2007 | | 6/2008 |
| CN | 1066849 | | 12/1992 |
| CN | 1122601 | | 5/1996 |
| EP | 0728759 | | 8/1996 |
| EP | 1 293 213 | A1 | 3/2003 |
| IT | 1374954 | B1 | 5/2010 |
| JP | 6247969 | A | 9/1994 |
| JP | 2001-006877 | | 1/2001 |
| JP | 2001-057292 | A | 2/2001 |
| JP | 2003-313126 | A | 11/2003 |
| JP | 2004-002826 | A | 1/2004 |
| JP | 2005-343889 | A | 12/2005 |
| WO | WO 90/15534 | A1 | 12/1990 |
| WO | WO 91/19497 | A1 | 12/1991 |
| WO | WO 92/10190 | A1 | 6/1992 |
| WO | WO 92/10498 | A1 | 6/1992 |
| WO | WO 96/34866 | A1 | 11/1996 |
| WO | WO 02/34748 | A1 | 5/2002 |
| WO | WO 02/066478 | A1 | 8/2002 |
| WO | WO 2004/017950 | A2 | 3/2004 |
| WO | WO 2004/026877 | A1 | 4/2004 |
| WO | WO 2004/035579 | A1 | 4/2004 |
| WO | WO 2004/075846 | A2 | 9/2004 |
| WO | WO 2004/087710 | A1 | 10/2004 |
| WO | WO 2004/089416 | A2 | 10/2004 |
| WO | WO 2004/103991 | A1 | 12/2004 |
| WO | WO 2005/014599 | A1 | 2/2005 |
| WO | WO 2005/020885 | A2 | 3/2005 |
| WO | WO 2005/047290 | A2 | 5/2005 |
| WO | WO 2006/044509 | A2 | 4/2006 |
| WO | WO 2006/102194 | | 9/2006 |
| WO | WO 2007/003386 | A1 | 1/2007 |
| WO | WO 2007/013673 | A1 | 2/2007 |
| WO | WO 2007/048779 | A1 | 5/2007 |
| WO | WO 2007/087548 | A2 | 8/2007 |
| WO | WO 2007/145921 | A1 | 12/2007 |
| WO | WO 2008/003511 | A1 | 1/2008 |
| WO | WO 2008/030579 | A2 | 3/2008 |
| WO | WO 2008/030795 | A2 | 3/2008 |
| WO | WO 2008/057402 | A2 | 5/2008 |
| WO | WO 2008/079460 | A2 | 7/2008 |
| WO | WO 2008/081910 | A1 | 7/2008 |
| WO | WO 2008/121687 | A2 | 10/2008 |
| WO | WO 2008/124153 | A1 | 10/2008 |
| WO | WO 2008/133192 | A1 | 11/2008 |
| WO | WO 2008/134553 | A1 | 11/2008 |
| WO | WO 2008/138834 | A1 | 11/2008 |

(56) References Cited

FOREIGN PATENT DOCUMENTS

| | | | |
|---|---|---|---|
| WO | WO 2008/141079 A1 | | 11/2008 |
| WO | WO 2008/156614 A2 | | 12/2008 |
| WO | WO 2009/005675 A1 | | 1/2009 |
| WO | WO 2009/016286 A2 | | 2/2009 |
| WO | WO 2009/016560 A2 | | 2/2009 |
| WO | WO 2009/017701 A2 | | 2/2009 |
| WO | WO 2009/021990 A1 | | 2/2009 |
| WO | WO 2009/023253 A2 | | 2/2009 |
| WO | WO 2009/024585 A2 | | 2/2009 |
| WO | WO 2009/037394 A2 | | 3/2009 |
| WO | WO 2009/060197 A1 | | 5/2009 |
| WO | WO 2009/061856 A1 | | 5/2009 |
| WO | WO 2009/077334 A1 | | 6/2009 |
| WO | WO 2009/081857 A1 | | 7/2009 |
| WO | WO 2009/086123 A1 | | 7/2009 |
| WO | WO 2009/086130 A1 | | 7/2009 |
| WO | WO 2009/097233 A1 | | 8/2009 |
| WO | WO 2009/108546 A1 | | 9/2009 |
| WO | WO 2009/112679 A1 | | 9/2009 |
| WO | WO 2009/117157 A1 | | 9/2009 |
| WO | WO 2009/124653 A2 | | 10/2009 |
| WO | WO 2009/126691 A1 | | 10/2009 |
| WO | WO 2009/143156 A2 | | 11/2009 |
| WO | WO 2009/146358 A1 | | 12/2009 |
| WO | WO 2009/152072 A1 | | 12/2009 |
| WO | WO 2010/002985 A1 | | 1/2010 |
| WO | WO 2010/009155 A2 | | 1/2010 |
| WO | WO 2010/011837 A1 | | 1/2010 |
| WO | WO 2010/016005 A1 | | 2/2010 |
| WO | WO 2010/018327 A1 | | 2/2010 |
| WO | WO 2010/033906 A2 | | 3/2010 |
| WO | WO 2010/036407 A2 | | 4/2010 |
| WO | WO 2010/047279 A1 | | 4/2010 |
| WO | WO 2010/048149 A2 | | 4/2010 |
| WO | WO 2010/054253 A1 | | 5/2010 |
| WO | WO 2010/059836 A1 | | 5/2010 |
| WO | WO 2010/059838 A2 | | 5/2010 |
| WO | WO 2010/069684 A1 | | 6/2010 |
| WO | WO 2010/084425 A1 | | 7/2010 |
| WO | WO 2010/084690 A1 | | 7/2010 |
| WO | WO 2010/088368 A2 | | 8/2010 |
| WO | WO 2010/088518 A2 | | 8/2010 |
| WO | WO 2010/097367 A1 | | 9/2010 |
| WO | WO 2010/098458 A1 | | 9/2010 |
| WO | WO 2010/101230 | | 9/2010 |
| WO | WO 2010/108074 A2 | | 9/2010 |
| WO | WO 2010/110277 A1 | | 9/2010 |
| WO | WO 2010097367 A1 | * | 9/2010 |
| WO | WO 2010/119264 A1 | | 10/2010 |
| WO | WO 2010/138833 | | 12/2010 |
| WO | WO 2011/013729 A1 | | 2/2011 |
| WO | WO 2011/021520 A1 | | 2/2011 |
| WO | WO 2011/051342 A1 | | 5/2011 |
| WO | WO 2011/059099 A1 | | 5/2011 |
| WO | WO 2011/089400 A1 | | 7/2011 |
| WO | WO 2011/110545 A1 | | 9/2011 |
| WO | WO 2012/104293 A1 | | 8/2012 |
| WO | WO 2012/146644 A1 | | 11/2012 |
| WO | WO 2013/000924 A1 | | 1/2013 |
| WO | WO 2013/034755 A1 | | 3/2013 |
| WO | WO 2013/034761 A1 | | 3/2013 |
| WO | WO 2014/009305 A1 | | 1/2014 |

OTHER PUBLICATIONS

Bertelsen, et al., Arch Gen Psychiatry, 65:762 (2008).

Boess, Neuropharmacology, 47, 1081-1092, 2004.

Bouloc, et al. "Structure-based design of imidazo[1,2-a]pyrazine derivatives as selective inhibitors of Aurora-A kinase in cells", Bioorganic & Medicinal Chemistry Letters (2010), 20(20), 5988-5993.

Blokland et al., Expert Opin. Ther. Patents (2012) 22(4), pp. 349-354.

Calverley, M.J. Tetrahedron, 1987, 43(20), 4609-19.

Charych et al., The Journal of Neuroscience, Jul. 7, 2010 • 30(27):9027-9037.

Enhancer, Behav Brain Res 1988, 31, 47-59.

Gaudry et al., Organic Syntheses, 1976, 55, 24-27.

Gehlert, et al. "3-(4-Chloro-2-morpholin-4-yl-thiazol-5-yl)-8-(1-ethylpropyl)-2,6-dimethyl- imidazo[1,2-b]pyridazine: a novel brain-penetrant, orally available corticotropin-releasing factor receptor 1 antagonist with efficacy in animal models of alcoholism", Journal of Neuroscience (2007), 27(10), 2718-2726.

Gennaro et al. Remington's Pharmaceutical Sciences ($18^{th}$ ed., Mack Publishing Company, 1990, see especially Part 8: Pharmaceutical preparations and their Manufacture), pp. 1435-1712 (split/uploaded into 4 separate files due to size).

Gudmundsson, et al. "Imidazo[1,2-a]pyridines with potent activity against herpesviruses", Bioorganic & Medicinal Chemistry Letters (2007), 17(10), 2735-2739.

Gudmundsson, et al. "Synthesis of Novel Imidazo[1,2-a]pyridines with Potent Activity against Herpesviruses", Organic Letters (2003), 5(8), 1369-1372 CODEN: ORLEF7; ISSN: 1523-7060.

Hebb et al., Current Opinion in Pharmacology 2007, 7:86-92.

Harig et al., J. Translational Med. 2:44 (2004).

Il'icheva, et al. "Theoretical Study of the Structure of Adenosine Deaminase Complexes with Adenosine Analogues: I. Aza-, Deaza-, and Isomeric Azadeazaanalogues of Adenosine", Russian Journal of Bioorganic Chemistry (2005), 31(5), 439-452.

Kehler et al., Expert Opin. Ther. Patents (2007) 17(2), pp. 147-158.

Kehler et al. Expert Opin. Ther. Patents (2009) 19(12), pp. 1715-1725.

Kehler, et al., Expert Opin. Ther. Pat., "Phosphodiesterase 10A inhibitors: a 2009-20012 patent update", pp. 1-15 (Dec. 5, 2012).

Kerekes, et al. "Aurora Kinase Inhibitors Based on the Imidazo[1,2-a]pyrazine Core: Fluorine and Deuterium Incorporation Improve Oral Absorption and Exposure" Journal of Medicinal Chemistry (2011), 54(1), 201-210.

Kobe, et al. "Use of distance geometry approach for the in vitro antiviral activity evaluation of N-bridgehead C-nucleosides", European Journal of Medicinal Chemistry (1992), 27(3), 259-66.

Kolar, et al. "Transformations of the pyrido[1,2-a]pyrazine ring system into imidazo[1,2-a]pyridines, imidazo[1,2-a]pyrimidines and 2-oxa-6a,10c-diazaaceanthrylenes", Journal of Heterocyclic Chemistry (1996), 33(3), 639-642.

Lhassani, et al. "Synthesis and antiviral activity of imidazo[1,2-a]pyridines", European Journal of Medicinal Chemistry (1999), 34(3), 271-274.

MacCoss, et al. "Synthesis and biological evaluation of nucleosides containing 8-aminoimidazo[1,2-a]pyrazine as an isosteric replacement for adenine", Journal of Heterocyclic Chemistry (1993), 30(5), 1213-20.

Masood, J Pharmacol Exp Ther, 326(2), 369-379, 2008.

Meng, et al. "Bioisosteric approach to the discovery of imidazo[1,2-a]pyrazines as potent Aurora kinase inhibitors" Bioorganic & Medicinal Chemistry Letters (2011), 21(1), 592-598.

Owen, Bioorganic & Medicinal Chemistry, Letters, vol. 17, No. 2, pp. 486-490.

Pan, et al. "Synthesis of novel isoxazolinyl substituted imidazo[1,2-a]pyridine C-nucleoside analogs", Tetrahedron Letters (1998), 39(45), 8191-8194.

Pandit, Proc. Natl. Acad. Sci. USA, 106(43), 18225-30, 2009.

Prickaerts, Neuroscience, 2002:113: :351-361.

Reneerkens O et al Behavioral Brain Research, 236, 16-22,2013.

Schmidt et al., The Journal of Pharmacology and Experimental Therapeutics, vol. 325, No. 2, pp. 681-690.

Siuciak, Judith A., CNS Drugs 2008; 22 (12): 983-993.

Siuciak, et al., Expert Opin. Drug Discov. 2:1001 (2007).

van den Heuvel, M. et al.; J. Org. Chem., 2004, 250.

Wang, et al. "Synthesis of novel isoxazolinyl substituted imidazo]1,2-a]pyridine C-nucleoside analogs", Hecheng Huaxue (2001), 9(5), 386-389.

Wang, X. et al. Tetrahedron Lett., 2000, 4335-4338.

West, Frontiers in Systems Neuroscience, vol. 5, 2011, Article 55, pp. 1-9.

(56) References Cited

OTHER PUBLICATIONS

Yu, Tao et al. "Discovery of a Potent, Injectable Inhibitor of Aurora Kinases Based on the Imidazo-[1,2-a]-Pyrazine Core", ACS Medicinal Chemistry Letters (2010), 1(5), 214-218.
Zarubin, et al. "Theoretical study of adenosine and its isosteric analogs. A possible mechanism of their binding in an active site of mammalian adenosine deaminase", Vestnik Samarskogo Gosudarstvennogo Universiteta, Estestvennonauchnaya Seriya (2003), (Spec.), 152-173.
International Search Report for PCT/EP2011/066264 dated Dec. 8, 2010.
International Search Report for PCT/EP2011/053445 dated Aug. 18, 211.
International Search Report for PCT/EP2013/063244 dated Aug. 16, 2013.
International Search Report for PCT/EP2013/064355 dated Oct. 10, 2013.
Aggarwal, Synthetic Communications, pp. 1873-1878, 2006.
Aggarwal et al., Journal of Fluorine Chemistry (2009), 130 (10), 886-893.
Baratti et al., Behav. Pharmacol. 1999;10: 731-737.
Domek--Łopacińska Ku, Strosznajder JB Mol Neurobiol. 2010; 41(2-3):129-37).
Kumar, Green Chemistry, pp. 156-157, 2004.
Kumar P, et al. Behav Pharmacol. May 2010;21(3):217-30).
Mennitti, F. S. et al. Nature Rev. Drug Discovery 2006, 5, 660-669.
Miller et al. Angew. Chem. Int. Ed. 2008, 47, 8998-9033.
Reierson, G.W. et al. Current Neuropharmacology 2011; 9:715-727).

* cited by examiner

1-ARYL-4-METHYL-[1,2,4]TRIAZOLO [4,3-A]QUINOXALINE DERIVATIVES

CROSS REFERENCE TO RELATED APPLICATIONS

This application is the national stage of PCT Application No. PCT/EP2012/062381, filed Jun. 26, 2012, which claims priority from European Patent Application No. 11171519.9, filed Jun. 27, 2011, the entire disclosures of which are hereby incorporated in their entirety.

FIELD OF THE INVENTION

The present invention relates to novel 1-aryl-4-methyl-[1,2,4]triazolo[4,3-a]-quinoxaline derivatives as inhibitors of phosphodiesterase 2 (PDE2) and to a lesser extent of phosphodiesterase 10 (PDE10) or as inhibitors of both, phosphodiesterases 2 and 10. The invention is also directed to pharmaceutical compositions comprising such compounds, to processes for preparing such compounds and compositions, and to the use of such compounds and compositions for the prevention and treatment of disorders in which PDE2 is involved, or disorders in which both PDE2 and PDE10 are involved, such as neurological and psychiatric disorders, and endocrinological or metabolic diseases. The present invention also relates to radiolabelled compounds which may be useful for imaging and quantifying the PDE2 enzyme in tissues, for example, using positron-emission tomography (PET). The invention is also directed to compositions comprising such compounds, to processes for preparing such compounds and compositions, to the use of such compounds and compositions for imaging a tissue, cells or a host, in vitro or in vivo and to precursors of said compounds.

BACKGROUND OF THE INVENTION

Journal of Fluorine Chemistry (2009), 130 (10), 886-893 discloses 1-aryl-4-methyl-[1,2,4]triazolo[3,4-a]quinoxalines wherein aryl is phenyl, 4-methoxyphenyl, 4-chlorophenyl or 4-nitrophenyl, unexpectedly arising in a reaction of 2-hydrazine-3-methylquinoxaline with trifluoromethyl-beta-diketones.

Green Chemistry (2004), 6, 156-157 discloses solvent-free methods for the synthesis of 1-aryl-4-methyl-[1,2,4]triazolo[3,4-a]quinoxalines wherein aryl is phenyl, 4-methylphenyl, 4-chlorophenyl, 4-methoxyphenyl and 3-methoxyphenyl. Synthetic Communications (2006), 36, 1873-1878 discloses methods for the synthesis of 1-aryl-4-methyl-[1,2,4]triazolo[3,4-a]quinoxalines wherein aryl is phenyl, 4-methylphenyl, 4-chlorophenyl, 2-methoxyphenyl and 4-methoxyphenyl. WO-2010/101230 discloses [1,2,4]triazolo[4,3-a]quinoxalin-4(5H)-ones as PDE9 inhibitors useful for treating urination disorders.

Phosphodiesterases (PDEs) are a family of enzymes encoded by 21 genes and subdivided into 11 distinct families according to structural and functional properties.

These enzymes metabolically inactivate widely occurring intracellular second messengers, 3',5'-cyclic adenosine monophosphate (cAMP) and 3',5'-cyclic guanosine monophosphate (cGMP). These two messengers regulate a wide variety of biological processes, including pro-inflammatory mediator production and action, ion channel function, muscle contraction, learning, differentiation, apoptosis, lipogenesis, glycogenolysis, and gluconeogenesis. They do this by activation of protein kinase A (PKA) and protein kinase G (PKG), which in turn phosphorylate a wide variety of substrates including transcription factors and ion channels that regulate innumerable physiological responses. In neurons, this includes the activation of cAMP and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by PDEs. PDEs are hydrolases that inactivate cAMP and cGMP by catalytic hydrolysis of the 3'-ester bond, forming the inactive 5'-monophosphate (Scheme A).

Scheme A

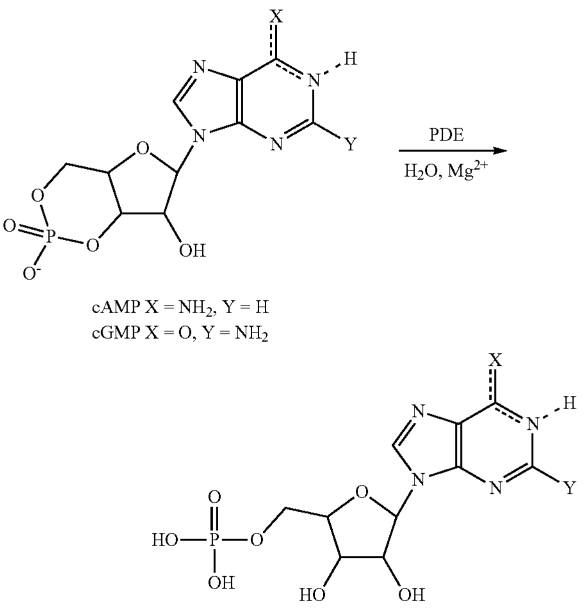

cAMP X = $NH_2$, Y = H
cGMP X = O, Y = $NH_2$

5'-AMP/GMP

On the basis of substrate specificity, the PDE families can be divided into three groups: i) the cAMP-specific PDEs, which include PDE4, 7 and 8; ii) the cGMP-selective enzymes PDE5, 6 and 9; and iii) the dual-substrate PDEs, PDE1, 2 and 3, as well as PDE10 and 11.

Furthermore, PDEs are expressed differentially throughout the organism, including the central nervous system. Different PDE isozymes therefore may have different physiological functions. Compounds that inhibit selectively PDE families or isozymes may display particular therapeutic activity, fewer side effects, or both.

Phosphodiesterase 2A (PDE2A) inactivates intracellular signalling mechanisms reliant on cyclic nucleotide signalling mediated by cAMP and cGMP via their degradation.

Such signalling pathways are known to play a role in the regulation of genes involved in the induction of synaptic plasticity.

The pharmacological inhibition of PDE2 therefore causes increased levels of synaptic plasticity (an underlying correlate of learning and memory), suggesting that PDE2A modulation may be a target for alleviating cognitive deficits seen in people suffering from disorders such as for example, schizophrenia, Alzheimer's disease, Parkinson's disease and other CNS disorders associated with cognitive dysfunction.

Phosphodiesterase 2A (PDE2A) is more abundantly expressed in the brain relative to peripheral tissues. The high expression of PDE2 in the limbic system (isocortex, hippocampus, amygdala, habenula, basal ganglia) suggests that PDE2 may modulate neuronal signalling involved in emotion, perception, concentration, learning and memory. Additionally, PDE2 is expressed in the nucleus accumbens, the olfactory bulb, the olfactory tubercle and the amygdala, supporting the suggestion that PDE2 may also be involved in anxiety and depression.

Additionally, PDE2 inhibitors have been shown to be beneficial in the reduction of oxidative stress-induced anxiety, supporting their use in the treatment of anxiety in neuropsychiatric and neurodegenerative disorders that involve oxidative stress, such as Alzheimer's disease, Parkinson's disease and multiple sclerosis.

PDE2 inhibitors have been shown to enhance long term potentiation of synaptic transmission and to improve memory acquisition and consolidation in the object recognition and in the social recognition tests in rats. Furthermore, PDE2 inhibitors have been shown to reverse the MK-801 induced working memory deficit in the T-maze in mice. PDE2 inhibitors have also been shown to display activity in forced swim test and light/dark box models; and to show anxiolytic-like effects in elevated plus-maze, hole-board and open-field tests and to prevent stress-induced changes in apoptosis and behaviour.

Thus, PDE2 inhibitors may be useful in the treatment of memory deficiency, cognitive disorders, anxiety, bipolar disorder and depression.

Of all the 11 known PDE families, PDE10 has the most restricted distribution with high expression only in the brain and testes. In the brain, PDE10A mRNA and protein are highly expressed in a majority of striatal Medium Spiny Neurons (MSNs). This unique distribution of PDE10A in the brain, together with its increased pharmacological characterization, indicates a potential use of PDE10A inhibitors for treating neurological and psychiatric disorders like schizophrenia.

Thus, PDE10 inhibitors may possess a pharmacological profile similar to that of the current antipsychotics which mainly treat positive symptoms of schizophrenia, but also having the potential to improve the negative and cognitive symptoms of schizophrenia, while lacking the non-target related side effects such as EPS or prolactin release, that are often observed with the currently available antipsychotics.

Since PDE10 inhibitors can be used to raise levels of cAMP and/or cGMP within cells that express the PDE10 enzyme, for example neurons that comprise the basal ganglia, PDE10 inhibitors may be useful in treating schizophrenia and additionally, a variety of conditions as described herein, for example, Parkinson's Disease, Huntington's Disease, addiction and depression. PDE10 inhibitors may be also useful in other conditions such as obesity, non-insulin dependent diabetes, bipolar disorder, obsessive compulsive disorder and pain.

While PDE2 inhibitors may provide an advantageous balance of properties in the treatment of disorders selected from, but not limited to, cognitive disorders, anxiety, depression, and movement disorders; compounds that are PDE2 and PDE10 inhibitors may show utility in schizophrenia, Parkinson's disease, Huntington's disease, addiction, depression, and anxiety, with an additional beneficial effect in cognitive deficits and/or drug-induced extrapyramidal symptoms observed in these patient populations.

SUMMARY OF THE INVENTION

It is the object of the present invention to provide novel compounds that are inhibitors of PDE2 and to a lesser extent of PDE10, or that are inhibitors of both PDE2 and 10. The present compounds are compounds which, due to their novel mode of action are potentially useful in the treatment of diseases related to PDE2 enzyme activity or diseases related to the activity of the PDE2 and 10 enzymes.

Thus, the present invention is directed to a 1-aryl-4-methyl-[1,2,4]triazolo[4,3-a]-quinoxalines of formula (I)

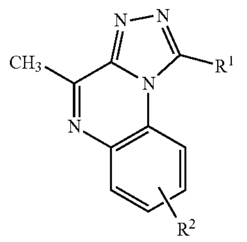

(I)

or a stereochemically isomeric form thereof, wherein $R^1$ is phenyl or pyridinyl, each optionally substituted with 1 or 2 substituents independently selected from the group consisting of halo, $C_{1-6}$alkyl, $C_{1-6}$alkyl substituted with 1, 2 or 3 halo substituents, $C_{1-6}$alkyloxy, $(C_{3-6}$cycloalkyl$)C_{1-3}$ alkyloxy, $C_{1-6}$alkyloxy substituted with 1, 2 or 3 halo substituents, $(C_{1-6}$alkyloxy$)C_{1-3}$alkyl and $(C_{1-6}$alkyloxy$)$ $C_{1-3}$ alkyloxy;

$R^2$ is selected from the group consisting of hydrogen, halo, trifluoromethyl, trifluoromethoxy, 1,1-difluoroethoxy, cyano, $(C_{3-6}$cycloalkyl)carbonyl, $C_{2-6}$alkenyl, a radical of formula $-L^1-NR^3R^4$, or a radical of formula $-L^2-O-R^5$;

$L^1$ and $L^2$ each are a covalent bond, $CH_2$, $CH(CF_3)$ or $C(=O)$;

$R^3$ is hydrogen or methyl;

$R^4$ is selected from the group consisting of hydrogen; $C_{1-3}$alkyl optionally substituted with 1 or 2 substituents independently selected from the group consisting of halo, hydroxy, $C_{1-3}$alkoxy, mono- and di$(C_{1-3}$alkyl)amino, $C_{3-6}$cycloalkyl, phenyl, 3,4,5-trimethoxyphenyl, pyridinyl, pyridinyl substituted with halo, morpholinyl, pyrrolidinyl, piperidinyl, and piperidinyl substituted with methyl; $C_{3-6}$cycloalkyl; tetrahydropyranyl; 1-methylpiperidin-4-yl; 4-hydroxycyclohexan-1-yl; 3,4,5-trimethoxyphenyl; $C_{1-3}$alkylcarbonyl; and pyridinyl; or $NR^3R^4$ is pyrrolidinyl, piperidinyl or morpholinyl, each optionally substituted with 1 or 2 substituents independently selected from the group consisting of halo, trifluoromethyl, hydroxyl, $C_{1-3}$alkyloxy, mono- and di$(C_{1-3}$alkyl)amino, hydroxyl-$C_{1-3}$alkyl, halo$C_{1-3}$alkyl, and methoxy$C_{1-3}$alkyl; or 4-methylpiperazin-1-yl;

$R^5$ is selected from the group consisting of hydrogen; $C_{1-3}$alkyl; $C_{1-3}$alkyl substituted with pyridinyl, phenyl, pyrrolidinyl or morpholinyl; phenyl; and pyridinyl;

or a pharmaceutically acceptable salt or a solvate thereof, provided that $R^2$ is other than hydrogen when $R^1$ is phenyl, 4-methylphenyl, 2-methoxyphenyl, 3-methoxyphenyl, 4-methoxyphenyl, or 4-chlorophenyl.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by the PDE2 enzyme or by the PDE2 and PDE10 enzymes, comprising administering to a subject in need thereof a therapeutically effective amount of any of the compounds or pharmaceutical compositions described above.

Further exemplifying the invention are methods of inhibiting the PDE2 enzyme or inhibiting the PDE2 and the PDE10 enzymes, comprising administering to a subject in need thereof a therapeutically effective amount of any of the compounds or pharmaceutical compositions described above.

An example of the invention is a method of treating a disorder selected from the group consisting of neurological and psychiatric disorders, and endocrinological or metabolic diseases comprising administering to a subject in need thereof, a therapeutically effective amount of any of the compounds or pharmaceutical compositions described above.

An example of the invention is a method of treating a disorder selected from the group of neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; pain; autistic disorder; and metabolic disorders, comprising administering to a subject in need thereof, a therapeutically effective amount of any of the compounds or pharmaceutical compositions described above.

An example of the invention is a method of treating a disorder selected from the group consisting of neurological and psychiatric disorders, and endocrinological or metabolic diseases comprising administering to a subject in need thereof, a therapeutically effective amount of any of the compounds or pharmaceutical compositions described above.

An example of the invention is a method of treating a disorder selected from the group of neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; pain; autistic disorder; and metabolic disorders, comprising administering to a subject in need thereof, a therapeutically effective amount of any of the compounds or pharmaceutical compositions described above.

Also exemplifying the invention is a compound or a pharmaceutical composition described above for use as a medicament.

Further exemplifying the invention is a compound according to the present invention or a pharmaceutical composition according to the invention for use in the treatment, prevention, amelioration, control or reduction of the risk of various neurological and psychiatric disorders associated with phosphodiesterase 2 or associated with phosphodiesterases 2 and 10 dysfunction in a mammal, including a human, the treatment or prevention of which is affected or facilitated by the inhibition of phosphodiesterase 2 or by the inhibition of phosphodiesterases 2 and 10.

An example of the invention is a compound according to the present invention or a pharmaceutical composition according to the invention for use in the treatment, prevention, amelioration, control or reduction of the risk of various disorders selected from psychotic disorders and conditions; anxiety disorders; movement disorders; drug abuse; mood disorders; neurodegenerative disorders; disorders or conditions comprising as a symptom a deficiency in attention and/or cognition; pain; autistic disorder; and metabolic disorders.

An example of the invention is a method of treating a disorder selected from the group consisting of Alzheimer's disease, mild cognitive impairment, senility, dementia, dementia with Lewy bodies, Down's syndrome, dementia associated with stroke, dementia associated with Parkinson's disease and dementia associated with beta-amyloid, preferably Alzheimer's disease, comprising administering to a subject in need thereof, a therapeutically effective amount of any of the compounds or pharmaceutical compositions described above.

Another example of the invention is any of the compounds described above for use in treating: (a) Alzheimer's Disease, (b) mild cognitive impairment, (c) senility, (d) dementia, (e) dementia with Lewy bodies, (f) Down's syndrome, (g) dementia associated with stroke, (h) dementia associated with Parkinson's disease, (i) dementia associated with beta-amyloid, (j) depressive disorders and (k) anxiety disorders, in a subject in need thereof.

Another aspect of the invention relates to precursor compounds for the synthesis of radiolabelled compounds of formula (I).

Illustrative of the invention is a sterile solution comprising a radiolabelled compound of Formula (I).

Exemplifying the invention is a use of a radiolabelled compound of formula (I) as described herein, for, or a method of, imaging a tissue, cells or a host, in vitro or in vivo.

Further exemplifying the invention is a method of imaging a tissue, cells or a host, comprising contacting with or administering to a tissue, cells or a host a compound of formula (I) as described herein, and imaging the tissue, cells or host with a positron-emission tomography imaging system.

DETAILED DESCRIPTION OF THE INVENTION

The present invention is directed to compounds of formula (I) as defined hereinbefore, and pharmaceutically acceptable salts thereof. The compounds of formula (I) are inhibitors of the phosphodiesterase 2 enzyme (PDE2) and to a lesser extent of phosphodiesterase 10 (PDE10), or are inhibitors of the phosphodiesterase 2 and phosphodiesterase 10 enzymes (PDE2 and PDE10) and may be useful in the treatment of neurological and psychiatric disorders, and endocrinological or metabolic diseases.

In an embodiment, the present invention relates to a compound of formula (I), or a stereochemically isomeric form thereof, as defined herein, wherein $R^1$ is phenyl or pyridinyl, each optionally substituted with 1 or 2 substituents independently selected from the group consisting of halo, $C_{1-6}$alkyl, trifluoromethyl, $C_{1-6}$alkyloxy, ($C_{3-6}$cycloalkyl)$C_{1-3}$alkyloxy and trifluoromethoxy;

$R^2$ is selected from the group consisting of hydrogen, halo, trifluoromethyl, trifluoromethoxy, 1,1-difluoroethoxy, cyano, ($C_{3-6}$cycloalkyl)carbonyl, $C_{2-6}$alkenyl, a radical of formula $-L^1-NR^3R^4$, or a radical of formula $-L^2-O-R^5$;

$L^1$ and $L^2$ each are a covalent bond, $CH_2$, $CH(CF_3)$ or $C(=O)$;

$R^3$ is hydrogen or methyl;

$R^4$ is selected from the group consisting of hydrogen; $C_{1-3}$alkyl optionally substituted with 1 or 2 substituents independently selected from the group consisting of halo, hydroxy, $C_{1-3}$alkoxy, mono- and di($C_{1-3}$alkyl)amino, $C_{3-6}$cycloalkyl, phenyl, 3,4,5-trimethoxyphenyl, pyridinyl, pyridinyl substituted with halo, morpholinyl, pyrrolidinyl, piperidinyl, and piperidinyl substituted with methyl; $C_{3-6}$cycloalkyl; tetrahydropyranyl; 1-methylpiperidin-4-yl; 4-hydroxycyclohexan-1-yl; 3,4,5-trimethoxyphenyl; $C_{1-3}$alkylcarbonyl; and pyridinyl; or $NR^3R^4$ is pyrrolidinyl, piperidinyl or morpholinyl, each optionally substituted with 1 or 2 substituents independently selected from the group consisting of halo, trifluoromethyl, hydroxyl, $C_{1-3}$alkyloxy, mono- and di($C_{1-3}$alkyl)amino, hydroxyl-$C_{1-3}$alkyl, halo$C_{1-3}$alkyl, and methoxy$C_{1-3}$alkyl; or 4-methylpiperazin-1-yl;

$R^5$ is selected from the group consisting of hydrogen; $C_{1-3}$alkyl; $C_{1-3}$alkyl substituted with pyridinyl, phenyl, pyrrolidinyl or morpholinyl; phenyl; and pyridinyl;

or a pharmaceutically acceptable salt or a solvate thereof, provided that $R^2$ is other than hydrogen when $R^1$ is phenyl, 4-methylphenyl, 2-methoxyphenyl, 3-methoxyphenyl, 4-methoxyphenyl, or 4-chlorophenyl.

In another embodiment, the present invention relates to a compound of formula (I), wherein $R^1$ is phenyl or pyridinyl, each optionally substituted with 1 or 2 substituents independently selected from the group consisting of halo, $C_{1-6}$alkyl, and $C_{1-6}$alkyloxy;

$R^2$ is selected from the group consisting of hydrogen, halo, trifluoromethoxy, 1,1-difluoroethoxy, cyano, ($C_{3-6}$cycloalkyl)carbonyl, $C_{2-6}$alkenyl, a radical of formula $-L^1-NR^3R^4$, or a radical of formula $-L^2-O-R^5$;

$L^1$ and $L^2$ each are a covalent bond, $CH_2$, $CH(CF_3)$ or $C(=O)$;

$R^3$ is hydrogen or methyl;

$R^4$ is selected from the group consisting of hydrogen; $C_{1-3}$alkyl optionally substituted with a substituent selected from the group consisting of halo, hydroxy, $C_{1-3}$alkoxy, mono- and di($C_{1-3}$alkyl)amino, phenyl, 3,4,5-trimethoxyphenyl, pyridinyl, pyridinyl substituted with halo, morpholinyl, pyrrolidinyl, and piperidinyl; tetrahydropyranyl; 1-methylpiperidin-4-yl; 4-hydroxycyclohexan-1-yl; 3,4,5-trimethoxyphenyl; $C_{1-3}$alkylcarbonyl; pyridinyl; or $NR^3R^4$ is pyrrolidinyl, piperidinyl or morpholinyl, each optionally substituted with 1 or 2 substituents independently selected from the group consisting of halo, trifluoromethyl, hydroxyl, $C_{1-3}$alkyloxy, hydroxy$C_{1-3}$alkyl, halo$C_{1-3}$alkyl, and methoxy$C_{1-3}$alkyl; or 4-methylpiperazin-1-yl;

$R^5$ is selected from the group consisting of hydrogen; $C_{1-3}$alkyl; $C_{1-3}$alkyl substituted with pyridinyl, phenyl, or morpholinyl; phenyl; and pyridinyl;

or a pharmaceutically acceptable salt or a solvate thereof, provided that $R^2$ is other than hydrogen when $R^1$ is phenyl, 4-methylphenyl, 2-methoxyphenyl, 3-methoxyphenyl, 4-methoxyphenyl, or 4-chlorophenyl.

In an additional embodiment, $R^2$ is not hydrogen, and the rest of variables as previously defined in any of the above embodiments.

In an embodiment, the present invention relates to a compound of formula (I), wherein $R^1$ is phenyl or pyridinyl each optionally substituted with 1 or 2 substituents independently selected from the group consisting of halo, and $C_{1-6}$alkyloxy;

$R^2$ is selected from the group consisting of halo, cyano, a radical of formula $-L^1-NR^3R^4$; or a radical of formula $-L^2-O-R^5$;

$L^1$ and $L^2$ each are a covalent bond, $CH_2$ or $C(=O)$;

$R^3$ is hydrogen or methyl;

$R^4$ is selected from the group consisting of $C_{1-3}$alkyl optionally substituted with a substituent selected from the group consisting of halo, $C_{1-3}$alkoxy, mono- and di($C_{1-3}$alkyl) amino, phenyl, pyridinyl, pyridinyl substituted with halo, morpholinyl, and piperidinyl; 1-methylpiperidin-4-yl; 3,4,5-trimethoxyphenyl; pyridinyl; or $NR^3R^4$ is pyrrolidinyl, piperidinyl or morpholinyl each optionally substituted with 1 or 2 substituents independently selected from the group consisting of halo and hydroxyl; or 4-methylpiperazin-1-yl;

$R^5$ is $C_{1-3}$alkyl substituted with pyridinyl;

or a pharmaceutically acceptable salt or a solvate thereof.

In an additional embodiment, the present invention relates to a compound of formula (I), wherein $R^2$ is bound to the scaffold at position 8 and $R^1$ and $R^2$ are as previously defined. Thus, in an additional embodiment, the present invention is directed to a compound of formula (I')

(I')

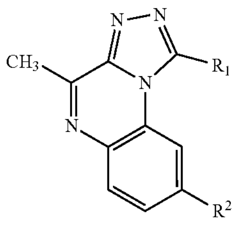

or a stereochemically isomeric form thereof, wherein $R^1$ and $R^2$ are as previously defined in any of the above embodiments, or a pharmaceutically acceptable salt or a solvate thereof.

In an additional embodiment, the present invention relates to a compound of formula (I), wherein $R^1$ is pyridinyl substituted with $C_{1-6}$alkyloxy and $R^2$ is as previously defined in any of the above embodiments, or a pharmaceutically acceptable salt or a solvate thereof.

In an additional embodiment, the present invention relates to a compound of formula (I), wherein $R^1$ and $R^2$ are as previously defined in any of the above embodiments, and wherein $-L^1-NR^3R^4$ is selected from $-CH_2-NR^{3a}R^{4a}$ wherein $R^{3a}$ is hydrogen or methyl;

$R^{4a}$ is selected from the group consisting of $C_{1-3}$alkyl optionally substituted with a substituent selected from the group consisting of $C_{3-6}$cycloalkyl and phenyl; $C_{3-6}$cycloalkyl; tetrahydropyranyl; 4-hydroxycyclohexan-1-yl; and pyridinyl; or $NR^{3a}R^{4a}$ is pyrrolidinyl, piperidinyl or morpholinyl, each optionally substituted with 1 or 2 substituents independently selected from the group consisting of halo, trifluoromethyl, hydroxyl, $C_{1-3}$alkyloxy, mono- and di($C_{1-3}$alkyl)amino, hydroxyl-$C_{1-3}$alkyl, halo$C_{1-3}$alkyl, and methoxy$C_{1-3}$alkyl; or 4-methylpiperazin-1-yl; or $-CH(CF_3)-NR^{3b}R^{4b}$ wherein $R^{3b}$ is hydrogen and $R^{4b}$ is $C_{1-3}$alkyl; or $NR^{3b}R^{4b}$ is morpholinyl; or $-C(=O)-NR^{3c}R^{4c}$ wherein $R^3$ is hydrogen or methyl;

$R^{4c}$ is selected from the group consisting of hydrogen; $C_{1-3}$alkyl optionally substituted with a substituent selected from the group consisting of halo, hydroxy, $C_{1-3}$alkoxy, mono- and di($C_{1-3}$alkyl)amino, phenyl, pyridinyl, pyridinyl substituted with halo, morpholinyl, pyrrolidinyl, and piperidinyl; 1-methylpiperidin-4-yl; and 3,4,5-trimethoxyphenyl; or -covalent bond-$NR^{3d}R^{4d}$ wherein
$R^{3d}$ is hydrogen or methyl;
$R^{4d}$ is selected from the group consisting of hydrogen; $C_{1-3}$alkyl optionally substituted with a substituent selected from the group consisting of $C_{1-3}$alkoxy, and morpholinyl; $C_{3-6}$cycloalkyl; 1-methylpiperidin-4-yl; and $C_{1-3}$alkylcarbonyl; or
$NR^{3d}R^{4d}$ is 4-methylpiperazin-1-yl; and
$-L^2$-O—$R^5$ is selected from
covalent bond-O—$R^{5a}$ wherein $R^{5a}$ is selected from the group consisting of hydrogen; $C_{1-3}$alkyl; $C_{1-3}$alkyl substituted with pyridinyl, pyrrolidinyl or morpholinyl; and pyridinyl; or
—$CH_2$—O—$R^{5b}$ wherein $R^{5b}$ is selected from the group consisting of hydrogen; $C_{1-3}$alkyl; and phenyl; or
—C(═O)—O—$R^{5c}$ wherein $R^{5c}$ is selected from the group consisting of hydrogen; $C_{1-3}$alkyl; and $C_{1-3}$alkyl substituted with pyridinyl or phenyl; or
—$CH(CF_3)$—O—H;
or a pharmaceutically acceptable salt or a solvate thereof.

In an additional embodiment, the present invention relates to a compound of formula (I), wherein $R^1$ and $R^2$ are as previously defined in any of the above embodiments, and wherein
$-L^1$-$NR^3R^4$ is selected from
—$CH_2$—$NR^{3a}R^{4a}$ wherein
$R^{3a}$ is hydrogen or methyl;
$R^{4a}$ is selected from the group consisting of $C_{1-3}$alkyl optionally substituted with phenyl; tetrahydropyranyl; 4-hydroxycyclohexan-1-yl; and pyridinyl; or
$NR^{3a}R^{4a}$ is pyrrolidinyl, piperidinyl or morpholinyl, each optionally substituted with 1 or 2 substituents independently selected from the group consisting of halo, trifluoromethyl, hydroxyl, $C_{1-3}$alkyloxy, mono- and di($C_{1-3}$alkyl)amino, hydroxyl-$C_{1-3}$alkyl, halo$C_{1-3}$alkyl, and methoxy$C_{1-3}$alkyl; or 4-methylpiperazin-1-yl; or
—$CH(CF_3)$—$NR^{3b}R^{4b}$ wherein
$R^{3b}$ is hydrogen and $R^{4b}$ is $C_{1-3}$alkyl; or
$NR^{3b}R^{4b}$ is morpholinyl; or
—C(═O)—$NR^{3c}R^{4c}$ wherein
$R^{3a}$ is hydrogen or methyl;
$R^{4c}$ is selected from the group consisting of hydrogen; $C_{1-3}$alkyl optionally substituted with a substituent selected from the group consisting of halo, hydroxy, $C_{1-3}$alkoxy, mono- and di($C_{1-3}$alkyl)amino, phenyl, pyridinyl, pyridinyl substituted with halo, morpholinyl, pyrrolidinyl, and piperidinyl; 1-methylpiperidin-4-yl; and 3,4,5-trimethoxyphenyl; or
-covalent bond-$NR^{3d}R^{4d}$ wherein
$R^{3d}$ is hydrogen or methyl;
$R^{4d}$ is selected from the group consisting of hydrogen; $C_{1-3}$alkyl optionally substituted with a substituent selected from the group consisting of $C_{1-3}$alkoxy, and morpholinyl; 1-methylpiperidin-4-yl; and $C_{1-3}$alkylcarbonyl; or
$NR^{3d}R^{4d}$ is 4-methylpiperazin-1-yl; and
$-L^2$-O—$R^5$ is selected from
-covalent bond-O—$R^{5a}$ wherein $R^{5a}$ is selected from the group consisting of hydrogen; $C_{1-3}$alkyl; $C_{1-3}$alkyl substituted with pyridinyl or morpholinyl; and pyridinyl; or
—$CH_2$—O—$R^{5b}$ wherein $R^{5b}$ is selected from the group consisting of hydrogen; $C_{1-3}$alkyl; and phenyl; or
—C(═O)—O—$R^{5c}$ wherein $R^{5a}$ is selected from the group consisting of hydrogen; $C_{1-3}$alkyl; and $C_{1-3}$alkyl substituted with pyridinyl or phenyl; or
—$CH(CF_3)$—O—H;
or a pharmaceutically acceptable salt or a solvate thereof.

In an additional embodiment, the present invention relates to a compound of formula (I), wherein $R^1$ and $R^2$ are as previously defined in any of the above embodiments, and wherein
$-L^1$-$NR^3R^4$ is selected from
—$CH_2$—$NR^{3a}R^{4a}$ wherein
$R^{3a}$ is hydrogen or methyl;
$R^{4a}$ is selected from the group consisting of $C_{1-3}$alkyl optionally substituted with phenyl; and pyridinyl; or
$NR^{3a}R^{4a}$ is 1 pyrrolidinyl, piperidinyl or morpholinyl, each optionally substituted with 1 or 2 substituents independently selected from the group consisting of halo, and hydroxyl; or 4-methylpiperazin-1-yl; or
—$CH(CF_3)$—$NR^{3b}R^{4b}$ wherein
$R^{3b}$ is hydrogen and $R^{4b}$ is $C_{1-3}$alkyl; or
$NR^{3b}R^{4b}$ is morpholinyl; or
—C(═O)—$NR^{3c}R^{4c}$ wherein
$R^{3c}$ is hydrogen or methyl;
$R^{4c}$ is selected from the group consisting of $C_{1-3}$alkyl optionally substituted with a substituent selected from the group consisting of halo, $C_{1-3}$alkoxy, mono- and di($C_{1-3}$ alkyl)amino, phenyl, pyridinyl, pyridinyl substituted with halo, morpholinyl, and piperidinyl; 1-methylpiperidin-4-yl; and 3,4,5-trimethoxyphenyl; or
-covalent bond-$NR^{3d}R^{4d}$ wherein
$R^{3d}$ is hydrogen or methyl;
$R^{4d}$ is selected from the group consisting of hydrogen; $C_{1-3}$alkyl optionally substituted with a substituent selected from the group consisting of $C_{1-3}$alkoxy, and morpholinyl; and 1-methylpiperidin-4-yl; or
$NR^{3d}R^{4d}$ is 4-methylpiperazin-1-yl; and
$-L^2$-O—$R^5$ is selected from -covalent bond-O—$R^{5a}$ or —C(═O)—O—$R^{5c}$, wherein $R^{5a}$ and $R^{5c}$ each represent $C_{1-3}$alkyl substituted with pyridinyl;
or a pharmaceutically acceptable salt or a solvate thereof.

In a further embodiment, the present invention relates to a compound of formula (I) as defined herein, wherein $R^1$ is 5-butoxypyridin-3-yl or 5-butoxy-2-chlorophenyl and $R^2$ is

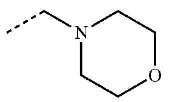
or
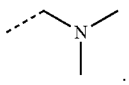
.

In a further embodiment, the present invention relates to a compound of formula (I) as defined herein, wherein $R^1$ is 2-chlorophenyl and $R^2$ is selected from

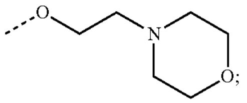
;
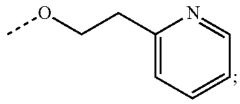
; or
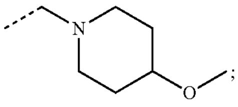
;

or or wherein $R^1$ is 2-chloro-4-fluorophenyl or 2-chloro-6-fluorophenyl and $R^2$ is

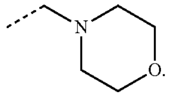

In an additional embodiment, the present invention relates to a compound of formula (I') as defined herein, wherein $R^1$ is phenyl or pyridinyl each optionally substituted with 1 or 2 substituents independently selected from the group consisting of halo, $(C_{3-6}$cycloalkyl$)C_{1-3}$alkyloxy and $C_{1-6}$alkyloxy; and $R^2$ is —$CH_2$—$NR^{3a}R^{4a}$;

wherein $R^{3a}$ is hydrogen or methyl;

$R^{4a}$ is selected from the group consisting of $C_{1-3}$alkyl; or $NR^{3a}R^{4a}$ is morpholinyl;

or a pharmaceutically acceptable salt or a solvate thereof.

In an additional embodiment, the invention relates to a compound of Formula (I'), as described herein, wherein $R^1$ is phenyl substituted with halo and $C_{1-6}$alkyloxy, or pyridinyl substituted with $C_{1-6}$alkyloxy or $(C_{3-6}$cycloalkyl$)C_{1-3}$alkyloxy; and $R^2$ is as previously defined;

or a pharmaceutically acceptable salt or a solvate thereof.

In a further embodiment, the invention relates to a compound of Formula (I'), as described herein, wherein $R^1$ is phenyl substituted with chloro and $C_{1-6}$alkyloxy, in particular ethoxy, isopropoxy or butoxy; or pyridinyl substituted with $C_{1-6}$alkyloxy or $(C_{3-6}$cycloalkyl$)C_{1-3}$alkyloxy, in particular butoxy or cyclopropylmethoxy; and $R^2$ is —$CH_2$—$NHCH_3$, —$CH_2$—$N(CH_3)_2$ or —$CH_2$-(4-morpholinyl);

or a pharmaceutically acceptable salt or a solvate thereof.

In an additional embodiment, the invention relates to a compound of Formula (I'), as described herein, wherein $R^1$ is phenyl substituted with halo and $C_{1-6}$alkyloxy, or pyridinyl substituted with $C_{1-6}$alkyloxy; and $R^2$ is as previously defined;

or a pharmaceutically acceptable salt or a solvate thereof.

In a further embodiment, the invention relates to a compound of Formula (I'), as described herein, wherein $R^1$ is phenyl substituted with chloro and $C_{1-6}$alkyloxy, in particular ethoxy, isopropoxy or butoxy; or pyridinyl substituted with $C_{1-6}$alkyloxy, in particular butoxy; and $R^2$ is as previously defined;

or a pharmaceutically acceptable salt or a solvate thereof.

In an additional embodiment of the present invention, the compound is selected from Ethyl 1-(2-chlorophenyl)-4-methyl[1,2,4]triazolo[4,3-a]quinoxaline-8-carboxylate;

Ethyl 1-(2-chlorophenyl)-4-methyl[1,2,4]triazolo[4,3-a]quinoxaline-7-carboxylate;

Ethyl 4-methyl-1-phenyl[1,2,4]triazolo[4,3-a]quinoxaline-8-carboxylate;

Ethyl 4-methyl-1-phenyl[1,2,4]triazolo[4,3-a]quinoxaline-7-carboxylate;

8-Bromo-1-(2-chlorophenyl)-4-methyl[1,2,4]triazolo[4,3-a]quinoxaline;

7-Bromo-1-(2-chlorophenyl)-4-methyl[1,2,4]triazolo[4,3-a]quinoxaline;

1-(2-Chlorophenyl)-4-methyl-8-(trifluoromethoxy)[1,2,4]triazolo[4,3-a]quinoxaline;

1-(2-Chlorophenyl)-4-methyl-7-(trifluoromethoxy)[1,2,4]triazolo[4,3-a]quinoxaline;

1-(2-Chlorophenyl)-8-methoxy-4-methyl[1,2,4]triazolo[4,3-a]quinoxaline;

8-Bromo-1-(5-butoxy-2-chlorophenyl)-4-methyl[1,2,4]triazolo[4,3-a]quinoxaline;

7-Bromo-1-(5-butoxy-2-chlorophenyl)-4-methyl[1,2,4]triazolo[4,3-a]quinoxaline;

8-Bromo-1-(5-butoxypyridin-3-yl)-4-methyl[1,2,4]triazolo[4,3-a]quinoxaline;

Benzyl 4-methyl-1-phenyl[1,2,4]triazolo[4,3-a]quinoxaline-8-carboxylate;

N-Benzyl-4-methyl-1-phenyl[1,2,4]triazolo[4,3-a]quinoxaline-8-carboxamide;

1-(2-Chlorophenyl)-N-ethyl-4-methyl[1,2,4]triazolo[4,3-a]quinoxaline-8-carboxamide;

1-(2,5-Dichlorophenyl)-4-methyl-N-(pyridin-2-ylmethyl)[1,2,4]triazolo[4,3-a]quinoxaline-8-carboxamide;

8-(Ethoxymethyl)-4-methyl-1-phenyl[1,2,4]triazolo[4,3-a]quinoxaline;

1-(2-Chlorophenyl)-4-methyl[1,2,4]triazolo[4,3-a]quinoxalin-8-ol;

1-(2-Chlorophenyl)-8-ethenyl-4-methyl[1,2,4]triazolo[4,3-a]quinoxaline;

1-(2-Chlorophenyl)-4-methyl-8-(2-pyridin-2-ylethoxy)[1,2,4]triazolo[4,3-a]quinoxaline;

1-(2-Chlorophenyl)-4-methyl-8-(4-methylpiperazin-1-yl)[1,2,4]triazolo[4,3-a]quinoxaline;

1-(5-Butoxypyridin-3-yl)-4-methyl-8-(morpholin-4-ylmethyl)[1,2,4]triazolo[4,3-a]quinoxaline, or a hydrochloride salt thereof, or an oxalate salt thereof;

1-(5-Butoxypyridin-3-yl)-4-methyl-8-[morpholin-4-yl($^3H_1$)methyl][1,2,4]triazolo[4,3-a]quinoxaline;

1-(5-Butoxy-2-chlorophenyl)-4-methyl-8-(morpholin-4-ylmethyl)[1,2,4]triazolo[4,3-a]quinoxaline or a hydrochloride salt thereof;

1-(2-Chlorophenyl)-4-methyl-8-(morpholin-4-ylmethyl)[1,2,4]triazolo[4,3-a]quinoxaline;

N-{[1-(2-Chlorophenyl)-4-methyl[1,2,4]triazolo[4,3-a]quinoxalin-8-yl]methyl}ethanamine;

1-[1-(2-Chlorophenyl)-4-methyl[1,2,4]triazolo[4,3-a]quinoxalin-8-yl]-2,2,2-trifluoroethanol;

1-(2-Chlorophenyl)-4-methyl-8-(2,2,2-trifluoro-1-morpholin-4-ylethyl)[1,2,4]triazolo[4,3-a]quinoxaline;

1-(2-Chloro-6-fluorophenyl)-4-methyl-8-(morpholin-4-ylmethyl)[1,2,4]triazolo[4,3-a]quinoxaline;

1-[2-Chloro-6-($^{18}F$)fluorophenyl]-4-methyl-8-(morpholin-4-ylmethyl)[1,2,4]triazolo[4,3-a]quinoxaline;

Cyclopropyl[4-methyl-1-(4-methylpyridin-3-yl)[1,2,4]triazolo[4,3-a]quinoxalin-8-yl]methanone;

1-(2-Chlorophenyl)-8-(1,1-difluoroethoxy)-4-methyl[1,2,4]triazolo[4,3-a]quinoxaline;

1-(5-Butoxy-2-chlorophenyl)-4-methyl-8-(4-methylpiperazin-1-yl)[1,2,4]triazolo[4,3-a]quinoxaline;

1-(2-Chlorophenyl)-4-methyl[1,2,4]triazolo[4,3-a]quinoxalin-8-amine;

N-[1-(2-Chlorophenyl)-4-methyl[1,2,4]triazolo[4,3-a]quinoxalin-8-yl]propanamide;

(4-Methyl-1-phenyl[1,2,4]triazolo[4,3-a]quinoxalin-8-yl)methanol;

1-(2-Chlorophenyl)-4-methyl-8-(pyridin-4-yloxy)[1,2,4]triazolo[4,3-a]quinoxaline;

1-(2-Chlorophenyl)-N-[(4-fluoropyridin-2-yl)methyl]-4-methyl[1,2,4]triazolo[4,3-a]quinoxaline-8-carboxamide;

1-(2-Chlorophenyl)-N-[(6-fluoropyridin-2-yl)methyl]-4-methyl[1,2,4]triazolo[4,3-a]quinoxaline-8-carboxamide;

1-(2,6-Dichlorophenyl)-N-ethyl-4-methyl[1,2,4]triazolo[4,3-a]quinoxaline-8-carboxamide;

N-Benzyl-1-(2-chlorophenyl)-4-methyl[1,2,4]triazolo[4,3-a]quinoxaline-8-carboxamide;

1-(2-Chlorophenyl)-4-methyl-N-(pyridin-2-ylmethyl)[1,2,4]triazolo[4,3-a]quinoxaline-8-carboxamide;

1-(2-Chlorophenyl)-4-methyl-N-(2-morpholin-4-ylethyl)[1,2,4]triazolo[4,3-a]quinoxaline-8-carboxamide;

1-(2-Chlorophenyl)-N-(2-methoxyethyl)-4-methyl[1,2,4]triazolo[4,3-a]quinoxaline-8-carboxamide;

1-(2-Chlorophenyl)-4-methyl-N-(2-phenylethyl)[1,2,4]triazolo[4,3-a]quinoxaline-8-carboxamide;

1-(2-Chloro-5-fluorophenyl)-4-methyl-N-(pyridin-2-ylmethyl)[1,2,4]triazolo[4,3-a]quinoxaline-8-carboxamide;

1-(2-Chlorophenyl)-N-(2-fluoroethyl)-4-methyl[1,2,4]triazolo[4,3-a]quinoxaline-8-carboxamide;

1-(2-Chlorophenyl)-N-[2-(diethylamino)ethyl]-4-methyl[1,2,4]triazolo[4,3-a]quinoxaline-8-carboxamide;

1-(2-Chlorophenyl)-N-(2-hydroxyethyl)-4-methyl[1,2,4]triazolo[4,3-a]quinoxaline-8-carboxamide;

1-(2-Chloro-5-methoxyphenyl)-4-methyl-N-(pyridin-2-ylmethyl)[1,2,4]triazolo[4,3-a]quinoxaline-8-carboxamide;

1-(2-Chloro-5-methylphenyl)-4-methyl-N-(pyridin-2-ylmethyl)[1,2,4]triazolo[4,3-a]quinoxaline-8-carboxamide;

1-(2-Chlorophenyl)-4-methyl-N-(2-piperidin-1-ylethyl)[1,2,4]triazolo[4,3-a]quinoxaline-8-carboxamide;

1-(2-Chlorophenyl)-N,4-dimethyl[1,2,4]triazolo[4,3-a]quinoxaline-8-carboxamide;

1-(2-Chlorophenyl)-4-methyl-N-(1-methylpiperidin-4-yl)[1,2,4]triazolo[4,3-a]quinoxaline-8-carboxamide;

1-(2-Chlorophenyl)-4-methyl-N-(2-pyrrolidin-1-ylethyl)[1,2,4]triazolo[4,3-a]quinoxaline-8-carboxamide;

1-(2-Chlorophenyl)-4-methyl-N-(3,4,5-trimethoxyphenyl)[1,2,4]triazolo[4,3-a]quinoxaline-8-carboxamide;

N-{[1-(2-Chlorophenyl)-4-methyl[1,2,4]triazolo[4,3-a]quinoxalin-8-yl]methyl}pyridin-3-amine;

N-Ethyl-1-(2-fluorophenyl)-4-methyl[1,2,4]triazolo[4,3-a]quinoxaline-8-carboxamide;

4-Methyl-1-phenyl-N-(pyridin-2-ylmethyl)[1,2,4]triazolo[4,3-a]quinoxaline-8-carboxamide;

1-(2-Methoxyphenyl)-4-methyl-N-(pyridin-2-ylmethyl)[1,2,4]triazolo[4,3-a]quinoxaline-8-carboxamide;

4-Methyl-1-phenyl-N-(2-phenylethyl)[1,2,4]triazolo[4,3-a]quinoxaline-8-carboxamide;

(4-{[1-(2-Chlorophenyl)-4-methyl[1,2,4]triazolo[4,3-a]quinoxalin-8-yl]methyl}morpholin-2-yl)methanol;

4-Methyl-1-phenyl-N-(pyridin-3-ylmethyl)[1,2,4]triazolo[4,3-a]quinoxaline-8-carboxamide;

1-{[1-(2-Chlorophenyl)-4-methyl[1,2,4]triazolo[4,3-a]quinoxalin-8-yl]methyl}pyrrolidin-3-ol;

1-[2-Chloro-5-(1-methylethoxy)phenyl]-4-methyl-8-(morpholin-4-ylmethyl)[1,2,4]triazolo[4,3-a]quinoxaline or a hydrochloride salt thereof;

1-(2-Chlorophenyl)-8-{[2-(fluoromethyl)morpholin-4-yl]methyl}-4-methyl[1,2,4]triazolo[4,3-a]quinoxaline;

1-(2-Chlorophenyl)-4-methyl-N-(2-pyridin-2-ylethyl)[1,2,4]triazolo[4,3-a]quinoxalin-8-amine;

1-(2-Chlorophenyl)-8-[(4-fluoropiperidin-1-yl)methyl]-4-methyl[1,2,4]triazolo[4,3-a]quinoxaline;

1-{[1-(2-Chlorophenyl)-4-methyl[1,2,4]triazolo[4,3-a]quinoxalin-8-yl]methyl}piperidin-3-ol;

2-(4-{[1-(2-Chlorophenyl)-4-methyl[1,2,4]triazolo[4,3-a]quinoxalin-8-yl]methyl}morpholin-2-yl)ethanol;

1-[1-(2-Chlorophenyl)-4-methyl[1,2,4]triazolo[4,3-a]quinoxalin-8-yl]-N-ethyl-2,2,2-trifluoroethanamine;

N-Ethyl-4-methyl-1-phenyl[1,2,4]triazolo[4,3-a]quinoxaline-8-carboxamide;

1-(2-Chlorophenyl)-4-methyl-N-(3,4,5-trimethoxybenzyl)[1,2,4]triazolo[4,3-a]quinoxaline-8-carboxamide;

1-(2-Chlorophenyl)-N-(2-methoxyethyl)-4-methyl[1,2,4]triazolo[4,3-a]quinoxalin-8-amine;

N-Ethyl-4-methyl-1-(2-methylpyridin-3-yl)[1,2,4]triazolo[4,3-a]quinoxaline-8-carboxamide;

8-Bromo-1-(2-chloro-5-methoxyphenyl)-4-methyl[1,2,4]triazolo[4,3-a]quinoxaline;

1-(2-Chloro-5-ethoxyphenyl)-4-methyl-8-(morpholin-4-ylmethyl)[1,2,4]triazolo[4,3-a]quinoxaline or a hydrochloride salt thereof;

1-(2-Chlorophenyl)-4-methyl-N-(2-morpholin-4-ylethyl)[1,2,4]triazolo[4,3-a]quinoxalin-8-amine;

1-(2-Chloro-5-propoxyphenyl)-4-methyl-8-(morpholin-4-ylmethyl)[1,2,4]triazolo[4,3-a]quinoxaline or a hydrochloride salt thereof;

1(2-Chlorophenyl)-4-methyl-8-[(4-methylpiperazin-1-yl)methyl][1,2,4]triazolo[4,3-a]quinoxaline;

1-(2-Chloro-4-methoxyphenyl)-4-methyl-N-(pyridin-2-ylmethyl)[1,2,4]triazolo[4,3-a]quinoxaline-8-carboxamide;

1(2-Chlorophenyl)-8-{[2-(methoxymethyl)morpholin-4-yl]methyl}-4-methyl[1,2,4]triazolo[4,3-a]quinoxaline or a hydrochloride salt thereof;

N-{[1-(2-Chlorophenyl)-4-methyl[1,2,4]triazolo[4,3-a]quinoxalin-8-yl]methyl}tetrahydro-2H-pyran-4-amine;

4-Methyl-1-phenyl-N-(3-phenylpropyl)[1,2,4]triazolo[4,3-a]quinoxaline-8-carboxamide;

N-Ethyl-1-(2-methoxyphenyl)-4-methyl[1,2,4]triazolo[4,3-a]quinoxaline-8-carboxamide;

1-(5-Butoxy-2-chlorophenyl)-4-methyl-8-(pyrrolidin-1-ylmethyl)[1,2,4]triazolo[4,3-a]quinoxaline or a hydrochloride salt thereof;

N-Ethyl-1-(5-methoxypyridin-3-yl)-4-methyl[1,2,4]triazolo[4,3-a]quinoxaline-8-carboxamide;

1-{[1-(2-Chlorophenyl)-4-methyl[1,2,4]triazolo[4,3-a]quinoxalin-8-yl]methyl}piperidin-4-ol;

1-(2-Chloro-4-fluorophenyl)-4-methyl-8-(morpholin-4-ylmethyl)[1,2,4]triazolo[4,3-a]quinoxaline;

4-Methyl-1-phenyl-N-(pyridin-4-ylmethyl)[1,2,4]triazolo[4,3-a]quinoxaline-8-carboxamide;

1-(2-Chloro-5-methoxyphenyl)-4-methyl-8-(morpholin-4-ylmethyl)[1,2,4]triazolo[4,3-a]quinoxaline;

8-Bromo-1-(2-chloro-5-ethoxyphenyl)-4-methyl[1,2,4]triazolo[4,3-a]quinoxaline;

1-(2-Chlorophenyl)-8-[(3-methoxypiperidin-1-yl)methyl]-4-methyl[1,2,4]triazolo[4,3-a]quinoxaline;

1-(2-Chlorophenyl)-N,N,4-trimethyl[1,2,4]triazolo[4,3-a]quinoxalin-8-amine;

1-[1-(5-Butoxy-2-chlorophenyl)-4-methyl[1,2,4]triazolo[4,3-a]quinoxalin-8-yl]-N,N-dimethylmethanamine;

1-(2-Chlorophenyl)-8-{[2-(2-fluoroethyl)morpholin-4-yl]methyl}-4-methyl[1,2,4]triazolo[4,3-a]quinoxaline;

trans-4-{[1-(2-Chlorophenyl)-4-methyl[1,2,4]triazolo[4,3-a]quinoxalin-8-yl]methyl}amino)cyclohexanol;

1-(5-Methoxypyridin-3-yl)-4-methyl-8-(morpholin-4-ylmethyl)[1,2,4]triazolo[4,3-a]quinoxaline;

8-Bromo-1-(2-chloro-5-propoxyphenyl)-4-methyl[1,2,4]triazolo[4,3-a]quinoxaline;

1-(2-Chlorophenyl)-8-[(4-methoxypiperidin-1-yl)methyl]-4-methyl[1,2,4]triazolo[4,3-a]quinoxaline;

1-(2-Chlorophenyl)-8-{[3-(methoxymethyl)pyrrolidin-1-yl]methyl}-4-methyl[1,2,4]triazolo[4,3-a]quinoxaline;

8-Bromo-1-(5-butoxy-2-fluorophenyl)-4-methyl[1,2,4]triazolo[4,3-a]quinoxaline;

1-(2-Chlorophenyl)-4-methyl[1,2,4]triazolo[4,3-a]quinoxaline;

1-(2-Chloro-5-methoxyphenyl)-8-[(4-fluoropiperidin-1-yl)methyl]-4-methyl[1,2,4]triazolo[4,3-a]quinoxaline;

4-Methyl-8-(phenoxymethyl)-1-phenyl[1,2,4]triazolo[4,3-a]quinoxaline;

N-Benzyl-1-[1-(2-chlorophenyl)-4-methyl[1,2,4]triazolo[4,3-a]quinoxalin-8-yl]methanamine;

8-Bromo-1-[2-chloro-5-(1-methylethoxy)phenyl]-4-methyl[1,2,4]triazolo[4,3-a]quinoxaline;

N-{[1-(5-Butoxy-2-chlorophenyl)-4-methyl[1,2,4]triazolo[4,3-a]quinoxalin-8-yl]methyl}ethanamine;

1-(2-Chloro-5-ethoxyphenyl)-4-methyl-8-(4-methylpiperazin-1-yl)[1,2,4]triazolo[4,3-a]quinoxaline;

N-{[1-(2-Chloro-5-ethoxyphenyl)-4-methyl[1,2,4]triazolo[4,3-a]quinoxalin-8-yl]methyl}pyridin-3-amine or a hydrochloride salt thereof;

N-Benzyl-N,4-dimethyl-1-phenyl[1,2,4]triazolo[4,3-a]quinoxaline-8-carboxamide;

1-{[1-(5-Butoxy-2-chlorophenyl)-4-methyl[1,2,4]triazolo[4,3-a]quinoxalin-8-yl]methyl}piperidin-4-ol;

1-(2-Chlorophenyl)-8-{[2-(2-methoxyethyl)morpholin-4-yl]methyl}-4-methyl[1,2,4]triazolo[4,3-a]quinoxaline;

1-[1-(2-Chlorophenyl)-4-methyl[1,2,4]triazolo[4,3-a]quinoxalin-8-yl]-N,N-dimethylmethanamine;

1-(2,4-Dichlorophenyl)-4-methyl-N-(pyridin-2-ylmethyl)[1,2,4]triazolo[4,3-a]quinoxaline-8-carboxamide;

N-Ethyl-4-methyl-1-(4-methylpyridin-3-yl)[1,2,4]triazolo[4,3-a]quinoxaline-8-carboxamide;

(1-{[1-(2-Chlorophenyl)-4-methyl[1,2,4]triazolo[4,3-a]quinoxalin-8-yl]methyl}piperidin-3-yl)methanol;

N-{[1-(2-Chloro-5-propoxyphenyl)-4-methyl[1,2,4]triazolo[4,3-a]quinoxalin-8-yl]methyl}ethanamine;

1-[1-(2-Chloro-5-propoxyphenyl)-4-methyl[1,2,4]triazolo[4,3-a]quinoxalin-8-yl]-N,N-dimethylmethanamine or a hydrochloride salt thereof;

1-(2-Chlorophenyl)-4-methyl-8-(2-morpholin-4-ylethoxy)[1,2,4]triazolo[4,3-a]quinoxaline;

1-(2-Chlorophenyl)-8-{[2-fluoro-2-(trifluoromethyl)morpholin-4-yl]methyl}-4-methyl[1,2,4]triazolo[4,3-a]quinoxaline;

1-[2-Chloro-5-(1-methylethoxy)phenyl]-4-methyl-8-(4-methylpiperazin-1-yl)[1,2,4]triazolo[4,3-a]quinoxaline;

1-(2-Chloro-5-propoxyphenyl)-4-methyl-8-(2-pyridin-3-ylethoxy)[1,2,4]triazolo[4,3-a]quinoxaline;

1-(2-Chloro-5-propoxyphenyl)-4-methyl-8-(4-methylpiperazin-1-yl)[1,2,4]triazolo[4,3-a]quinoxaline;

4-Methyl-1-(2-methylpyridin-3-yl)-8-(morpholin-4-ylmethyl)[1,2,4]triazolo[4,3-a]quinoxaline;

4-Methyl-8-(morpholin-4-ylmethyl)-1-(5-propoxypyridin-3-yl)[1,2,4]triazolo[4,3-a]quinoxaline or a hydrochloride salt thereof;

1-(5-Butoxy-2-fluorophenyl)-4-methyl[1,2,4]triazolo[4,3-a]quinoxaline-8-carbonitrile;

1-(2-Chloro-5-ethoxyphenyl)-4-methyl-8-(2-pyridin-3-ylethoxy)[1,2,4]triazolo[4,3-a]quinoxaline;

2-Phenylethyl 4-methyl-1-phenyl[1,2,4]triazolo[4,3-a]quinoxaline-8-carboxylate;

N-Ethyl-1-(2-methoxypyridin-3-yl)-4-methyl[1,2,4]triazolo[4,3-a]quinoxaline-8-carboxamide;

8-Bromo-1-(5-methoxypyridin-3-yl)-4-methyl[1,2,4]triazolo[4,3-a]quinoxaline;

8-Bromo-1-[5-(cyclopropylmethoxy)pyridin-3-yl]-4-methyl[1,2,4]triazolo[4,3-a]quinoxaline;

N-{[1-(5-Butoxy-2-chlorophenyl)-4-methyl[1,2,4]triazolo[4,3-a]quinoxalin-8-yl]methyl}cyclobutanamine;

N-Ethyl-4-methyl-1-pyridin-4-yl[1,2,4]triazolo[4,3-a]quinoxaline-8-carboxamide;

1-{[1-(2-Chloro-5-ethoxyphenyl)-4-methyl[1,2,4]triazolo[4,3-a]quinoxalin-8-yl]methyl}piperidin-4-ol;

1-{[1-(2-Chloro-5-propoxyphenyl)-4-methyl[1,2,4]triazolo[4,3-a]quinoxalin-8-yl]methyl}piperidin-4-ol;

1-(5-Butoxy-2-chlorophenyl)-4-methyl-8-(2-pyridin-3-ylethoxy)[1,2,4]triazolo[4,3-a]quinoxaline;

8-Bromo-4-methyl-1-(2-methylpyridin-3-yl)[1,2,4]triazolo[4,3-a]quinoxaline;

1-(5-Butoxy-2-chlorophenyl)-8-[(4-fluoropiperidin-1-yl)methyl]-4-methyl[1,2,4]triazolo[4,3-a]quinoxaline;

N-({1-[2-Chloro-5-(1-methylethoxy)phenyl]-4-methyl[1,2,4]triazolo[4,3-a]quinoxalin-8-yl}methyl)pyridin-3-amine or a hydrochloride salt thereof;

1-[2-Chloro-5-(1-methylethoxy)phenyl]-8-[(4-fluoropiperidin-1-yl)methyl]-4-methyl[1,2,4]triazolo[4,3-a]quinoxaline or a hydrochloride salt thereof;

1-(2-Chloro-5-propoxyphenyl)-8-[(4-fluoropiperidin-1-yl)methyl]-4-methyl[1,2,4]triazolo[4,3-a]quinoxaline;

1-({1-[2-Chloro-5-(1-methylethoxy)phenyl]-4-methyl[1,2,4]triazolo[4,3-a]quinoxalin-8-yl}methyl)piperidin-4-ol;

1-(2-Chloro-5-propoxyphenyl)-4-methyl-8-[(4-methylpiperazin-1-yl)methyl][1,2,4]triazolo[4,3-a]quinoxaline;

N-{[1-(2-Chloro-5-propoxyphenyl)-4-methyl[1,2,4]triazolo[4,3-a]quinoxalin-8-yl]methyl}pyridin-3-amine or a hydrochloride salt thereof;

1-(2-Chlorophenyl)-4-methyl-7-(2-pyridin-2-ylethoxy)[1,2,4]triazolo[4,3-a]quinoxaline;

1-(2-Chloro-5-ethoxyphenyl)-8-[(4-fluoropiperidin-1-yl)methyl]-4-methyl[1,2,4]triazolo[4,3-a]quinoxaline or a hydrochloride salt thereof;

1-{1-[2-Chloro-5-(1-methylethoxy)phenyl]-4-methyl[1,2,4]triazolo[4,3-a]quinoxalin-8-yl}-N,N-dimethylmethanamine;

1-[1-(2-Chloro-5-ethoxyphenyl)-4-methyl[1,2,4]triazolo[4,3-a]quinoxalin-8-yl]-N,N-dimethylmethanamine;

N-Ethyl-4-methyl-1-pyridin-3-yl[1,2,4]triazolo[4,3-a]quinoxaline-8-carboxamide;

[1-(2-Chlorophenyl)-4-methyl[1,2,4]triazolo[4,3-a]quinoxalin-8-yl](cyclopropyl)methanone;

1-(2-Chloro-5-ethoxyphenyl)-4-methyl-8-[(4-methylpiperazin-1-yl)methyl][1,2,4]triazolo[4,3-a]quinoxaline or a hydrochloride salt thereof;

1-[2-Chloro-5-(1-methylethoxy)phenyl]-4-methyl-8-(2-pyridin-3-ylethoxy)[1,2,4]triazolo[4,3-a]quinoxaline;

1-(2-Chlorophenyl)-4-methyl-N-(1-methylpiperidin-4-yl)[1,2,4]triazolo[4,3-a]quinoxalin-8-amine;

N-({1-[2-Chloro-5-(1-methylethoxy)phenyl]-4-methyl[1,2,4]triazolo[4,3-a]quinoxalin-8-yl}methyl)ethanamine or a hydrochloride salt thereof;

N-{[1-(5-Butoxy-2-chlorophenyl)-4-methyl[1,2,4]triazolo[4,3-a]quinoxalin-8-yl]methyl}propan-2-amine;

N-{[1-(5-Butoxypyridin-3-yl)-4-methyl[1,2,4]triazolo[4,3-a]quinoxalin-8-yl]methyl}ethanamine or a hydrochloride salt thereof;

N-{[1-(2-Chloro-5-ethoxyphenyl)-4-methyl[1,2,4]triazolo[4,3-a]quinoxalin-8-yl]methyl}ethanamine or a hydrochloride salt thereof;

1-[1-(5-Butoxy-2-chlorophenyl)-4-methyl[1,2,4]triazolo[4,3-a]quinoxalin-8-yl]-N-(cyclopropylmethyl)methanamine;

N-{[1-(5-Butoxypyridin-3-yl)-4-methyl[1,2,4]triazolo[4,3-a]quinoxalin-8-yl]methyl}propan-2-amine or a hydrochloride salt thereof;

8-Bromo-4-methyl-1-(5-methylpyridin-3-yl)[1,2,4]triazolo[4,3-a]quinoxaline;

N-{[1-(5-Butoxypyridin-3-yl)-4-methyl[1,2,4]triazolo[4,3-a]quinoxalin-8-yl]methyl}cyclobutanamine or a hydrochloride salt thereof;

1-[1-(5-Butoxypyridin-3-yl)-4-methyl[1,2,4]triazolo[4,3-a]quinoxalin-8-yl]-N-(cyclopropylmethyl)methanamine or a hydrochloride salt thereof;

1-{[1-(2-Chlorophenyl)-4-methyl[1,2,4]triazolo[4,3-a]quinoxalin-8-yl]methyl}-N,N-dimethylpiperidin-4-amine;

3-Phenylpropyl 4-methyl-1-phenyl[1,2,4]triazolo[4,3-a]quinoxaline-8-carboxylate;

8-Bromo-4-methyl-1-[2-(trifluoromethoxy)phenyl][1,2,4]triazolo[4,3-a]quinoxaline;

1-(5-Butoxy-2-chlorophenyl)-4-methyl-8-[(4-methylpiperazin-1-yl)methyl][1,2,4]triazolo[4,3-a]quinoxaline or a hydrochloride salt thereof;

1-(2-Chloro-5-propoxyphenyl)-4-methyl-8-[(2S)-pyrrolidin-2-ylmethoxy][1,2,4]triazolo[4,3-a]quinoxaline or a hydrochloride salt thereof;

4-Methyl-1-(5-methylpyridin-3-yl)-8-(trifluoromethyl)[1,2,4]triazolo[4,3-a]quinoxaline;

1-(5-Methoxypyridin-3-yl)-4-methyl-8-(trifluoromethyl)[1,2,4]triazolo[4,3-a]quinoxaline;

8-Methoxy-4-methyl-1-[2-(trifluoromethoxy)phenyl][1,2,4]triazolo[4,3-a]quinoxaline;

1-(5-Methoxypyridin-3-yl)-4-methyl-8-(trifluoromethoxy)[1,2,4]triazolo[4,3-a]quinoxaline;

8-Bromo-1-(2,3-dichlorophenyl)-4-methyl[1,2,4]triazolo[4,3-a]quinoxaline;

4-Methyl-1-(2-methylpyridin-3-yl)-8-(trifluoromethyl)[1,2,4]triazolo[4,3-a]quinoxaline;

4-Methyl-1-(2-methylpyridin-3-yl)-8-(trifluoromethoxy)[1,2,4]triazolo[4,3-a]quinoxaline;

N-Ethyl-4-methyl-1-(2-methylpyridin-3-yl)[1,2,4]triazolo[4,3-a]quinoxaline-7-carboxamide;

1-[2-Chloro-5-(1-methylethoxy)phenyl]-4-methyl-8-[(4-methylpiperazin-1-yl)methyl][1,2,4]triazolo[4,3-a]quinoxaline or a hydrochloride salt thereof;

8-Bromo-1-(5-chloropyridin-3-yl)-4-methyl[1,2,4]triazolo[4,3-a]quinoxaline;

N-Ethyl-1-(5-methoxypyridin-3-yl)-4-methyl[1,2,4]triazolo[4,3-a]quinoxaline-7-carboxamide;

8-Methoxy-4-methyl-1-(4-methylpyridin-3-yl)[1,2,4]triazolo[4,3-a]quinoxaline;

4-Methyl-1-(2-methylpyridin-3-yl)[1,2,4]triazolo[4,3-a]quinoxaline;

7-Bromo-1-(5-butoxy-2-fluorophenyl)-4-methyl[1,2,4]triazolo[4,3-a]quinoxaline;

1-(5-Butoxy-2-fluorophenyl)-4-methyl[1,2,4]triazolo[4,3-a]quinoxaline-7-carbonitrile;

4-Methyl-1-(5-methylpyridin-3-yl)[1,2,4]triazolo[4,3-a]quinoxaline;

N-{[4-Methyl-1-(5-propoxypyridin-3-yl)[1,2,4]triazolo[4,3-a]quinoxalin-8-yl]methyl}ethanamine or a hydrochloride salt thereof;

N-Benzyl-4-methyl-1-phenyl[1,2,4]triazolo[4,3-a]quinoxaline-7-carboxamide;

N-Ethyl-1-(2-methoxypyridin-3-yl)-4-methyl[1,2,4]triazolo[4,3-a]quinoxaline-7-carboxamide;

N-Ethyl-4-methyl-1-pyridin-2-yl[1,2,4]triazolo[4,3-a]quinoxaline-8-carboxamide;

N-Ethyl-4-methyl-1-(6-methylpyridin-3-yl)[1,2,4]triazolo[4,3-a]quinoxaline-8-carboxamide;

1-(5-Chloropyridin-3-yl)-4-methyl[1,2,4]triazolo[4,3-a]quinoxaline;

1-(2-Chlorophenyl)-4-methyl[1,2,4]triazolo[4,3-a]quinoxaline-8-carboxylic acid;

4-Methyl-1-phenyl[1,2,4]triazolo[4,3-a]quinoxaline-8-carboxylic acid;

8-Bromo-1-(2-chloro-6-fluorophenyl)-4-methyl[1,2,4]triazolo[4,3-a]quinoxaline;

1-(2-Chloro-6-fluorophenyl)-8-ethenyl-4-methyl[1,2,4]triazolo[4,3-a]quinoxaline;

8-Bromo-1-(2,5-dichlorophenyl)-4-methyl[1,2,4]triazolo[4,3-a]quinoxaline;

8-Bromo-4-methyl-1-(4-methylpyridin-3-yl)[1,2,4]triazolo[4,3-a]quinoxaline;

8-Ethenyl-4-methyl-1-(4-methylpyridin-3-yl)[1,2,4]triazolo[4,3-a]quinoxaline;

1-(5-Butoxypyridin-3-yl)-8-ethenyl-4-methyl[1,2,4]triazolo[4,3-a]quinoxaline;

1-[5-(2-Fluoroethoxy)pyridin-3-yl]-4-methyl-8-(morpholin-4-ylmethyl)[1,2,4]triazolo[4,3-a]quinoxaline;

1-[5-(Cyclopropylmethoxy)pyridin-3-yl]-8-[(4-fluoropiperidin-1-yl)methyl]-4-methyl[1,2,4]triazolo[4,3-a]quinoxaline or a hydrochloride salt thereof;

1-[5-(Cyclopropylmethoxy)pyridin-3-yl]-4-methyl-8-(morpholin-4-ylmethyl)[1,2,4]triazolo[4,3-a]quinoxaline or a hydrochloride salt thereof;

N-({1-[5-(Cyclopropylmethoxy)pyridin-3-yl]-4-methyl[1,2,4]triazolo[4,3-a]quinoxalin-8-yl}methyl)ethanamine or a hydrochloride salt thereof;

1-[1-(5-Butoxypyridin-3-yl)-4-methyl[1,2,4]triazolo[4,3-a]quinoxalin-8-yl]-N,N-dimethylmethanamine or a hydrochloride salt thereof;

1-(5-Butoxypyridin-3-yl)-4-methyl-8-(pyrrolidin-1-ylmethyl)[1,2,4]triazolo[4,3-a]quinoxaline or a hydrochloride salt thereof;

1-[1-(5-Butoxy-2-chlorophenyl)-4-methyl[1,2,4]triazolo[4,3-a]quinoxalin-8-yl]-N-methylmethanamine or a hydrochloride salt thereof;

1-[5-(Ethoxymethyl)pyridin-3-yl]-4-methyl-8-(morpholin-4-ylmethyl)[1,2,4]triazolo[4,3-a]quinoxaline or a hydrochloride salt thereof 1-{1-[5-(Cyclopropylmethoxy)pyridin-3-yl]-4-methyl[1,2,4]triazolo[4,3-a]quinoxalin-8-yl}-N,N-dimethylmethanamine or a hydrochloride salt thereof 1-[5-(Cyclopropylmethoxy)pyridin-3-yl]-4-methyl-8-(pyrrolidin-1-ylmethyl)[1,2,4]triazolo[4,3-a]quinoxaline or a hydrochloride salt thereof N-({1-[5-(Cyclopropylmethoxy)pyridin-3-yl]-4-methyl[1,2,4]triazolo[4,3-a]quinoxalin-8-yl}methyl)cyclobutanamine or a hydrochloride salt thereof N-({1-[5-(Cyclopropylmethoxy)pyridin-3-yl]-4-methyl[1,2,4]triazolo[4,3-a]quinoxalin-8-yl}methyl)propan-2-amine or a hydrochloride salt thereof N-{[4-Methyl-1-(5-propoxypyridin-3-yl)[1,2,4]triazolo[4,3-a]quinoxalin-8-yl]methyl}cyclobutanamine or a hydrochloride salt thereof 1-{1-[5-(Ethoxymethyl)pyridin-3-yl]-4-methyl[1,2,4]triazolo[4,3-a]quinoxalin-8-yl}-N,N-dimethylmethanamine or a hydrochloride salt thereof N-({1-[5-(Ethoxymethyl)pyridin-3-yl]-4-methyl[1,2,4]triazolo[4,3-a]quinoxalin-8-yl}methyl)cyclobutanamine or a hydrochloride salt thereof 1-[1-(5-Butoxypyridin-3-yl)-4-methyl[1,2,4]triazolo[4,3-a]quinoxalin-8-yl]-N-methylmethanamine or a hydrochloride salt thereof 1-[5-(2-Methoxyethoxy)pyridin-3-yl]-4-methyl-8-(morpholin-4-ylmethyl)[1,2,4]triazolo[4,3-a]quinoxaline;

1-(5-Butoxypyridin-3-yl)-8-[(4-fluoropiperidin-1-yl)methyl]-4-methyl[1,2,4]triazolo[4,3-a]quinoxaline or a hydrochloride salt thereof 1-[5-(2-Methoxyethyl)pyridin-3-yl]-4-methyl-8-(morpholin-4-ylmethyl)[1,2,4]triazolo[4,3-a]quinoxaline or a hydrochloride salt thereof 1-[5-(2-Methoxyethyl)pyridin-3-yl]-4-methyl-8-(morpholin-4-ylmethyl)[1,2,4]triazolo[4,3-a]quinoxaline or a hydrochloride salt thereof 1-[5-(3-Fluoropropoxy)pyridin-3-yl]-4-methyl-8-(morpholin-4-ylmethyl)[1,2,4]triazolo[4,3-a]quinoxaline;

1-[5-(3-Methoxypropyl)pyridin-3-yl]-4-methyl-8-(morpholin-4-ylmethyl)[1,2,4]triazolo[4,3-a]quinoxaline or a hydrochloride salt thereof and 1-(5-Butoxy-6-chloropyridin-3-yl)-4-methyl-8-(morpholin-4-ylmethyl)[1,2,4]triazolo[4,3-a]quinoxaline;

and the stereochemically isomeric forms thereof, the pharmaceutically acceptable salts and the solvates thereof.

In an additional embodiment of the present invention, the compound is selected from 1-(5-Butoxypyridin-3-yl)-4-methyl-8-(morpholin-4-ylmethyl)[1,2,4]triazolo[4,3-a]quinoxaline, or a hydrochloride salt thereof, or an oxalate salt thereof 1-[2-Chloro-5-(1-methylethoxy)phenyl]-4-methyl-8-(morpholin-4-ylmethyl)[1,2,4]triazolo[4,3-a]quinoxaline or a hydrochloride salt thereof;

1-[1-(5-Butoxy-2-chlorophenyl)-4-methyl[1,2,4]triazolo[4,3-a]quinoxalin-8-yl]-N,N-dimethylmethanamine;

1-[5-(Cyclopropylmethoxy)pyridin-3-yl]-4-methyl-8-(morpholin-4-ylmethyl)[1,2,4]triazolo[4,3-a]quinoxaline or a hydrochloride salt thereof; and 1-[1-(5-Butoxypyridin-3-yl)-4-methyl[1,2,4]triazolo[4,3-a]quinoxalin-8-yl]-N,N-dimethylmethanamine or a hydrochloride salt thereof;

and the stereochemically isomeric forms thereof, the pharmaceutically acceptable salts and the solvates thereof.

In an additional embodiment of the present invention, the compound is selected from 1-(2-Chlorophenyl)-4-methyl-8-(2-pyridin-2-ylethoxy)[1,2,4]triazolo[4,3-a]quinoxaline;

1-(2-Chloro-6-fluorophenyl)-4-methyl-8-(morpholin-4-ylmethyl) [1,2,4]triazolo[4,3-a]quinoxaline;

1-(2-Chloro-4-fluorophenyl)-4-methyl-8-(morpholin-4-ylmethyl) [1,2,4]triazolo[4,3-a]quinoxaline;

1-(2-Chlorophenyl)-8-[(4-methoxypiperidin-1-yl)methyl]-4-methyl[1,2,4]triazolo[4,3-a]quinoxaline; and 1-(2-Chlorophenyl)-4-methyl-8-(2-morpholin-4-ylethoxy)[1,2,4]triazolo[4,3-a]quinoxaline;

and the stereochemically isomeric forms thereof, the pharmaceutically acceptable salts and the solvates thereof.

As already stated, the invention also relates to radiolabelled compounds of Formula (I). In a particular embodiment, the invention relates to a compound of Formula (I-u)

(I-u)

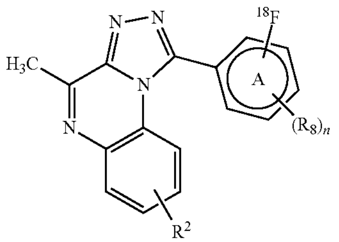

wherein ring A is phenyl or pyridinyl, $R^8$ is halo or trifluoromethyl, n is 0 or 1 and $R^2$ is as defined herein in the compounds of Formula (I);

or of Formula $[^3H]$-(I-p)

$[^3H]$-(I-p)

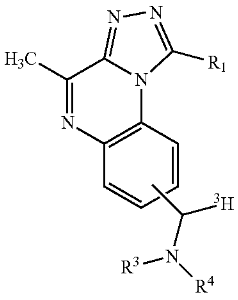

wherein $R^1$, $R^3$ and $R^4$, are as defined herein in the compounds of Formula (I);

or a pharmaceutically acceptable salt or a solvate thereof.

In an additional embodiment, the radiolabelled compound of Formula (I) is 1-(5-Butoxypyridin-3-yl)-4-methyl-8-[morpholin-4-yl($^3H_1$)methyl][1,2,4]triazolo[4,3-a]quinoxaline; or 1-[2-Chloro-6-($^{18}F$)fluorophenyl]-4-methyl-8-(morpholin-4-ylmethyl)[1,2,4]triazolo[4,3-a]quinoxaline;

or a pharmaceutically acceptable salt or a solvate thereof.

In an additional embodiment, the invention relates to an intermediate compound having the Formula (XVI)

(XVI)

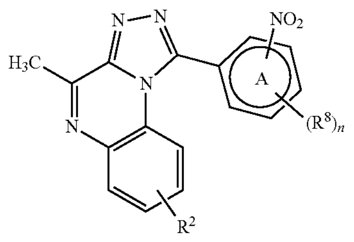

wherein ring A is phenyl or pyridinyl, $R^8$ is halo or trifluoromethyl, n is 0 or 1 and $R^2$ is as defined herein in the compounds of Formula (I);

or having the Formula (XIII)

(XIII)

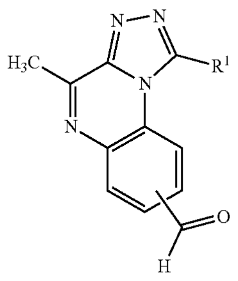

wherein $R^1$ is as defined herein in the compounds of Formula (I);

which may be used for the synthesis of the compound of Formula $[^3H]$-(I-p) or (I-u), respectively.

The compounds of Formula $[^3H]$-(I-p) or (I-u) and compositions comprising the compounds of Formula $[^3H]$-(I-p) or (I-u) can be used for imaging a tissue, cells or a host, in vitro or in vivo. In particular, the invention relates to a method of imaging or quantifying the PDE2 enzyme in a tissue, cells or a host in vitro or in vivo.

The cells and tissues are preferably central nervous system cells and tissues in which the PDE2 enzyme is abundant. As already mentioned, the PDE2 enzyme is abundant in central nervous system tissue, more in particular, in central nervous system tissue forming the brain; more in particular, PDE2 is expressed in olfactory bulb, olfactory tubercle, cortex, striatum, hippocampus, habenula, amygdala, thalamus, hypothalamus and substantia nigra.

When the method is performed in vivo, the host is a mammal. In such particular cases, the compound of Formula (I) is administered intravenously, for example, by injection with a syringe or by means of a peripheral intravenous line, such as a short catheter.

When the host is a human, the compound of Formula (I-u) or a sterile solution comprising a compound of Formula (I-u), may in particular be administered by intravenous administration in the arm, into any identifiable vein, in particular in the back of the hand, or in the median cubital vein at the elbow.

Thus, in a particular embodiment, the invention relates to a method of imaging a tissue or cells in a mammal, comprising the intravenous administration of a compound of Formula (I-u), as defined herein, or a composition comprising a compound of Formula (I-u) to the mammal, and imaging the tissue or cells with a positron-emission tomography imaging system.

Thus, in a further particular embodiment, the invention relates to a method of imaging a tissue or cells in a human, comprising the intravenous administration of a compound of Formula (I-u), as defined herein, or a sterile formulation comprising a compound of Formula (I-u) to the human, and imaging the tissue or cells with a positron-emission tomography imaging system.

In a further embodiment, the invention relates to a method of imaging or quantifying the PDE2 enzyme in a mammal, comprising the intravenous administration of a compound of Formula (I-u), or a composition comprising a compound of Formula (I-u) to the mammal, and imaging with a positron-emission tomography imaging system.

In another embodiment, the invention relates to the use of a compound of Formula (I-u) for imaging a tissue, cells or a host, in vitro or in vivo, or the invention relates to a compound of Formula (I-u), for use in imaging a tissue, cells or a host in vitro or in vivo, using positron-emission tomography.

Definitions

"Halo" shall denote fluoro, chloro and bromo; "$C_{1-6}$alkyl" and "$C_{1-3}$alkyl" as used herein as a group or part of a group shall denote a straight or branched saturated alkyl group having 1, 2, 3, 4, 5, or 6 carbon atoms or 1, 2 or 3 carbon atoms, respectively e.g. methyl, ethyl, 1-propyl, 2-propyl, 1-butyl, 2-butyl, 2-methylpropyl, tert-butyl, 1-pentyl, 2-methylbutyl, pentan-2-yl, 2-methylbutan-2-yl or hexyl and the like; "$C_{2-6}$alkenyl" as used herein as a group or part of a group refers to a linear or branched hydrocarbon group containing from 2 to 6 carbon atoms and containing a carbon carbon double bond; "$C_{1-6}$alkyloxy" and "$C_{1-3}$alkyloxy" shall denote an ether radical wherein $C_{1-6}$alkyl and $C_{1-3}$alkyl are as defined before; "halo$C_{1-3}$alkyl" shall denote $C_{1-3}$alkyl as defined before, substituted with 1 halo atom as defined before; "$C_{3-6}$cycloalkyl" shall denote cyclopropyl, cyclobutyl, cyclopentyl and cyclohexyl; "$C_{3-6}$cycloalkanediyl" shall denote a bivalent radical such as cyclopropanediyl, cyclobutanediyl, cyclopentanediyl and cyclohexanediyl; "($C_{3-6}$cycloalkyl)$C_{1-3}$alkyl" shall denote a $C_{3-6}$cycloalkyl as defined before, bound to the rest of the molecule through a $C_{1-3}$alkyl radical as defined before.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The term "host" refers to a mammal, in particular to humans, mice, dogs and rats.

The term "cell" refers to a cell expressing or incorporating the PDE2 enzyme.

It will be appreciated that some of the compounds of Formula (I) and their pharmaceutically acceptable addition salts and solvates thereof may contain one or more centres of chirality and exist as stereoisomeric forms.

The term "compounds of the invention" as used herein, is meant to include the compounds of Formula (I), and the salts and solvates thereof.

As used herein, any chemical formula with bonds shown only as solid lines and not as solid wedged or hashed wedged bonds, or otherwise indicated as having a particular configuration (e.g. R, 5) around one or more atoms, contemplates each possible stereoisomer, or mixture of two or more stereoisomers.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. If a compound contains an at least disubstituted non-aromatic cyclic group, the substituents may be in the cis or trans configuration.

Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system.

The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention.

It follows that a single compound may exist in both stereoisomeric and tautomeric form.

In addition, some of the compounds of the present invention may form solvates with water (i.e., hydrates) or common organic solvents, and such solvates are also intended to be encompassed within the scope of this invention.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^{3}H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{3}H$, $^{11}C$ and $^{18}F$.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluene-sulfonic acid, trifluoromethylsulfonic acid, and undecylenic acid. Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylene-diamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The names of the compounds of the present invention were generated according to the nomenclature rules agreed upon by the International Union of Pure and Applied Chemistry (IUPAC) using Advanced Chemical Development, Inc., software (ACD/Name product version 10.01.0.14105, October 2006).

Preparation of the Compounds

The compounds according to the invention can generally be prepared by a succession of steps, each of which is known to the skilled person. The transformations of different functional groups present in the final compounds into other functional groups according to Formula (I) can be performed as well by synthesis methods well known to the person skilled in the art. In particular, the compounds can be prepared according to the following synthesis methods.

Preparation of the Final Compounds

Compounds of Formula (I) can be prepared by synthesis methods well known to the person skilled in the art. Compounds of the invention may be prepared, for example, by nine different general schemes:

Scheme 1: Synthesis of compounds of Formula (I) when $R^2$ = hydrogen, halo, trifluoromethyl, trifluoromethoxy, cyano, —$L^2$—O—$R^5$ (where $L^2$ = covalent bond or C(═O); $R^5$ = $C_{1-3}$alkyl)

Method A:

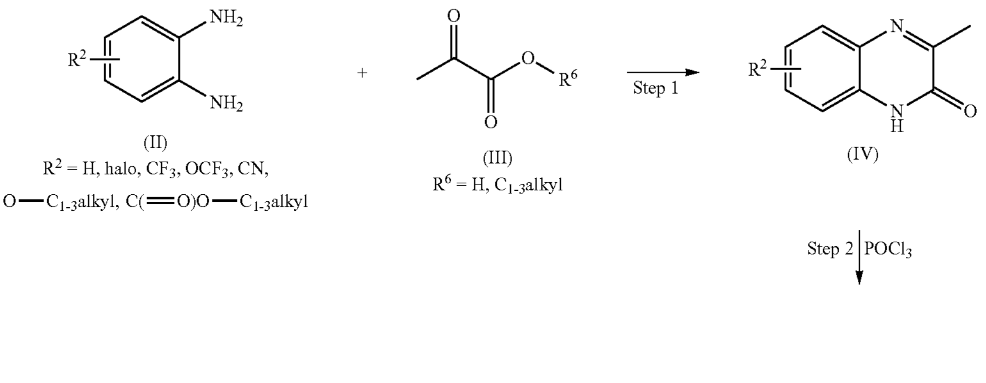

(II)
$R^2$ = H, halo, $CF_3$, $OCF_3$, CN, O—$C_{1-3}$alkyl, C(═O)O—$C_{1-3}$alkyl (III)
$R^6$ = H, $C_{1-3}$alkyl (IV)

-continued

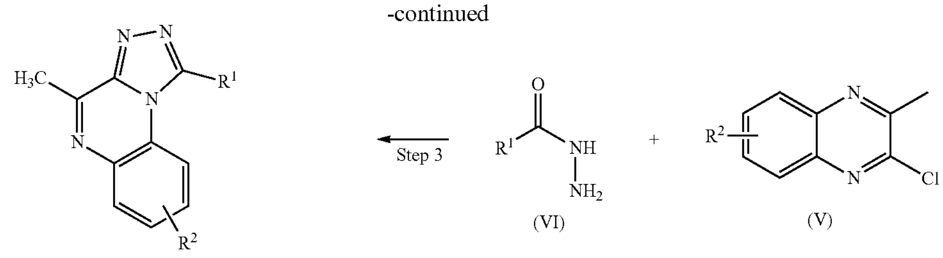

(I) (VI) (V)

$R^2$ = H (I-a), halo (I-b), $CF_3$ (I-c), $OCF_3$ (I-d), CN (I-e), O—$C_{1-3}$alkyl (I-f), C(=O)O—$C_{1-3}$alkyl (I-g)

Step 1: An intermediate compound of Formula (II) can be reacted with a commercially available compound of Formula (III), wherein $R^6$ is $C_{1-3}$-alkyl such as for example methyl or ethyl in an inert solvent such as, for example, toluene stirring the reaction mixture at a suitable temperature, typically at 100-130° C., using conventional heating or under microwave irradiation, for the required time to achieve completion of the reaction, typically 3 hours for conventional heating. When $R^6$ is hydrogen the reaction is performed in a mixture of acetic acid and water and the stirring is performed at room temperature overnight. This reaction usually affords a mixture of the two possible regioisomers of Formula (IV), which can be separated at this step or in one of the following steps by chromatographic methods, either by column chromatography or HPLC. Compounds of Formula (II) are either commercially available or described in chemical literature and can be prepared by simple standard synthetic procedures well known to the skilled person.

Step 2: Intermediate compounds of Formula (IV) can react, in presence or absence of a solvent such as for example 1,2-dichloroethane, with phosphorous oxychloride, stirring the reaction mixture at a suitable temperature, typically at 100-120° C., using conventional heating or under microwave irradiation, for the required time to achieve completion of the reaction, typically 2-4 hours for conventional heating. This reaction step affords intermediate compounds of Formula (V).

Step 3: An intermediate compound of Formula (V) can react with an intermediate compound of Formula (VI) in a solvent, such as, for example, ethanol, n-butanol or tetrahydrofuran stirring the reaction mixture at a suitable temperature, typically at 100-160° C., using conventional heating or under microwave irradiation, for the required time to achieve completion of the reaction, typically 15-20 minutes at 160° C. for microwave heating, affording final compounds of Formula (I). The intermediate compounds of Formula (VI) can be either commercially available or are described in chemical literature and can be prepared by simple standard synthetic procedures well known to the skilled person.

Method B:

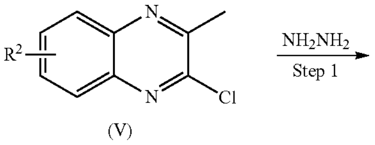

(V)

-continued

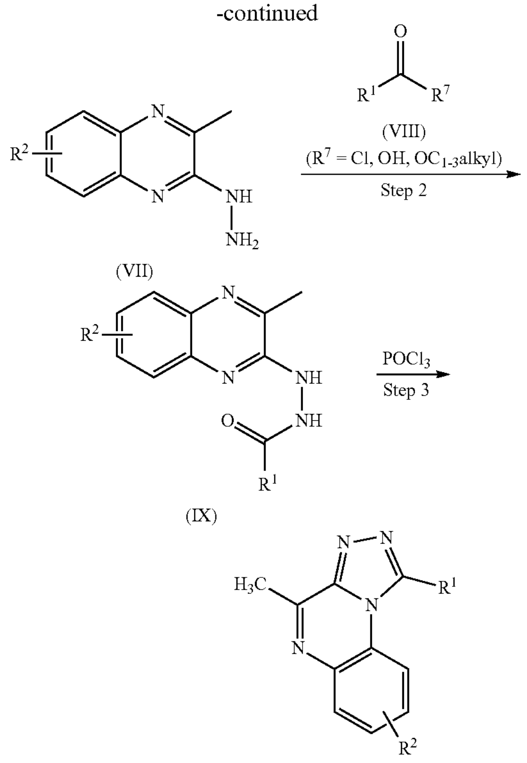

(VII) (IX)

$R^2$ = H (I-a), halo (I-b), $CF_3$ (I-c), $OCF_3$ (I-d), CN (I-e), O—$C_{1-3}$alkyl (I-f), C(=O)O—$C_{1-3}$alkyl (I-g)

Step 1: Intermediate compounds of Formula (V) can be treated with hydrazine hydrate in an inert solvent, such as methanol or ethanol, following simple standard synthetic procedures well known to the skilled person yielding intermediate compounds of Formula (VII).

Step 2: Intermediate compounds of Formula (VII) can react with intermediate compounds of Formula (VIII) following simple standard synthetic procedures well known to the skilled person to give intermediate compounds of Formula (IX). Intermediate compounds of formula (VIII) can be either commercially available or synthesized following literature precedents.

Step 3: Intermediate compounds of Formula (IX) can react, in presence or absence of a solvent such as for example 1,2-dichloroethane, with phosphorous oxychloride, stirring the reaction mixture at a suitable temperature, typically at 80-100° C., using conventional heating or under microwave irradiation, for the required time to achieve completion of the reaction, typically 16 hours for conventional heating. This reaction step affords compounds of Formula (I).

Scheme 2: Synthesis of compounds of Formula (I) when $R^2$ = —$L^2$—O—$R^5$ (where $L^2$ = C(═O); $R^5$ ≠ $C_{1-3}$alkyl)

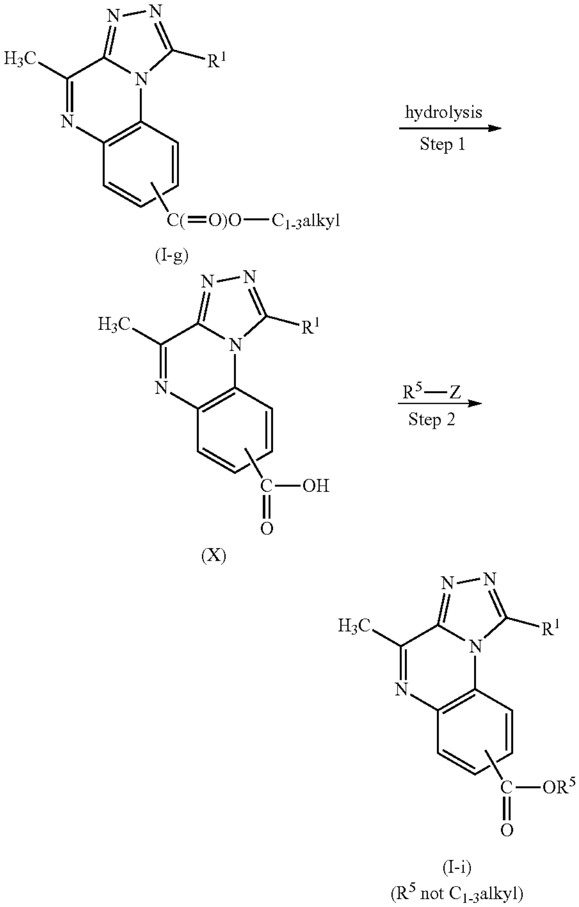

(I-g)

(X)

(I-i)
($R^5$ not $C_{1-3}$alkyl)

Step 1: Final compounds of Formula (I-g) may be used as starting materials for a conventional hydrolysis reaction very well known to the person skilled in the art. Thus, compounds of Formula (I-g) can react in presence of a base, such as for example sodium or potassium hydroxide, in a mixture of solvents such as, for example, tetrahydrofuran and water stirring the reaction mixture at a suitable temperature, typically room temperature, for the required time to achieve completion of the reaction, typically 18 hours. This reaction step affords intermediate compounds of Formula (X).

Step 2: Intermediate compounds of Formula (X) can react with an alkylating agent, of formula $R^5$—Z, wherein $R^5$ is selected from the group consisting of $C_{1-3}$alkyl; $C_{1-3}$alkyl substituted with pyridinyl, phenyl or morpholinyl; and pyridinyl and Z is a suitable leaving group such as halo, for example bromo or iodo, in the presence of a suitable base such as 1,8-diazabicyclo[5.4.0]undec-7-ene (DBU), in an inert solvent such as, for example, dimethylformamide, stirring the reaction mixture at a suitable temperature, typically room temperature, for the required time to achieve completion of the reaction, typically 2-3 hours. This reaction step affords final compounds of Formula (I-i).

Scheme 3: Synthesis of compounds of Formula (I) when $R^2$ = —$L^1$—$NR^3R^4$ [where $L^1$ = C(═O)]

Method A:

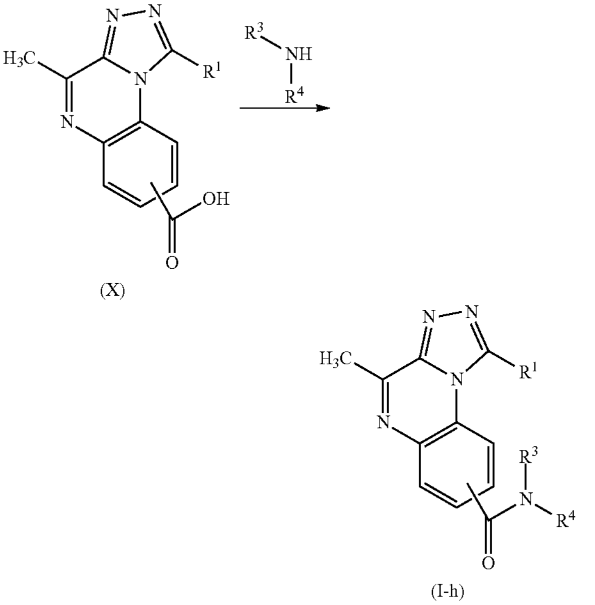

(X)

(I-h)

Intermediate compounds of formula (X) can react with an amine of formula $NHR^3R^4$, wherein $R^3$ and $R^4$ are as previously defined, in the presence of a coupling reagent, such as for example 2-(7-aza-1H-benzotriazole-1-yl)-1,1,3,3-tetramethyluronium hexafluorophosphate (HATU) and a base such as N,N-diisopropyl ethylamine, in a mixture of inert solvents such as, for example, N,N-dimethylformamide and dichloromethane, stirring the reaction mixture at a suitable temperature, typically room temperature, for the required time to achieve completion of the reaction, typically 2-3 hours. This reaction step affords final compounds of Formula (I-h).

Method B:

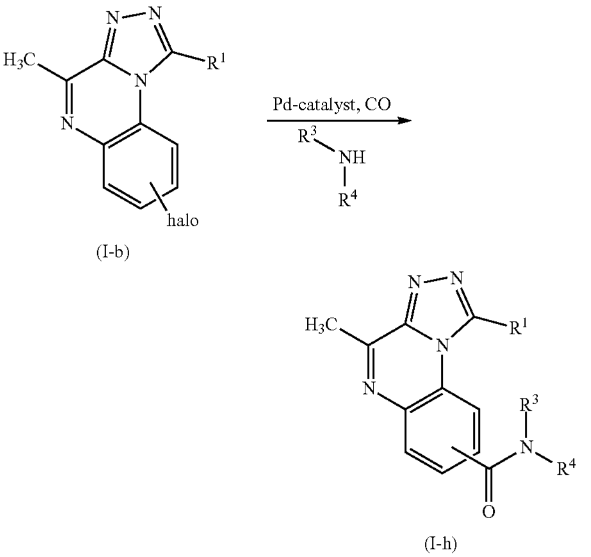

(I-b)

(I-h)

Final compounds of Formula (I-b) may react with an amine of formula $NHR^3R^4$, wherein $R^3$ and $R^4$ are as previously defined, in an inert solvent, such as, for example, toluene in presence of a complexing agent, such as for example XantPhos, a palladium catalyst, such as Palladium (II) acetate, a base such as for example triethylamine, and carbon monoxide. The reaction is closed in an autoclave system and is stirred at a suitable temperature, such as 150-160° C., using conventional heating, for the required time to achieve completion of the reaction, typically 16 hours.

Scheme 4: Synthesis of compounds of Formula (I) when $R^2$ = —$L^2$—O—$R^5$ and $L^2$ = $CH_2$

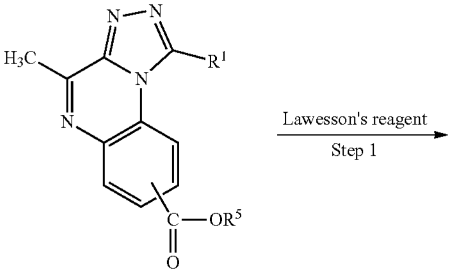

(I-g) or (I-i)

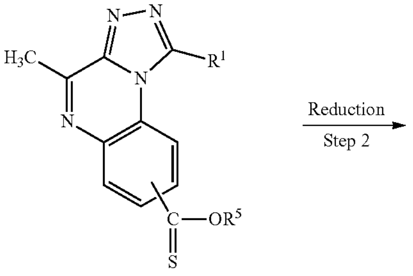

(XI)

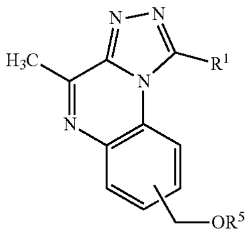

(I-j)

Step 1: Final compounds of Formula (I-g) or (I-i) may react with the Lawesson's reagent (2,4-bis-(4-methoxyphenyl)-1,3-dithia-2,4-diphosphetane 2,4-disulfide), in an inert solvent such as, for example, toluene and stirring the reaction mixture at a suitable temperature, typically 150° C., for the required time to achieve completion of the reaction, typically 24 hours. This reaction step affords intermediate compounds of Formula (XI).

Step 2: Intermediate compounds of Formula (XI) can react in an inert solvent such as, for example, tetrahydrofuran in presence of Raney®-Nickel, stirring the reaction mixture at a suitable temperature, such as room temperature, for the required time to achieve completion of the reaction, typically 1 hour. This reaction step affords final compounds of Formula (I-j).

Scheme 5: Synthesis of compounds of Formula (I) when $R^2$ = —$L^2$—O—$R^5$ and $L^2$ = covalent bond

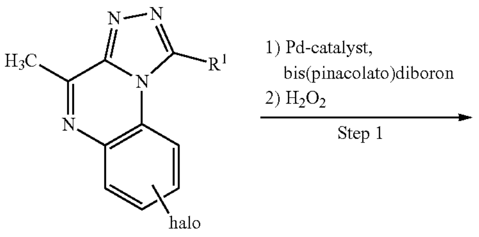

(I-b)

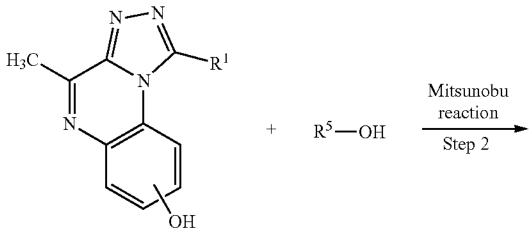

(I-k)

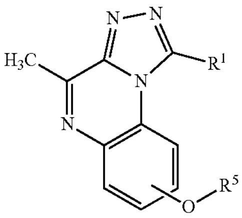

(I-l)

Step 1: Final compounds of Formula (I-b) may be also used as precursors for a hydroxylation reaction. Thus, a compound of Formula (I-b) can react with bis-(pinacolato) diboron in an inert solvent such as, for example, 1,4-dioxane in presence of a palladium catalyst, such as [1,1'-Bis(diphenylphosphino)ferrocene]dichloro-palladium (II), a base such as for example potassium acetate, stirring the reaction mixture at a suitable temperature, such as 110-130° C., for the required time to consume all starting material, typically 1 hour. Then to that mixture cooled down to 0° C. a mixture of $H_2O_2$ and acetic acid can be added and the reaction can be stirred at a suitable temperature, such as room temperature, for the required time to achieve completion of the reaction, typically 45-60 minutes. This reaction step affords compounds of Formula (I-k).

Step 2: Compounds of Formula (I-k) may be used as intermediate reagents for a conventional Mitsunobu reaction, which is well known to the person skilled in the art. Thus, a compound of Formula (I-k) can react with alcohols of formula $R^5$—OH, wherein $R^5$ is selected from the group consisting of $C_{1-3}$alkyl; $C_{1-3}$alkyl substituted with pyridinyl, phenyl or morpholinyl; and pyridinyl and in the presence of diethyl-, di-tert-butyl- or diisopropyl azodicarboxylate and triphenylphosphine, in an inert solvent such as for example tetrahydrofuran, stirring the reaction mixture at a suitable temperature, typically at 120° C. under microwave irradiation, for a suitable period of time to allow completion of the reaction, typically 15-20 minutes. This reaction step affords final compound of Formula (I-l).

Scheme 6: Synthesis of compounds of Formula (I) when $R^2$ = —$L^2$—$NR^3R^4$ and $L^1$ = covalent bond

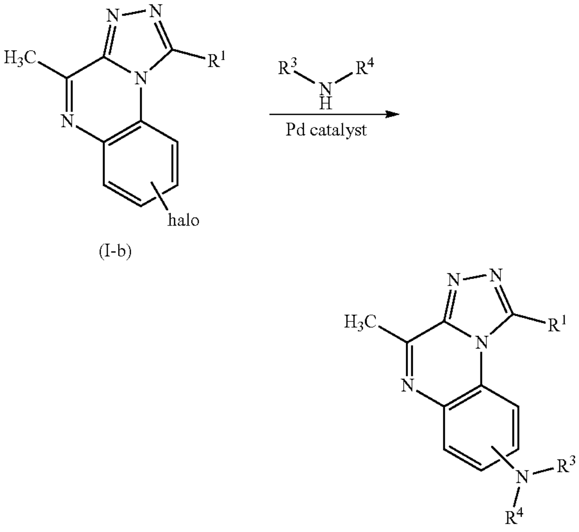

(I-b)

(I-m)

A compound of Formula (I-b) can react with an amine of formula $NHR^3R^4$, wherein $R^3$ and $R^4$ are as previously defined, in an inert solvent, such as, for example, toluene or a mixture of 1,4-dioxane/water, in presence of a complexing agent, such as 4,5-bis-(diphenylphosphino)-9,9-dimethylxanthene (XantPhos) or 2-dichlorohexylphosphino-2',4',6'-triisopropylbiphenyl (XPhos), a palladium catalyst, such as Palladium(II) acetate or tris(dibenzylideneacetone)dipalladium(0), and a base such as for example caesium carbonate, stirring the reaction mixture at a suitable temperature, such as 110-130° C., using conventional heating or microwave irradiation, for the required time to achieve completion of the reaction, typically 10-15 minutes for microwave heating. This reaction step yields final compound of Formula (I-m).

Scheme 7: Synthesis of compounds of Formula (I) when $R^2$ = —$L^2$—$NR^3R^4$ and $L^1$ = $CH_2$ or $CH(CF_3)$ Method A:

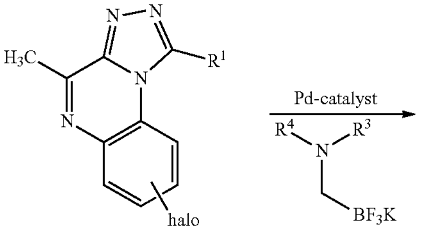

(I-b) (XII)

-continued

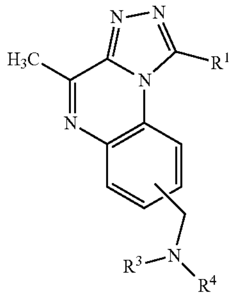

(I-n)

A compound of Formula (I-b) can also react with an intermediate compound of Formula (XII) in an inert solvent or mixture of solvents, such as, for example, a mixture of tetrahydrofuran and water in presence of a complexing agent such as 2-dichlorohexylphosphino-2',4',6'-triisopropylbiphenyl (XPhos), a palladium catalyst, such as Palladium (II) acetate, and a base such as for example caesium carbonate stirring the reaction mixture at a suitable temperature, such as 110-120° C., using conventional heating or microwave irradiation, for the required time to achieve completion of the reaction, typically 45 minutes for conventional heating. Intermediate compounds of Formula (XII) can be either commercially available or can be prepared by methods described in chemical literature well known to the skilled person.

Method B:

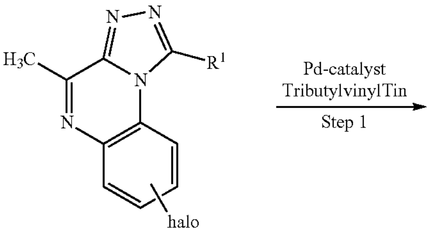

(I-b)

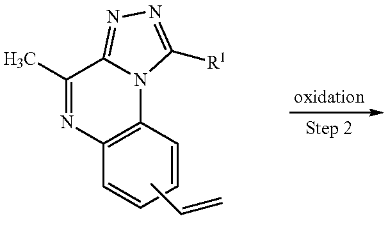

(I-o)

-continued

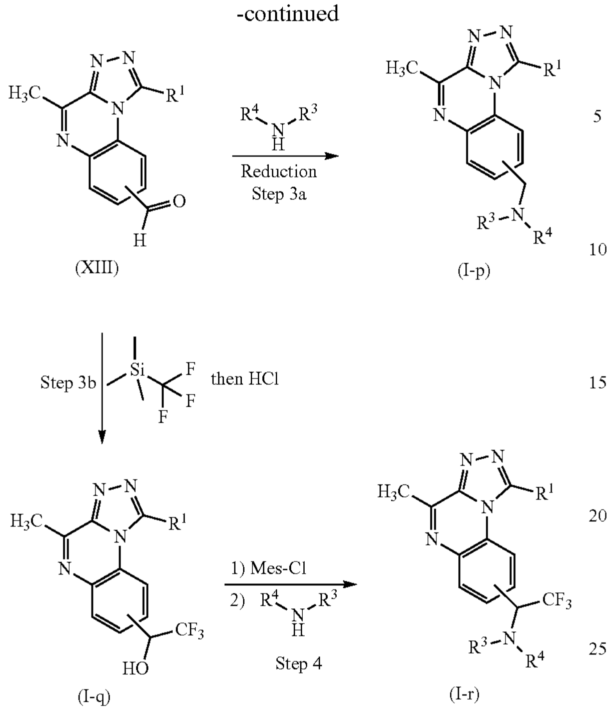

(XIII) (I-p) (I-q) (I-r)

Step 1: Final compounds of Formula (I-b) may also be used as precursors for the synthesis of final compounds of Formula (I-o), Formula (I-p), Formula (I-q) and Formula (I-r). Thus, a compound of Formula (I-b) can react with tributylvinyl tin, in an inert solvent such as, for example, toluene in presence of a palladium catalyst, such as (triphenylphosphine)tetrakis Palladium(0), and a salt such as, for example, lithium chloride stirring the reaction mixture at a suitable temperature, such as 120-130° C., using conventional heating or microwave irradiation, for the required time to achieve completion of the reaction, typically 1 hour for conventional heating. This reaction step affords a final compound of Formula (I-o).

Step 2: A compound of Formula (I-o) can be oxidized by standard procedures well known to the person skilled in the art, such as, for example, by ozonolysis or by reaction with a mixture of osmium tetroxide and sodium periodate yielding an intermediate compound of Formula (XIII).

Step 3a: An intermediate compound of Formula (XIII) can react with an amine of formula $NHR^3R^4$, wherein $R^3$ and $R^4$ are as previously defined, in a conventional reductive amination reaction, which is well known to the skilled person. Thus, a compound of Formula (XIII) can react with an amine of formula $NHR^3R^4$ as previously defined in an inert solvent, such as for example, 1,2-dichloroetane, stirring the reaction mixture at a suitable temperature, typically at 80-120° C. for 10-20 minutes under microwave irradiation, in the presence of a reducing agent, such as tributoxy cyanoborohydride or sodium borohydride. After the addition of the reducing agent the reaction can be stirred either at room temperature or by microwave heating for the required time to achieve completion of the reaction, typically 20 min at 80° C. for microwave heating. This reaction step yields a final compound of Formula (I-p).

Step 3b: An intermediate compound of Formula (XIII) can also react with trimethyl(trifluoromethyl) silane in a inert solvent, such as, for example, dimethoxyethane in the presence of a catalytic amount of cesium fluoride stirring the reaction mixture at a suitable temperature, typically room temperature for the required time to consume all starting material, typically 30 minutes. After that, the mixture can be treated with an acidic solution, such as for example, hydrochloric acid stirring the reaction at a suitable temperature, typically room temperature for the required time to achieve completion of the reaction, typically 15 minutes. This reaction step gives a compound of Formula (I-q).

Step 4: A final compound of formula (I-q) can react with methanesulfonyl chloride in an inert solvent, such as, for example, dichlorometane in the presence of a base, such as pyridine, stirring the reaction at a suitable temperature, typically room temperature for the required time to consume all starting material, typically overnight. Then, the mixture can be reacted with a primary or secondary amine stirring the reaction at a suitable temperature, typically room temperature for the required time to achieve completion of the reaction, typically 4 hours. This reaction step affords a final compound of Formula (I-r).

Scheme 8: Synthesis of compounds of Formula (I) when $R^2$ = ($C_{3-6}$cycloalkyl)carbonyl

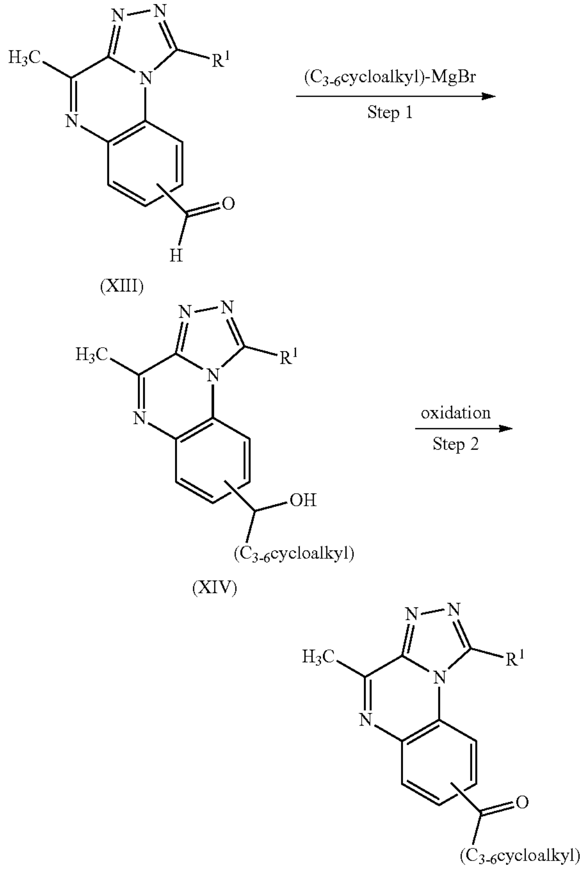

(XIII) (XIV) (I-s)

Step 1: Intermediate compounds of Formula (XIII) can react with a Grignard reagent following standard synthetic procedures well known to the skilled person. Thus, a compound of Formula (XIII) can react with an appropriate Grignard Reagent in an inert solvent, such as, for example, tetrahydrofuran stirring the reaction mixture at a suitable temperature, typically at 45° C., using conventional heating, for the required time to achieve completion of the reaction, typically 30 minutes. This reaction step affords intermediate compounds of Formula (XIV).

Step 2: Intermediate compounds of Formula (XIV) can be oxidized following reaction procedures well known to the people skilled in the art. Thus, a compound of Formula (XIV) can react with an appropriate oxidizing agent, such as, for example, Manganese dioxide in the presence of an inert solvent, such as, for example, dichloromethane stirring the reaction mixture at suitable temperature, typically room temperature for the required time to achieve completion of the reaction, usually 4 hours. This reaction step yields final compounds of Formula (I-s).

Scheme 9: Synthesis of compounds of Formula (I) when $R^2$ = 1,1-difluoroethoxy

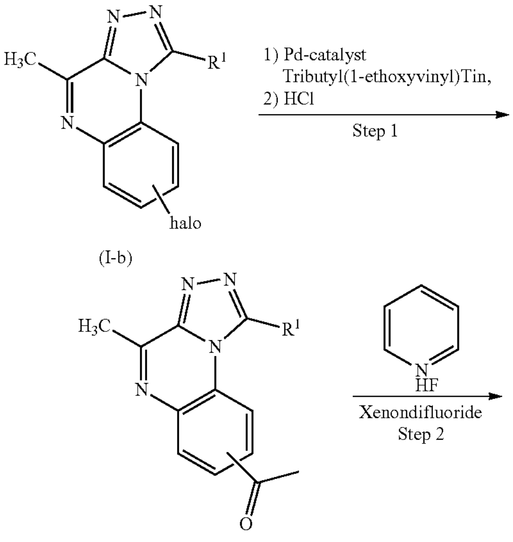

(I-b)

(XV)

-continued

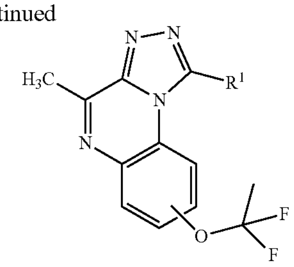

(I-t)

Step 1: Final compounds of Formula (I-b) may also be used as precursors for the synthesis of Final compounds of Formula (I-t). Thus, a compound of Formula (I-b) can react with tributyl(1-ethoxyvinyl) tin in an inert solvent, such as, for example, toluene in the presence of a palladium catalyst, such as (triphenylphosphine)tetrakis Palladium(0), and a salt such as for example lithium chloride stirring the reaction mixture at a suitable temperature, such as at 120-130° C., using conventional heating or microwave irradiation, for the required time to consume all starting material, typically 20 min for microwave heating. Then an acid solution such as hydrochloric acid solution is added and the reaction mixture can be stirred at a suitable temperature, such as 80-100° C., using conventional heating or microwave irradiation, for the required time to achieve completion of the reaction, typically 10 min for microwave heating. This reaction step affords intermediate compounds of Formula (XV).

Step 2: Intermediate compounds of Formula (XV) can react with Xenon difluoride and hydrogen fluoride-pyridine complex, in an inert solvent, such as dichloromethane, stirring the reaction at a suitable temperature, such as room temperature, for the required time to achieve completion of the reaction, typically overnight. This reaction step yields final compounds of Formula (I-t).

Preparation of Radiolabelled Final Compounds

Scheme 10: Synthesis of compounds of Formula (I) where $R^1$ = $^{18}$F-radiolabelled phenyl or pyridinyl

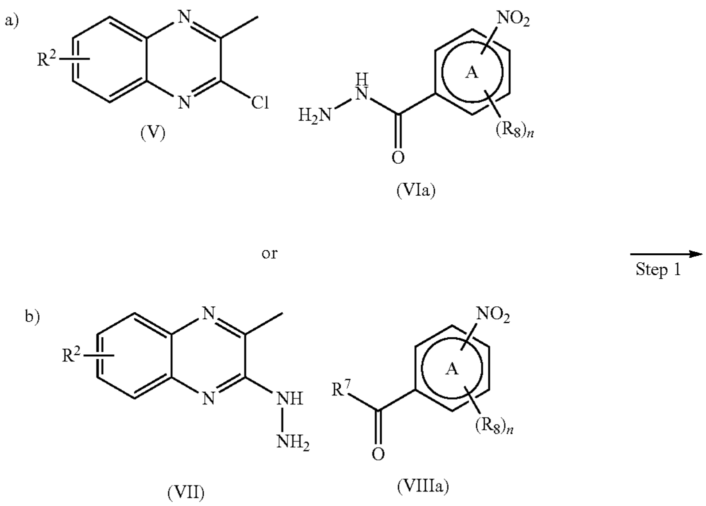

(V)

(VIa)

(VII)

(VIIIa)

-continued

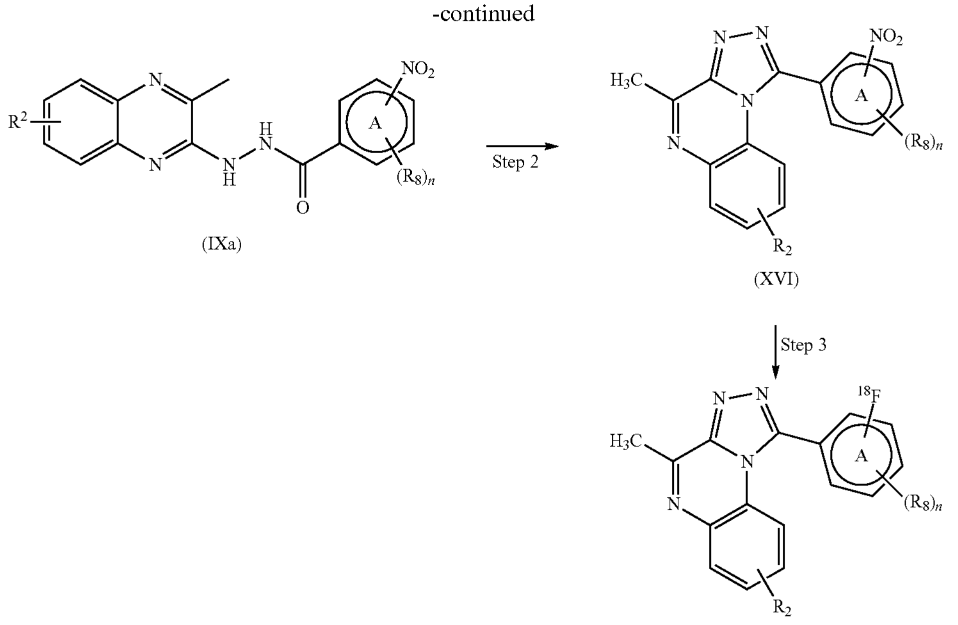

(IXa) (XVI) (I-u)

Compounds of formula (I), wherein $R^1$ is a $^{18}F$-radiolabelled phenyl or pyridinyl group, wherein ring A is phenyl or pyridinyl, $R^8$ is halo or trifluoromethyl, n is 0 or 1 and $R^2$ is as previously defined, hereby referred to as a compound of Formula (I-u) can be prepared by synthesis methods well known to the person skilled in the art. For example, by general scheme 10:

Step 1: (a) A compound of Formula (V) can be reacted with a compound of Formula (VIa) wherein ring A is phenyl or pyridinyl, $R^8$ is halo or trifluoromethyl, n is 0 or 1 and $R^2$ is as previously defined for compounds of Formula (I), according to the conditions described under Scheme 1, Method A, Step 3.

Step 1: (b) A compound of Formula (VII) can be reacted with a compound of formula (VIIIa) wherein ring A is phenyl or pyridinyl, $R^8$ is halo or trifluoromethyl, n is 0 or 1 and $R^2$ is as previously defined for compounds of Formula (I), according to the conditions described under Scheme 1, Method B, Step 2.

Step 2: Intermediate compound of Formula (IXa) can react, in presence or absence of a solvent such as for example 1,2-dichloroethane, with phosphorous oxychloride, stirring the reaction mixture at a suitable temperature, typically at 80-100° C., using conventional heating or under microwave irradiation, for the required time to achieve completion of the reaction, typically 16 hours for conventional heating.

Step 3: Intermediate compound of Formula (XVI) can undergo a nucleophilic aromatic substitution reaction with a source of $[^{18}F]$fluoride ($[^{18}F]F$) such as for example $[^{18}F]F^-/K_2CO_3$/Kryptofix® 222 complex, or $[^{18}F]KF\cdot K_{222}$ (wherein Kryptofix® 222 and $K_{222}$ mean 4,7,13,16,21,24-hexaoxa-1,10-diazabicyclo[8.8.8]hexacosane; also known as K 2.2.2) in an inert solvent such as for example anhydrous DMF under appropriate reaction conditions, such as heating in a microwave, for example at 140° or conditions known to the skilled person (for a review, see for example P. W. Miller et al. Angew. Chem. Int. Ed. 2008, 47, 8998-9033).

Scheme 11: Synthesis of compounds of Formula (I) where $R^2$ = $^3H$-radiolabelled-$L^1$—$NR^3R^4$

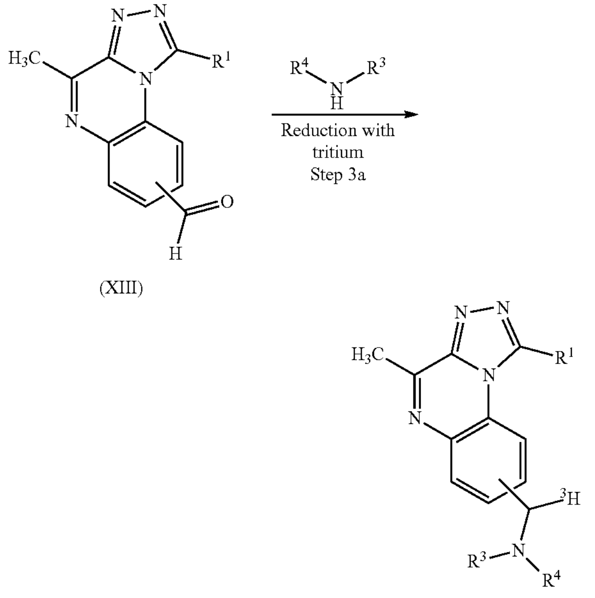

(XIII) $[^3H]$-(I-p)

Tritiated compounds of Formula (I-p), referred to herein as $[^3H]$-(I-p) may be prepared from compounds of formula (XIII) by reaction with an amine of formula $NHR^3R^4$, wherein $R^3$ and $R^4$ are as previously defined, in a reductive amination reaction using tritium in the presence of a catalyst, under conditions known to the skilled person, in two steps. Thus, a compound of formula (XIII) can react in a first step with an amine of formula $NHR^3R^4$ as previously defined in an inert solvent, such as for example, dichloromethane, optionally in the presence of a dehydrating agent such as titanium tetra(isopropoxide) stirring the reaction mixture at a suitable temperature, typically at room temperature under an inert atmosphere. After removal of the solvent the second step involves the addition of another inert aprotic solvent, such as for example, tetrahydrofuran, and reacting the intermediate imine in the presence of a reducing agent, such as tritium, and in the presence of a catalyst, such as Pt on carbon. After the addition of the reducing agent the reaction can be stirred at room temperature for the required time to achieve completion of the reaction, typically 60 min at room temperature. This reaction step yields a final compound of Formula [$^3$H]-(I-p).

Some compounds according to the invention were isolated as acid addition salt forms or isolated as free base and then converted to the acid addition salt forms. In order to obtain the acid addition salt forms of the compounds according to the invention, for example the HCl salt forms unless otherwise described, several procedures known to those skilled in the art can be used. In a typical procedure, for example, the free base can be dissolved in isopropanol, diisopropylether, diethyl ether and/or dichloromethane and subsequently, 1 to 2 equivalents of the appropriate acid, for example a 6N HCl solution in 2-propanol or a 2N HCl solution in diethyl ether, can be added dropwise. The mixture typically is stirred for 10 min or longer after which the product can be filtered off. The HCl salt is usually dried in vacuo. The values of salt stoichiometry as provided hereinbefore and hereinafter, are those obtained experimentally and may vary when using different analytical methods. When the stoichiometry of the salt is unknown the expression ".x" is used; for example, a hydrochloride salt for which the stoichiometry is unknown is referred to as ".x HCl".

Pharmacology

The compounds according to the invention inhibit PDE2 enzyme activity, in particular PDE2A, and to a lesser extent they inhibit PDE10 enzyme activity, in particular PDE10A, or inhibit both, PDE2 and PDE10 enzyme activity, in particular PDE2A and PDE10A enzyme activity and hence raise the levels of cAMP or cGMP within cells that express PDE2, or PDE2 and PDE10. Accordingly, inhibition of PDE2 or of PDE2 and PDE10 enzyme activity may be useful in the treatment of diseases caused by deficient amounts of cAMP or cGMP in cells. PDE2 or PDE2 and PDE10 inhibitors may also be of benefit in cases in which raising the amount of cAMP or cGMP above normal levels results in a therapeutic effect. Inhibitors of PDE2 or inhibitors of PDE2 and PDE10 may be used to treat neurological and psychiatric disorders, and endocrinological or metabolic diseases.

Hence, the present invention relates to a compound of formula (I) or a pharmaceutically acceptable salt or a solvate thereof according to the present invention, for use as a medicine, as well as to the use of a compound of formula (I) or a pharmaceutically acceptable salt or a solvate thereof according to the invention or a pharmaceutical composition according to the invention for the manufacture of a medicament. The present invention also relates to a compound of formula (I) or a pharmaceutically acceptable salt or a solvate thereof according to the present invention or a pharmaceutical composition according to the invention for use in the treatment or prevention of, in particular treatment of, a condition in a mammal, including a human, the treatment or prevention of which is affected or facilitated by the inhibition of phosphodiesterase 2 enzyme or phosphodiesterase 2 and 10 enzymes. The present invention also relates to the use of a compound of formula (I) or a pharmaceutically acceptable salt or a solvate thereof according to the present invention or a pharmaceutical composition according to the invention for the manufacture of a medicament for the treatment or prevention of, in particular treatment of, a condition in a mammal, including a human, the treatment or prevention of which is affected or facilitated by the inhibition of phosphodiesterase 2 enzyme or of phosphodiesterase 2 and 10 enzymes.

The present invention also relates to a compound of formula (I) or a pharmaceutically acceptable salt or a solvate thereof according to the invention, or a pharmaceutical composition according to the invention for use in the treatment, prevention, amelioration, control or reduction of the risk of various neurological and psychiatric and metabolic disorders associated with phosphodiesterase 2 or associated with phosphodiesterases 2 and 10 dysfunction in a mammal, including a human, the treatment or prevention of which is affected or facilitated by the inhibition of phosphodiesterase 2 or by the inhibition of phosphodiesterases 2 and 10.

Also, the present invention relates to the use of a compound of formula (I) or a pharmaceutically acceptable salt or a solvate thereof according to the invention or a pharmaceutical composition according to the invention for the manufacture of a medicament for treating, preventing, ameliorating, controlling or reducing the risk of various neurological and psychiatric disorders associated with phosphodiesterase 2 or associated with phosphodiesterases 2 and 10 dysfunction in a mammal, including a human, the treatment or prevention of which is affected or facilitated by the inhibition of phosphodiesterase 2 or by the inhibition of phosphodiesterases 2 and 10.

Where the invention is said to relate to the use of a compound of formula (I) or a pharmaceutically acceptable salt or a solvate thereof or composition according to the invention for the manufacture of a medicament for e.g. the treatment of a subject, e.g. a mammal, it is understood that such use is to be interpreted in certain jurisdictions as a method of e.g. treatment of a subject, comprising administering to a subject in need of such e.g. treatment, an effective amount of a compound of formula (I) or a pharmaceutically acceptable salt or a solvate thereof or composition according to the invention.

In particular, the indications that may be treated with PDE2 inhibitors, or with PDE2 and PDE10 inhibitors, either alone or in combination with other drugs, include, but are not limited to, those diseases thought to be mediated in part by the basal ganglia, prefrontal cortex and hippocampus.

These indications include neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; pain; autistic disorder or autism; and metabolic disorders.

In particular, the psychotic disorders and conditions associated with PDE2 or with PDE2 and PDE10 dysfunction include one or more of the following conditions or diseases: schizophrenia, for example of the paranoid, disorganized, catatonic, undifferentiated or residual type; schizophreniform disorder; schizoaffective disorder, such as delusional or depressive type; delusional disorder; substance-induced psychotic disorder such as psychosis induced by alcohol, amphetamine, cannabis, cocaine, hallucinogens, inhalants, opioids, or phencyclidine; personality disorders of the paranoid type; and personality disorder of the schizoid type.

In particular, the anxiety disorders include panic disorder; agoraphobia; specific phobia; social phobia; obsessive-compulsive disorder; post-traumatic stress disorder; acute stress disorder; and generalized anxiety disorder.

In particular, movement disorders include Huntington's disease and dyskinesia; Parkinson's disease; restless leg syndrome and essential tremor. Additionally, Tourette's syndrome and other tic disorders can be included.

In particular, the central nervous system disorder is a substance-related disorder selected from the group of alcohol abuse; alcohol dependence; alcohol withdrawal; alcohol withdrawal delirium; alcohol-induced psychotic disorder; amphetamine dependence; amphetamine withdrawal; cocaine dependence; cocaine withdrawal; nicotine dependence; nicotine withdrawal; opioid dependence and opioid withdrawal.

In particular, mood disorders and mood episodes include depression, mania and bipolar disorders. Preferably, the mood disorder is selected from the group of bipolar disorders (I and II); cyclothymic disorder; depression; dysthymic disorder; major depressive disorder; treatment-resistant depression; and substance-induced mood disorder.

In particular, neurodegenerative disorders include Parkinson's disease; Huntington's disease; dementia such as for example Alzheimer's disease; multi-infarct dementia; AIDS-related dementia or fronto temporal dementia. The neurodegenerative disorder or condition comprises dysfunction of striatal medium spiny neurons responses.

In particular, disorders or conditions comprising as a symptom a deficiency in attention and/or cognition include dementia, such as Alzheimer's disease; multi-infarct dementia; dementia due to Lewy body disease; alcoholic dementia or substance-induced persisting dementia; dementia associated with intracranial tumours or cerebral trauma; dementia associated with Huntington's disease; dementia associated with Parkinson's disease; AIDS-related dementia; dementia due to Pick's disease; dementia due to Creutzfeldt-Jakob disease; other diseases include delirium; amnestic disorder; post-traumatic stress disorder; stroke; progressive supranuclear palsy; mental retardation; a learning disorder; attention-deficit/hyperactivity disorder (ADHD); mild cognitive disorder; Asperger's syndrome; and age-related cognitive impairment.

In particular, pain includes acute and chronic states, severe pain, intractable pain, neuropathic pain and post-traumatic pain, cancer pain, non-cancer pain, pain disorder associated with psychological factors, pain disorder associated with a general medical condition or pain disorder associated with both psychological factors and a general medical condition.

In particular, metabolic disorders include diabetes, in particular type 1 or type 2 diabetes, and related disorders such as obesity. Additional related disorders include syndrome X, impaired glucose tolerance, impaired fasting glucose, gestational diabetes, maturity-onset diabetes of the young (MODY), latent autoimmune diabetes adult (LADA), associated diabetic dyslipidemia, hyperglycemia, hyperinsulinemia, dyslipidemia, hypertriglyceridemia, and insulin resistance.

Preferably, the psychotic disorder is selected from the group of schizophrenia, delusional disorder, schizoaffective disorder, schizophreniform disorder and substance-induced psychotic disorder.

Preferably, the central nervous system disorder is a personality disorder selected from the group of obsessive-compulsive personality disorder and schizoid, schizotypal disorder.

Preferably, the central nervous system disorder is a mood disorder selected from the group of bipolar disorders (I & II), cyclothymic disorder, depression, dysthymic disorder, major depressive disorder; treatment-resistant depression; and substance-induced mood disorder.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Preferably the disorders treated by the compounds of formula (I) or a pharmaceutically acceptable salt or a solvate thereof of the present invention are selected from schizophrenia; obsessive-compulsive disorder; generalized anxiety disorder; Huntington's disease; dyskinesia; Parkinson's disease; depression; bipolar disorders; dementia such as Alzheimer's disease; attention-deficit/hyperactivity disorder; drug abuse; pain; autism; diabetes and obesity.

Preferably, the disorders treated by the compounds of formula (I) or a pharmaceutically acceptable salt or a solvate thereof of the present invention are schizophrenia, including positive and negative symptoms thereof, and cognitive deficits, such as impaired attention or memory.

Of the disorders mentioned above, the treatment of anxiety, obsessive-compulsive disorder, post-traumatic stress disorder; generalized anxiety disorder, schizophrenia, depression, attention-deficit/hyperactivity disorder, Alzheimer's disease, dementia due to Huntington's disease, dementia due to Parkinson's disease, dementia of the Alzheimer's type, substance-induced persisting dementia and mild cognitive impairment are of particular importance.

Of the disorders mentioned above, the treatment of anxiety, obsessive-compulsive disorder, schizophrenia, depression, attention-deficit/hyperactivity disorder, and Alzheimer's disease are of particular importance.

Other central nervous system disorders include schizoanxiety disorder, and comorbid depression and anxiety, in particular major depressive disorder with comorbid generalized anxiety disorder, social anxiety disorder, or panic disorder; it is understood that comorbid depression and anxiety may also be referred to by the terms anxious depression, mixed anxiety depression, mixed anxiety-depressive disorder, or major depressive disorder with anxiety symptoms, which are used indistinctively herein.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Therefore, the invention also relates to a compound of formula (I) or a pharmaceutically acceptable salt or a solvate thereof according to the invention, for use in the treatment of any one of the diseases mentioned hereinbefore.

The invention also relates to a compound of formula (I) or a pharmaceutically acceptable salt or a solvate thereof according to the invention for use in treating any one of the diseases mentioned hereinbefore.

The invention also relates to a compound of formula (I) or a pharmaceutically acceptable salt or a solvate thereof according to the invention, for the treatment or prevention, in particular treatment, of any one of the diseases mentioned hereinbefore.

The invention also relates to the use of a compound of formula (I) or a pharmaceutically acceptable salt or a solvate thereof according to the invention, for the manufacture of a medicament for the treatment or prevention of any one of the disease conditions mentioned hereinbefore.

The invention also relates to the use of a compound of formula (I) or a pharmaceutically acceptable salt or a solvate thereof according to the invention for the manufacture of a medicament for the treatment of any one of the disease conditions mentioned hereinbefore.

The compounds of formula (I) or a pharmaceutically acceptable salt or a solvate thereof of the present invention can be administered to mammals, preferably humans, for the treatment or prevention of any one of the diseases mentioned hereinbefore.

In view of the utility of the compounds of formula (I) or a pharmaceutically acceptable salt or a solvate thereof according to the invention, there is provided a method of treating a disorder or disease mentioned hereinbefore, comprising administering to a subject in need thereof, a therapeutically effective amount of any of the compounds of formula (I) or a pharmaceutically acceptable salt or a solvate thereof or pharmaceutical compositions described herein.

Said methods comprise the administration, i.e. the systemic or topical administration, preferably oral administration, of a therapeutically effective amount of a compound of formula (I) or a pharmaceutically acceptable salt or a solvate thereof according to the invention to warm-blooded animals, including humans.

Therefore, the invention also relates to a method for the prevention and/or treatment of any one of the diseases mentioned hereinbefore comprising administering a therapeutically effective amount of compound of formula (I) or a pharmaceutically acceptable salt or a solvate thereof according to the invention to a patient in need thereof.

The PDE2 inhibitors or PDE2 and 10 inhibitors described herein can be used alone, in combination or in combination with other pharmaceutical agents such as other agents used in the treatment of psychoses, such as schizophrenia and bipolar disorder, obsessive-compulsive disorder, Parkinson's disease, cognitive impairment and/or memory loss, e.g. nicotinic $\alpha$-7 agonists, PDE4 inhibitors, other PDE2 inhibitors, other PDE10 inhibitors, other PDE2 and 10 inhibitors, calcium channel blockers, muscarinic m1 and m2 modulators, adenosine receptor modulators, ampakines, NMDA-R modulators, mGluR modulators, dopamine modulators, serotonin modulators, cannabinoid modulators, and cholinesterase inhibitors (e.g. donepezil, rivastigmine, and galantamine). In such combinations, the compounds of formula (I) or a pharmaceutically acceptable salt or a solvate thereof of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone.

One skilled in the art will recognize that a therapeutically effective amount of the PDE2 inhibitors or PDE2 and 10 inhibitors of the present invention is the amount sufficient to inhibit the PDE2 enzyme or both PDE2 and PDE10 enzymes and that this amount varies inter alia, depending on the type of disease, the concentration of the compound in the therapeutic formulation, and the condition of the patient. Generally, an amount of PDE2 inhibitor or PDE2 and 10 inhibitor to be administered as a therapeutic agent for treating diseases in which inhibition of the PDE2 enzyme is beneficial or in which inhibition of both PDE2 and PDE10 enzymes is beneficial, such as the disorders described herein, will be determined on a case by case by an attending physician.

Generally, a suitable dose is one that results in a concentration of the PDE2 inhibitor or PDE2 and 10 inhibitor at the treatment site in the range of 0.5 nM to 200 μM, and more usually 5 nM to 50 μM. To obtain these treatment concentrations, a patient in need of treatment likely will be administered between 0.001 mg/kg to 15 mg/kg body weight, in particular from 0.01 mg/kg to 2.50 mg/kg body weight, in particular, from 0.01 to 1.5 mg/kg body weight, in particular from 0.1 mg/kg to 0.50 mg/kg body weight. The amount of a compound according to the present invention, also referred to here as the active ingredient, which is required to achieve a therapeutical effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

Applications of Radiolabelled-Compounds According to the Invention

The radiolabelled compounds according to the present invention find various applications for imaging tissues, cells or a host, both in vitro and in vivo. Thus, for instance, they can be used to map the differential distribution of PDE2 enzyme in subjects of different age and sex. Further, they allow one to explore for differential distribution of PDE2 enzyme in subjects afflicted by different diseases or disorders. Thus, abnormal distribution may be helpful in diagnosis, case finding, stratification of subject populations, and in monitoring disease progression in individual subjects. The radioligands (for example, compounds of Formula [$^3$H]-(I-p) or (I-u)) may further find utility in determining PDE2 enzyme occupancy by other ligands. Since the radioligand is administered in trace amounts, no therapeutic effect may be attributed to the administration of the radioligands according to the invention.

Pharmaceutical Compositions

The present invention also provides compositions for preventing or treating diseases in which inhibition of PDE2 is beneficial or inhibition of both PDE2 and 10 is beneficial, such as neurological and psychiatric disorders, and endocrinological or metabolic diseases. Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy. A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The present compounds can be used for systemic administration such as oral, percutaneous or parenteral administration; or topical administration such as via inhalation, a nose spray, eye drops or via a cream, gel, shampoo or the like. The compounds are preferably orally administered.

The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient.

The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

For the compositions, methods and kits provided above, one of skill in the art will understand that preferred compounds for use in each are those compounds that are noted as preferred above. Still further preferred compounds for the compositions, methods and kits are those compounds provided in the non-limiting Examples below.

EXPERIMENTAL PART

I. Chemistry:

As used herein, the term "LCMS" means liquid chromatography/mass spectrometry, "GCMS" means gas chromatography/mass spectrometry, "HPLC" means high-performance liquid chromatography, "RP HPLC" means reverse phase high-performance liquid chromatography, "aq." means aqueous, "Boc" means tert-butoxycarbonyl, "nBuLi" means n-butyllithium, "BuOH" means 1-butanol, "DBU" means 2,3,4,6,7,8,9,10-octahydropyrimidol[1,2-a]azepine, "DCE" means 1,2-dichloroethane, "DCM" means dichloromethane, "DIPE" means diisopropyl ether, "DIPEA"

means diisopropylethyl amine, "DMF" means N,N-dimethylformamide, "EtOH" means ethanol, "EtOAc" means ethyl acetate, "$Et_3N$" means triethylamine, "HATU" means O-(7-azabenzotriazol-1-yl)-N,N,N',N'-tetramethyluronium hexafluorophosphate, "HBTU" means O-(benzotriazol-1-yl)-N,N,N'N,'-tetramethyluroniumhexafluoro-phosphate, "$Pd(AcO)_2$" means palladium(II) acetate, "$Pd_2(dba)_3$" means tris(dibenzylideneacetone)dipalladium(0), "Pd $(dppf)_2$ $Cl_2$" means 1,1'-[bis(diphenyl-phosphino)ferrocene] dichloro Palladium(0), "XantPhos" means 4,5-bis(diphenylphosphino)-9,9-dimethylxanthene, "Pd—C" means Palladium on carbon, "(±)BINAP" means racemic-2-2'-bis (diphenylphosphino)-1,1'-binaphtyl, "THF" means tetrahydrofuran, "min" means minutes, "h" means hours, "MeOH" means methanol, "NBS" means N-bromosuccinimide, "iPrOH" means 2-propanol, "r.m." means reaction mixture, "r.t." means room temperature" "Rt" means retention time (in minutes), "Tf" means trifluoromethanesulfonate, "TFA" means trifluoroacetic acid, "quant." means quantitative, "sat." means saturated, "sol." means solution, "$[M+H]^+$" means the protonated mass of the free base of the compound, "$[M-H]^-$" means the deprotonated mass of the free base of the compound, 'm.p." means melting point, "q.s." means quantum sufficit.

Microwave assisted reactions were performed in a single-mode reactor: Biotage Initiator™ Sixty microwave reactor (Biotage) or in a multimode reactor: MicroSYNTH Labstation (Milestone, Inc.).

Hydrogenation reactions were performed in a continuous flow hydrogenator H-CUBE® from ThalesNano Nanotechnology Inc.

Thin layer chromatography (TLC) was carried out on silica gel 60 F254 plates (Merck) using reagent grade solvents. Open column chromatography was performed on silica gel, mesh 230-400 particle size and 60 Å pore size (Merck) under standard techniques. Automated flash column chromatography was performed using ready-to-connect cartridges from Merck, on irregular silica gel, particle size 15-40 μm (normal phase disposable flash columns) on an SPOT or LAFLASH system from Armen Instrument.

Several methods for preparing the compounds of this invention are illustrated in the following examples, which are intended to illustrate but not to limit the scope of the present invention. Unless otherwise noted, all starting materials were obtained from commercial suppliers and used without further purification.

A. Synthesis of Intermediates and Precursors

Intermediates 1-a and 1-b ((I-1a) and (I-1b))

(I-1a)

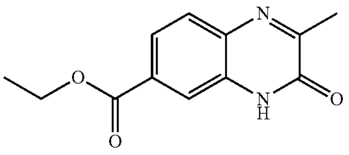

(I-1b)

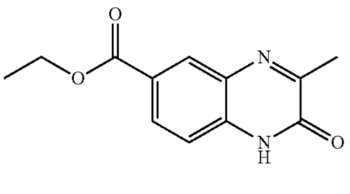

Ethyl 3,4-diaminobenzoate (15 g, 83.24 mmol) was dissolved in $CH_3COOH$ (170 mL) and $H_2O$ (145 mL) was added. Then, pyruvic acid (6.94 mL, 99.88 mmol) was added dropwise to the solution. The mixture was stirred at r.t. for 7 h, then neutralized with NaOH in pellets (ca. 100 g) and extracted with DCM. The organic solvent was dried ($Na_2SO_4$), filtered, and concentrated under vacuum to give a mixture of intermediates I-1a and I-1b around 60% pure (13.5 g) that was used as such in the next reaction step. $C_{12}H_{12}N_2O_3$. LCMS: Rt 1.51 (I-1a), 1.45 (I-1b), m/z 233 $[M+H]^+$ (method 2).

Intermediates 2-a and 2-b ((I-2a) and (I-2b))

(I-2a)

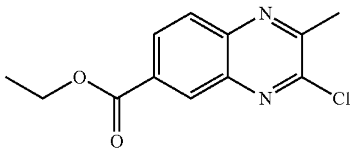

(I-2b)

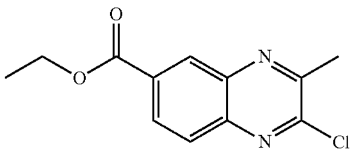

To a mixture of intermediates (I-1a) and (I-1b) (4 g, 17.22 mmol) dissolved in DCE (120 mL), $POCl_3$ (12.04 mL, 129.18 mmol) was added dropwise. The r.m. was heated under reflux for 4 h. The solvent was then evaporated and the crude mixture taken up in DCM and neutralized with $NH_4OH$. The organic phase was separated, dried ($Na_2SO_4$), filtered and concentrated. The crude product was purified by chromatography (silica, DCM 100%), the desired fractions were collected and the solvent concentrated in vacuum to give a mixture of intermediates (I-2a) and (I-2b) (2.3 g, 53%). $C_{12}H_{11}ClN_2O_2$. LCMS: Rt 2.31 (co-elution of the two peaks), m/z 251 $[M+H]^+$ (method 3).

Intermediates 3-a and 3-b ((I-3a) and (I-3b))

(I-3a)

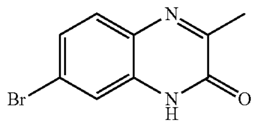

(I-3b)

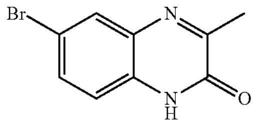

Methyl pyruvate (8.69 mL, 96.24 mmol) was added to a solution of 4-bromo-1,2-diaminobenzene (15 g, 80 mmol) dissolved in toluene (120 mL) in a round flask, equipped with a Dean-Stark apparatus. Then the r.m. was heated under reflux for 3 h. When the reaction was finished, the solvent was removed in vacuo and the crude product was washed with diethyl ether to give a mixture of intermediates (I-3a) and (I-3b) as a pale gray solid that was used as such in the next step (16 g, 83%). $C_9H_7BrN_2O$, LCMS: Rt 1.07 (first isomer), 1.15 (second isomer), m/z 239 $[M+H]^+$ (method 3).

A batch of the regioisomeric mixture was separated by suspending the mixture in methanol and ammonium hydroxide (q.s.), warming up to reflux and cooling down to room temperature. The precipitate that formed was filtered, water was added to the filtrate and the precipitate that formed was also recovered by filtration. Two additional cycles were repeated to obtain a precipitate containing a 94:6 mixture of I-3a:I-3b.

Intermediates 4-a and 4-b ((I-4-a) and (I-4-b))

(I-4a)

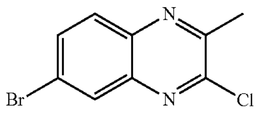

(I-4b)

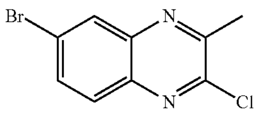

The mixture of intermediates (I-3a) and (I-3b) (16 g, 66.95 mmol) was dissolved in $POCl_3$ (78 mL), and the r.m. was stirred for 2 h at 120° C. The solvent was then evaporated and the mixture was cooled down in an ice bath and gently $NH_4OH$ was added dropwise until it reached a basic pH. Once the addition was completed, the formed precipitate was filtered off, washed with $H_2O$ and then washed several times with DCM. The organic solvent was dried ($Na_2SO_4$), filtered, and concentrated in vacuo. The crude product was purified by open column chromatography (silica, DCM in heptane 20/80 to 80/20), the desired fractions were collected and concentrated in vacuo to give a mixture of intermediates (I-4-a) and (I-4-b) as white solid (12 g, 69%). $C_9H_6BrClN_2$, LCMS: Rt 2.95 (co-elution of the two peaks), m/z 257 $[M+H]^+$ (method 11).

Intermediates 5-a and 5-b ((I-5a) and (I-5b))

(I-5a)

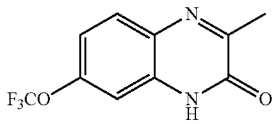

(I-5b)

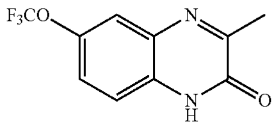

Intermediates I-5a and I-5b were synthesized following the same approach described for intermediates 3, replacing 4-bromo-1,2-diaminobenzene for 4-trifluoromethoxy-1,2-diaminobenzene (1 g, 5.21 mmol). The reaction gave a mixture of intermediates (I-5a) and (I-5b) (1.1 g, 86.5%) that was used as such for the next reaction step. $C_{10}H_7F_3N_2O_2$, LCMS: Rt 2.67 (first isomer), 2.74 (second isomer), m/z 245 $[M+H]^+$ (method 8).

Intermediates 6-a and 6-b ((I-6a) and (I-6b))

(I-6a)

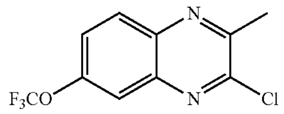

(I-6b)

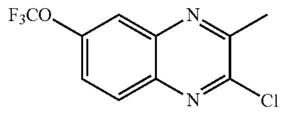

Intermediates (I6-a) and (I-6b) were synthesized following the same approach described for intermediate 4. Starting from a mixture of intermediates (I-5a) and (I-5b) (1.1 g, 4.51 mmol), intermediates (I-6a) and (I-6b) (0.9 g, 76%) were obtained. $C_{10}H_6ClF_3N_2O$, GCMS: 4.90 (co-elution of the two peaks), m/z 262 $[M^+]$ (method 1).

Intermediate 7 (I-7)

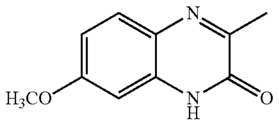

Ethyl pyruvate (6.61 mL, 59.47 mmol) was added to a solution of 4-methoxy-1,2-diaminobenzene (1.64 g, 11.89 mmol) dissolved in EtOH (36 mL) and the r.m. was stirred at room temperature for 24 hours. The resulting precipitate was filtered off, washed with EtOH and re-crystallized from diethyl ether, yielding intermediate I-7 (0.535 g, 23%).

Intermediate 8 (I-8)

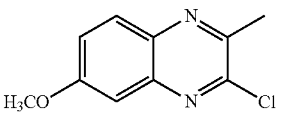

To a mixture of intermediate (I-7) (0.535 g, 2.81 mmol) dissolved in DCE (6 mL), $POCl_3$ (1.96 mL, 21.09 mmol) was added dropwise. The r.m. was heated under reflux for 6 h. The solvent was then evaporated and the crude mixture taken up in DCM and neutralized with $NH_4OH$. The organic phase was separated, dried ($Na_2SO_4$), filtered and concentrated. The crude product was purified by chromatography (silica, DCM 100%) the desired fractions were collected and the solvent concentrated in vacuum to give intermediate (I-8) (0.38 g, 65%).

Intermediate 9 (I-9)

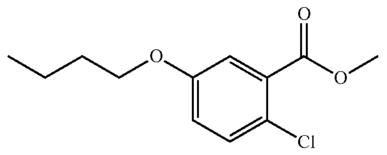 [SMILES: CCCCOc1ccc(Cl)c(C(=O)OC)c1]

Sodium hydride (60% in mineral oil, 0.16 g, 4.02 mmol) was added at r.t. to a stirred solution of methyl 2-chloro-5-hydroxybenzoate [(C.A.S. 247092-10-0), 0.5 g, 2.68 mmol] dissolved in THF (4 mL). The mixture was stirred at this temperature for 15 min and then bromobutane (0.575 mL, 5.36 mmol) was added. The stirring was continued at the same temperature overnight and then the r.m. was heated at 120° C. for 40 min under microwave irradiation. The mixture was then quenched with $H_2O$ and extracted with EtOAc, the organic layer was separated, dried ($Na_2SO_4$), filtered and concentrated in vacuo to give intermediate I-9 (0.25 g, 38.4%) as orange oil that was used as such in the next reaction step. $C_{12}H_{15}ClO_3$, GCMS: 5.78, m/z 242 [$M^+$] (method 1).

Intermediate 10 (I-10)

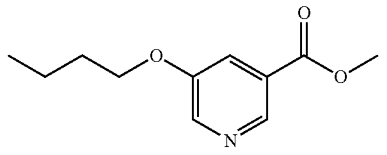

To a stirred solution of 5-hydroxynicotinic acid methyl ester (0.8 g, 5.22 mmol) and di-tert-butylazadicarboxylate (1.8 g, 7.83 mmol) in THF (6 mL), triphenylphosphine (2.05 g, 7.83 mmol) was added portionwise at r.t. The mixture was stirred at this temperature for 5 min and then BuOH (2 mL) was added and the stirring was continued at r.t. for 30 min. Then the solvent was evaporated and the crude compound purified by chromatography (silica, EtOAc in heptane 0/100 to 20/80) the desired fractions were collected and evaporated in vacuo to give intermediate I-10 as colorless oil (0.55 g, 50.3%). $C_{11}H_{15}NO_3$, LCMS: Rt 2.71, m/z 210 $[M+H]^+$ (method 8).

Intermediate 11 (I-11)

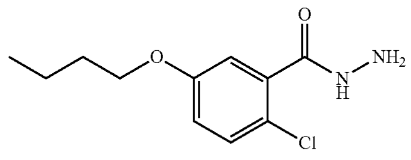 [SMILES: CCCCOc1ccc(Cl)c(C(=O)NN)c1]

Hydrazine hydrate (65% in $H_2O$, 0.118 g, 1.54 mmol) was added dropwise to a stirred solution of intermediate 1-9 (0.25 g, 1.03 mmol) in EtOH (2 mL) at r.t. and the mixture was stirred at 120° C. for 20 min under microwave irradiation. Then the solvent was evaporated under vacuum to give intermediate I-11 around 70% pure (0.32 g, 89.5%) as white solid, which was used as such in the next reaction step. $C_{11}H_{15}ClN_2O_2$, LCMS: Rt 2.34, m/z 243 $[M+H]^+$ (method 11).

Intermediate 12 (I-12)

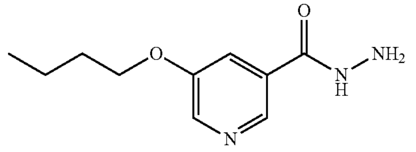

Hydrazine hydrate (60% in $H_2O$, 0.216 mL, 2.86 mmol) was added dropwise to a stirred solution of intermediate I-10 (0.5 g, 2.39 mmol) in MeOH (4 mL) at r.t. and the mixture was stirred at this temperature for 72 h. The solvent was then evaporated in vacuo to give intermediate 1-12 as white solid (0.48 g, 96%) that was used as such in the next reaction step. $C_{10}H_{15}N_3O_2$, LCMS: Rt 1.86, m/z 210 $[M+H]^+$ (method 11).

Intermediate 13 (I-13) and Final Compound 184

1-(2-Chlorophenyl)-4-methyl[1,2,4]triazolo[4,3-a] quinoxaline-8-carboxylic acid (B-184)

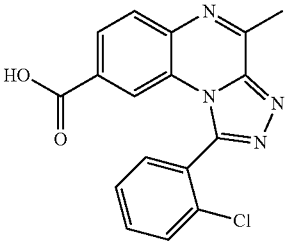 [SMILES: Cc1nc2ccc(C(=O)O)cc2n2c(-c3ccccc3Cl)nnc12]

To a mixture of compound B-1a (0.22 g, 0.6 mmol), dissolved in THF (4 mL) a solution of LiOH (0.021 g, 0.9 mmol) in $H_2O$ (2 mL) was added. The resulting mixture was stirred at r.t. for 3 h. Then the organic solvent was evaporated and the aq. phase acidified to pH=4-5. The formed precipitate was collected by filtration, washed with water and dried. The mother liquors were then further extracted with DCM and since the organic extracts and the solid compound were found to be the same product they were combined together to give intermediate 1-13 (also referred to as compound B-184) (0.2 g, 98%) as pale yellow solid. $C_{17}H_{11}ClN_4O_2$, LCMS: Rt 0.5, m/z 339 $[M+H]^+$ (method 3).

Intermediate 14 (I-14) and Final Compound 185

4-Methyl-1-phenyl[1,2,4]triazolo[4,3-a]quinoxaline-8-carboxylic acid (B-185)

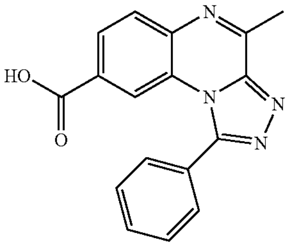 [SMILES: Cc1nc2ccc(C(=O)O)cc2n2c(-c3ccccc3)nnc12]

Intermediate I-14 (also referred to as B-185) was synthesized following the same approach described for I-13, starting from compound B-2a (0.75 g, 2.25 mmol). Intermediate I-14 (also referred to as compound B-185) was obtained as pale yellow solid (0.6 g, 87.3%). $C_{17}H_{12}N_4O_2$, LCMS: Rt 0.36, m/z 305 $[M+H]^+$ (method 3).

Intermediate 15 (I-15)

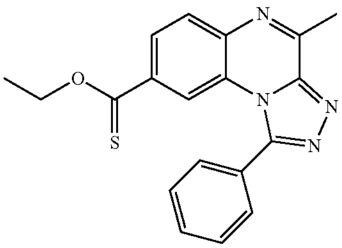 [SMILES: CCOC(=S)c1ccc2nc(C)c3nnc(-c4ccccc4)n3c2c1]

A solution of compound B-2a (0.406 g, 1.22 mmol) and Lawesson's reagent (0.494 g, 1.22 mmol) in toluene was stirred for 24 h at 150° C. The r.m. was allowed to cool to r.t. and then it was diluted with EtOAc, washed with $H_2O$ and after separation of the organic layer the aq. layer was extracted several times with EtOAc. The combined organic extracts were dried (MgSO4), filtered and the solvent concentrated in vacuo yielding the desired compound only 64% pure. Thus, the crude product was further purified by preparative HPLC on RP (Vydac® Denali® C18-10 μm, 250 g, 5 cm), mobile phase (0.25% $NH_4HCO_3$ solution in $H_2O$, MeOH). The desired fractions were collected and the solvent evaporated and co-evaporated with MeOH, yielding intermediate I-15 88% pure (0.136 g, 28%). $C_{19}H_{16}N_4OS$, LCMS: Rt 1.12, m/z 349 $[M+H]^+$ (method 6).

Intermediate 16 (I-16)

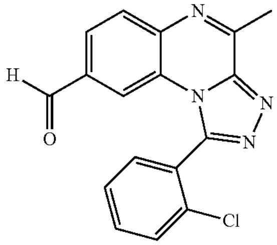 [SMILES: Cc1nc2ccc(C=O)cc2n2c(-c3ccccc3Cl)nnc12]

To a mixture of compound B-14 (3.3 g, 10.29 mmol) in 1,4-dioxane (110 mL), osmium tetraoxide (2.5% in t-BuOH, 5.33 mL, 0.411 mmol) and then sodium periodate (6.6 g, 30.86 mmol) in $H_2O$ (30 mL) were added. The mixture was stirred at r.t. for 2 h. The organic solvent was evaporated, the crude mixture diluted with more $H_2O$ and extracted with DCM. The organic layer was dried ($Na_2SO_4$), filtered and the solvent concentrated in vacuo. The crude product was purified by chromatography (Silica, EtOAC in DCM 30/70 to 70/30), the desired fractions were collected and concentrated in vacuo. The solid obtained was washed with diethylether to yield intermediate I-16 (2.5 g, 75%) as pale yellow solid. $C_{17}H_{11}ClN_4O$, LCMS: 1.78, m/z 323 $[M+H]^+$ (method 4).

Intermediate 17 (I-17)

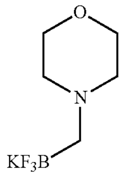

To a solution of morpholine (0.876 mL, 9.96 mmol) in $CH_3CN$ (12 mL) potassium (bromomethyl)trifluoroborate (1 g, 4.97 mmol) was added and then the r.m. was heated at 80° C. for 30 min. Then the solvent was evaporated under vacuum and the crude material re-dissolved in a solution of $KHCO_3$ (0.5 g, 4.97 mmol) in dry acetone (16 mL). The mixture was further stirred at r.t. for 20 min. Then the insoluble salts were filtered off, and the solvent concentrated again. The crude material was finally purified by dissolving it in a minimal amount of dry acetone and precipitating it with diethylether to obtain intermediate I-17 as pure product (0.66 g, 64%).

Intermediate 18 (I-18a) and (I-18b)

(I-18a)

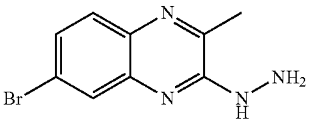

-continued (I-18b)

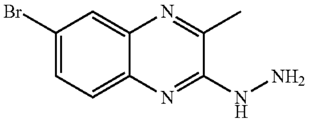

Hydrazine hydrate (60% in $H_2O$, 0.52 mL, 9.7 mmol) was added to a mixture of Intermediate (I-4-a) and Intermediate (I-4-b) (1 g, 3.88 mmol) in MeOH (15 mL) at r.t. The r.m. was then heated at 50° C. for 30 min, after that it was diluted with $H_2O$ (5 mL) and extracted with DCM (20 mL). The organic layers were separated, dried (MgSO4), filtered and concentrated in vacuo to give a mixture of intermediates (I-18a) and (I-18b) (0.92 g, 96%) that was used as such in the next reaction step. $C_9H_9BrN_4$, LCMS: 4.29 (co-elution of the two peaks), m/z 253 $[M+H]^+$ (method 10)

Intermediate 19 (I-19a) and (I-19b)

(I-19a)

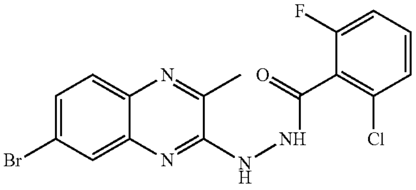

(I-19b)

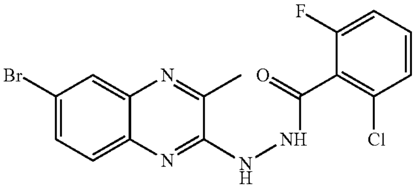

2-Chloro-6-fluorobenzoic acid (0.698 g, 4 mmol) in DMF (20 mL) and DIPEA (1.072 mL, 6.22 mmol) was treated with HBTU (1.52 g, 4 mmol) and the r.m. was stirred for 15 min at r.t. Then a mixture of intermediates (I-18a) and (I-18b) (0.9 g, 3.56 mmol) in DMF (20 mL) was added and the stirring was prolonged for further 16 h at the same temperature. The r.m. was then poured onto ice/$H_2O$ (0.5 L) and the solid thus obtained was collected by filtration. The solid was then diluted with DCM (0.1 L) and treated with 1 M NaOH aq. solution (20 mL). The organic layers were separated, washed with 1M HCl (20 mL), then with 1M NaOH (20 mL), dried (MgSO4), filtered and the solvent concentrated in vacuo. The crude mixture was purified by column chromatography (silica; MeOH in DCM 0:100 to 5:95) to give an off white solid which was recrystallized from Heptane/EtOAc (~15 mL/~5 mL) yielding finally a mixture of intermediates (I-19a) and (I-19b) as off white solid (0.75 g, 51%). $C_{16}H_{11}BrClFN_4O$, LCMS: 5.18 (co-elution of the two peaks), m/z 409 $[M+H]^+$ (method 10)

Intermediate 20-a (I-20a) and Final Compound 186

8-Bromo-1-(2-chloro-6-fluorophenyl)-4-methyl[1,2,4]triazolo[4,3-a]quinoxaline (B-186)

(I-20a)

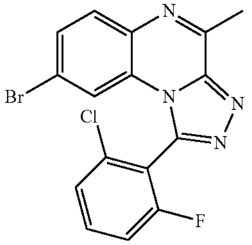

(I-20b)

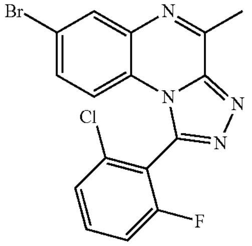

A mixture of intermediates (I-19a) and (I-19b) (1 g, 2.44 mmol) in DCE (20 mL) was treated with $POCl_3$ (0.6 mL, 6.5 mmol) and the r.m. was heated at 70° C. for 16 h. Then, additional $POCl_3$ (0.6 mL, 6.5 mmol) was added and the mixture heated at the same temperature as before further for 5 h. After this time, again more $POCl_3$ (1.2 mL, 13 mmol) was added and the mixture heated as before for further 16 h. The r.m. was cooled and poured onto ice/aq. $NH_4OH$ (150 mL/150 mL) and the layers separated. The organic phase was dried ($MgSO_4$), filtered and concentrated in vacuo. The crude compound was purified by chromatography (silica; MeOH in DCM 0/100 to 2/98) to give a mixture of intermediate (I-20a) together with its regioisomer (I-20b) (0.7 g, 75%).

A batch of the regioisomeric mixture was separated by column chromatography (silica, EtOAc in $CH_2Cl_2$, 0/100 to 25/75) to give intermediate (I-20a) (also referred to as compound B-186a) as pure isomer. $C_{16}H_9BrClFN_4$, LCMS: 2.58, m/z 391 $[M+H]^+$ (method 4).

Intermediate 21 (I-21) and Final Compound 187

1-(2-Chloro-6-fluorophenyl)-8-ethenyl-4-methyl[1,2,4]triazolo[4,3-a]quinoxaline (B-187)

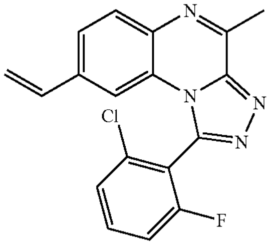 [SMILES: C=Cc1ccc2nc(C)c3nnc(-c4c(F)cccc4Cl)n3c2c1]

Tributylvinyl tin (0.18 mL, 0.61 mmol) was added to a stirred solution of intermediate (I-20a) (0.2 g, 0.511 mmol), LiCl (0.065 g, 1.53 mmol) and (tetrakis)triphenylphosphine palladium(0) (0.023 g, 0.02 mmol) in toluene (7 mL). The mixture was heated at 120° C. for 1.5 h. After cooling to r.t. the r.m. was partitioned between EtOAc and $H_2O$. The organic layer was washed with brine, separated, dried ($Na_2SO_4$) and concentrated in vacuo. The crude product was purified by chromatography (silica, EtOAc in DCM 10/90 to 50/50), the desired fractions were collected and concentrated in vacuo, to yield Intermediate compound (I-21) (also referred to as compound B-187) as pale yellow solid (0.14 g, 81%). $C_{18}H_{12}ClFN_4$, LCMS: 2.46, m/z 339 $[M+H]^+$ (method 4)

Intermediate 22 (I-22)

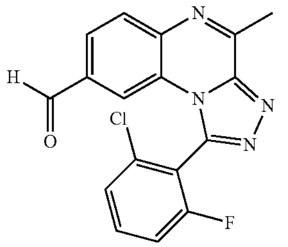 [SMILES: Cc1nc2ccc(C=O)cc2n2c(-c3c(F)cccc3Cl)nnc12]

To a solution of intermediate (I-21) (0.14 g, 0.413 mmol) in 1,4-dioxane (5 mL), osmium tetraoxide (2.5% in t-BuOH, 0.214 mL, 0.016 mmol) and then sodium periodate (0.265 g, 1.24 mmol) in $H_2O$ (3 mL), were added. The mixture was stirred at r.t. for 2.5 h. The organic solvent was evaporated, the crude mixture diluted with more $H_2O$ and extracted with DCM. The organic layer was separated, dried ($Na_2SO_4$) and concentrated in vacuo. The crude product was purified by chromatography (Silica, EtOAc in DCM 30/70 to 70/30), the desired fractions were collected and concentrated in vacuo yielding intermediate (I-22) as pale yellow solid (0.1 g, 71%). $C_{17}H_{10}ClFN_4O$, LCMS: 1.82, m/z 341 $[M+H]^+$ (method 4).

Intermediate 23 (I-23)

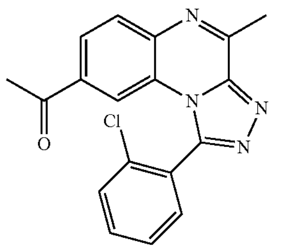 [SMILES: CC(=O)c1ccc2nc(C)c3nnc(-c4ccccc4Cl)n3c2c1]

Tributyl-(1-ethoxyvinyl) tin (0.217 mL, 0.64 mmol) was added to a stirred solution of compound B-3a (0.2 g, 0.53 mmol), palladium(0) (tetrakis)triphenylphosphine (0.025 g, 0.02 mmol) and LiCl (0.068 g, 1.61 mmol) in toluene (2 ml) at r.t. The mixture was then heated at 120° C. for 20 min under microwave irradiation. After that, HCl (aq. 2M, 1.5 mL) was added and the reaction was heated again at 80° C. for 10 min under microwave irradiation. The mixture was basified with NaOH (aq. 2M), extracted with EtOAc, the organic phase was separated, dried ($Na_2SO_4$), filtered and the solvent evaporated in vacuo. The crude mixture was purified by chromatography (silica, EtOAc in DCM 30/70 to 70/30). The desired fractions were collected and concentrated in vacuo, and the solid obtained was further washed with diethylether/DIPE affording I-23 as white solid (0.12 g, 66.5%). $C_{18}H_{13}ClN_4O$, LCMS: 1.84, m/z 337 $[M+H]^+$ (method 4).

Intermediate 24 (I-24) and Final Compound 188

8-Bromo-1-(2,5-dichlorophenyl)-4-methyl[1,2,4]triazolo[4,3-a]quinoxaline (B-188)

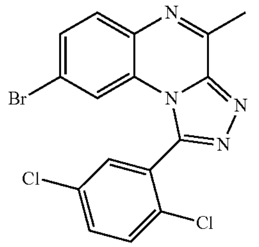 [SMILES: Cc1nc2ccc(Br)cc2n2c(-c3cc(Cl)ccc3Cl)nnc12]

To a 94:6 mixture of intermediates (I-4-a):(I-4-b) (0.1 g, 0.38 mmol) dissolved in EtOH (1.6 mL), 2,5-dichlorobenzhydrazide (0.101 g, 0.46 mmol) was added. The reaction mixture was heated in a microwave oven at 170° C. for 20 min. The mixture was then evaporated till dryness and the residue taken up in DCM. The organic layer was washed with $K_2CO_3$ (sat. sol.), then separated, dried ($Na_2SO_4$), filtered and the solvent evaporated in vacuo. The crude mixture was purified by chromatography (silica, EtOAc in DCM 0/100 to 15/85), the desired fractions were collected and evaporated to give intermediate I-24 (also referred to as compound B-188) (0.083 g, 51.8%). $C_{16}H_9BrCl_2N_4$, LCMS: 1.12, m/z 407 $[M+H]^+$ (method 6).

Intermediate 25 (I-25) and Final Compound 189

8-Bromo-4-methyl-1-(4-methylpyridin-3-yl) [1,2,4]triazolo[4,3-a]quinoxaline (B-189)

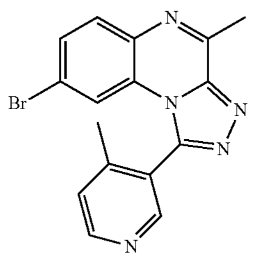 [SMILES: Cc1ccncc1-c1nnc2c(C)nc3ccc(Br)cc3n12]

To a mixture of intermediates (I-4-a) and (I-4-b) (0.3 g, 1.16 mmol) dissolved in n-butyl alcohol (12 mL) was added 3-pyridinecarboxylic acid, 4-methyl-hydrazide (0.185 g, 1.22 mmol). The reaction mixture was heated in a sealed reactor for 35 min at 160° C. After cooling to room temperature, the mixture was heated for an additional 20 min at 160° C. The mixture was then cooled to room temperature, evaporated to dryness and the residue taken up in EtOAc. The organic layer was washed with $NaHCO_3$ (sat. sol.), then separated, dried ($MgSO_4$), filtered and the solvent evaporated in vacuo. DIPE was added and the resulting solid was filtered to provide intermediate 1-25 (also referred to as compound B-189) (0.15 g, 36%). The minor isomer was present in less than 5% and was removed during the purification of the subsequent synthetic steps.

Intermediate 26 (I-26) and Final Compound 190

8-Ethenyl-4-methyl-1-(4-methylpyridin-3-yl)[1,2,4]triazolo[4,3-a]quinoxaline (B-190)

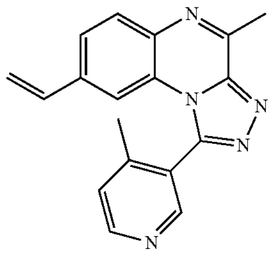 [SMILES: C=Cc1ccc2nc(C)c3nnc(-c4cnccc4C)n3c2c1]

Starting from I-25 (0.15 g, 0.423 mmol), and following the same procedure described for intermediate I-21, intermediate I-26 (also referred to as compound B-190) was obtained (0.114 g, 89%).

Intermediate 27 (I-27)

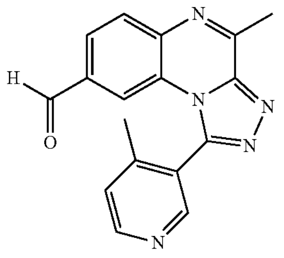 [SMILES: Cc1ccncc1-c1nnc2c(C)nc3ccc(C=O)cc3n12]

Starting from I-26 (0.114 g, 0.368 mmol), and following the same procedure described for intermediate I-22, intermediate I-27 was obtained (0.07 g, 60%).

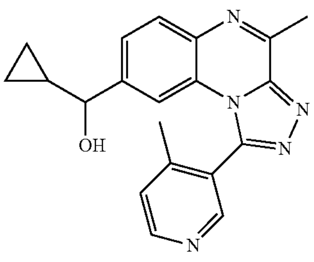 [SMILES: Cc1ccncc1-c1nnc2c(C)nc3ccc(C(O)C4CC4)cc3n12]

Intermediate 28 (I-28)

To a mixture of intermediate I-27 (0.07 g, 0.23 mmol), in dry THF (0.7 mL), cyclopropylmagnesium bromide (0.51 mL, 0.25 mmol) was added at r.t. The r.m. was stirred at this temperature for 2 h, then the mixture was quenched with $NH_4Cl$ (sat. sol.) and extracted with DCM. The organic layer was separated, dried ($Na_2SO_4$), filtered and the solvent evaporated in vacuo. The crude mixture was purified by chromatography (silica, EtOAc in DCM 30/70 to 70/30), the desired fractions were collected and evaporated in vacuo. The solid obtained was then washed with diethyl ether to give intermediate I-28 (0.079 g, quant yield).

Intermediate 29 (I-29) and Final Compound 191

1-(5-Butoxypyridin-3-yl)-8-ethenyl-4-methyl[1,2,4]triazolo[4,3-a]quinoxaline (B-191)

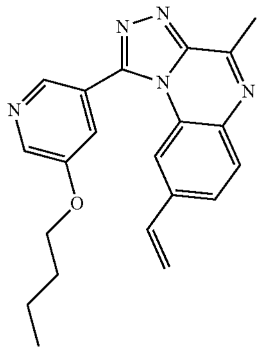 [SMILES: C=Cc1ccc2nc(C)c3nnc(-c4cncc(OCCCC)c4)n3c2c1]

To a stirred solution of B-7 (2.35 g, 5.7 mmol) in toluene (17 mL), were added LiCl (0.719 g, 17.1 mmol), (tetrakis)triphenylphosphine palladium(0) (0.263 g, 0.23 mmol) and tributylvinyl tin (1.84 mL, 6.27 mmol) and the mixture was heated at 120° C. for 2 h. After cooling to r.t. the r.m. was partitioned between EtOAc and $H_2O$. The organic layer was washed with brine, separated, dried ($Na_2SO_4$) and concentrated in vacuo. The crude product was purified by chromatography (silica, EtOAc in heptane 0/100 to 100/0), the desired fractions were collected and concentrated in vacuo, to yield intermediate 29 (I-29) (also referred to as compound B-191) (1.9 g, 92%).

Intermediate 30 (I-30)

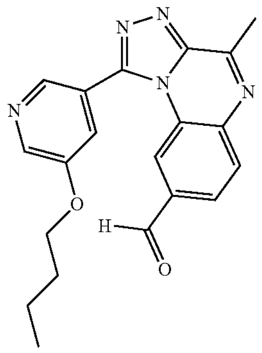 [SMILES: CCCCOc1cncc(-c2nnc3c(C)nc4ccc(C=O)cc4n23)c1]

To a solution of intermediate I-29 (0.159 g, 0.44 mmol) in 1,4-dioxane (4.4 mL), osmium tetraoxide (2.5% in t-BuOH, 0.23 mL, 0.018 mmol) and then sodium periodate (0.282 g, 1.32 mmol) in $H_2O$ (1.32 mL), were added. The mixture was stirred at r.t. for 2 h. The organic solvent was evaporated, the crude mixture diluted with more $H_2O$ and extracted with DCM. The organic layer was separated, dried ($Na_2SO_4$) and concentrated in vacuo. The crude product was purified by chromatography (silica, EtOAc in DCM 0/1 to 1/1), the desired fractions were collected and concentrated in vacuo yielding intermediate (I-30) (0.108 g, 68%).

Intermediates 31a and 31b (I-31a) and (I-31b)

(I-31a)

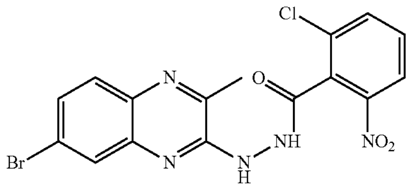

(I-31b)

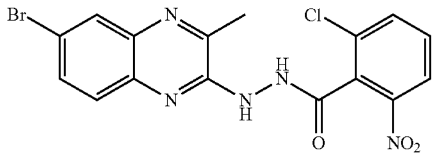

DMF (0.182 mL, 2.34 mmol) was added to a mixture of 2-chloro-6-nitrobenzoic acid (0.473 g, 2.34 mmol) and oxalyl chloride (0.201 mL, 2.34 mmol) in dichloromethane (5 mL). The mixture was stirred for 15 min at RT, then this solution was added dropwise to a stirred mixture of triethylamine (0.544 mL, 1.95 mmol) and intermediate compounds I-18a and I-18b (0.495 g, 1.95 mmol) dissolved in dichloromethane (5 mL) at 0° C. The mixture was then allowed to RT and stirred for further 15 min. Then it was quenched with NaHCO3 (sat. sol. in water), the organic layer was quickly separated and the solvent evaporated. The residue was treated with ethyl ether to yield a mixture of (I-31a) and (I-31b) as a brown solid (0.814 g, 95%) that was used as such in the next reaction step.

Intermediates 32a (I-32a) and 32b (I-32b)

(I-32a)

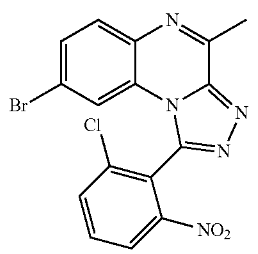

(I-32b)

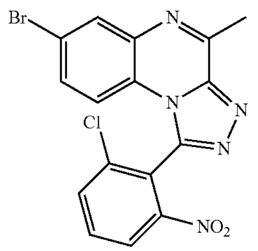

A mixture of intermediate compounds I-31a and I-31b (0.402 g, 0.92 mmol) in DCE (5 mL) was treated with $POCl_3$ (0.343 mL, 3.68 mmol) and the r.m. was heated at 160° C. for 10 min under microwave irradiation. The solvent was then evaporated and the crude compound purified by chromatography (silica, EtOAc in heptanes 20/80 to 60/40). The desired fractions were collected, the solvent evaporated under vacuum to give I-32a (0.053 g, 13.7%) and I-32b (0.112 g, 29%) as pure isomers.

Intermediate I-33

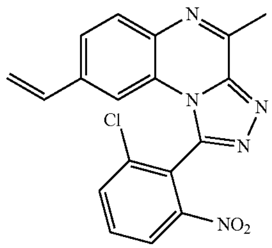

Intermediate I-33 was synthesized following a similar approach described for compound B-14. Starting from I-32a (0.053 g, 0.127 mmol) intermediate I-33 was obtained as pale yellow solid (0.046 g, quant.).

Intermediate I-34

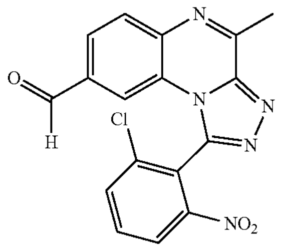 [SMILES: Cc1nc2ccc(C=O)cc2n2c(-c3c(Cl)cccc3[N+](=O)[O-])nnc12]

Intermediate I-34 was synthesized following a similar approach described for intermediate I-16. Starting from I-33 (0.046 g, 0.127 mmol) intermediate 1-34 was obtained as pale yellow solid (0.031 g, 66.5%).

Intermediate I-35

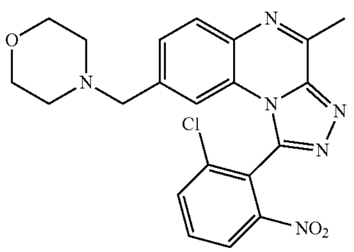 [SMILES: Cc1nc2ccc(CN3CCOCC3)cc2n2c(-c3c(Cl)cccc3[N+](=O)[O-])nnc12]

Intermediate I-35 was synthesized following a similar approach described for compound B-19. Starting from 1-34 (0.035 g, 0.095 mmol) intermediate compound I-35 was obtained (0.011 g, 27%).

B-Synthesis of Final Compounds

Example 1

Ethyl 1-(2-chlorophenyl)-4-methyl[1,2,4]triazolo[4,3-a]quinoxaline-8-carboxylate (B-1a) and ethyl 1-(2-chlorophenyl)-4-methyl[1,2,4]triazolo[4,3-a]quinoxaline-7-carboxylate (B-1b)

(B-1a)

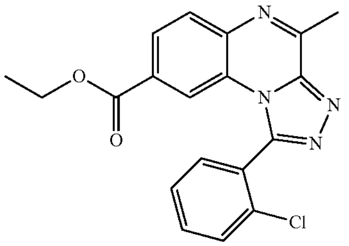

(B-1b)

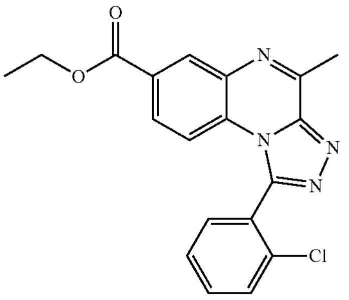

To a mixture of intermediates (I-2a) and (I-2b) (0.4 g, 1.6 mmol) dissolved in EtOH (2 mL), 2-chlorobenzhydrazide (0.3 g, 1.76 mmol) was added. The reaction mixture was heated in a microwave oven at 160° C. for 15 min. The mixture was then evaporated till dryness and the residue taken up in DCM. The organic layer was washed with $K_2CO_3$ (sat. sol.), then separated, dried ($Na_2SO_4$), filtered and the solvent evaporated in vacuo. The crude mixture was purified by chromatography (silica, EtOAc in heptane 70/30 to 100/0), the desired fractions were collected and evaporated to give final product B-1a (0.22 g, 37.5%) and final product B-1b (0.16 g, 27.3%) as pure isomers (both as white solids). $^1$H NMR (500 MHz, $CDCl_3$) δ ppm 1.28 (t, J=7.2 Hz, 3H), 3.12 (s, 3H), 4.21-4.34 (m, 2H), 7.56-7.63 (m, 1H), 7.66-7.74 (m, 3H), 7.96 (d, J=1.7 Hz, 1H), 8.10 (d, J=8.4 Hz, 1H), 8.22 (dd, J=8.5, 1.9 Hz, 1H) (For B-1a). $^1$H NMR (400 MHz, $CDCl_3$) δ ppm 1.41 (t, J=7.2 Hz, 3H), 3.11 (s, 3H), 4.42 (q, J=7.2 Hz, 2H), 7.29 (d, J=8.8 Hz, 1H), 7.54-7.60 (m, 1H), 7.64-7.73 (m, 3H), 8.03 (dd, J=8.8, 2.1 Hz, 1H), 8.75 (d, J=1.8 Hz, 1H) (for B-1b).

Example 2

Ethyl 4-methyl-1-phenyl[1,2,4]triazolo[4,3-a]quinoxaline-8-carboxylate (B-2a) and Ethyl 4-methyl-1-phenyl[1,2,4]triazolo[4,3-a]quinoxaline-7-carboxylate (B-2b)

(B-2a)

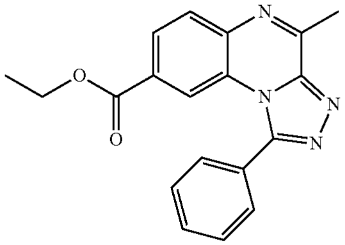

(B-2b)

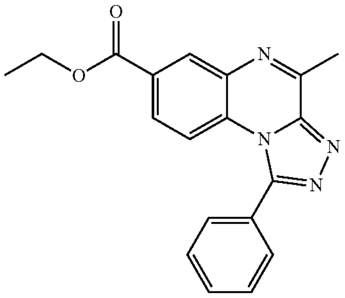

Final compounds B-2a and B-2b were synthesized following the same procedure described in Example 1. Starting from a mixture of intermediates I-2a and I-2b (1.2 g, 4.79 mmol), and replacing 2-chlorobenzhydrazide for benzhydrazide final compounds B-2a (0.75 g, 47%) and B-2b (0.35 g, 22%) were obtained as pure isomers. $^1$H NMR (400 MHz, $CDCl_3$) δ ppm 1.28 (t, J=7.1 Hz, 3H), 3.10 (s, 3H), 4.27 (q, J=7.2 Hz, 2H), 7.62-7.77 (m, 5H), 8.08 (d, J=8.6 Hz, 1H), 8.19 (dd, J=8.3, 1.6 Hz, 1H), 8.24 (d, J=1.6 Hz, 1H) (for B-2a). $^1$H NMR (400 MHz, $CDCl_3$) δ ppm 1.41 (t, J=7.2 Hz, 3H), 3.09 (s, 3H), 4.42 (q, J=7.0 Hz, 2H), 7.56 (d, J=8.8 Hz, 1H), 7.61-7.74 (m, 5H), 7.99 (dd, J=8.8, 1.8 Hz, 1H), 8.73 (d, J=1.8 Hz, 1H) (for B-2b).

Example 3

8-Bromo-1-(2-chlorophenyl)-4-methyl[1,2,4]triazolo[4,3-a]quinoxaline (B-3a) and 7-Bromo-1-(2-chlorophenyl)-4-methyl[1,2,4]triazolo[4,3-a]quinoxaline (B-3b)

(B-3a)

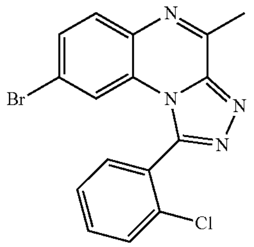

-continued (B-3b)

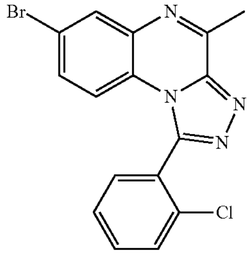

Final compounds B-3a and B-3b were synthesized following the same procedure described in Example 1. Starting from a mixture of intermediates I-4a and I-4b (0.3 g, 1.16 mmol), final compound B-3a (0.13 g, 29.8%) and final product B-3b (0.11 g, 25.2%) were obtained as pure isomers (both as solid compounds). $^1$H NMR (500 MHz, $CDCl_3$) δ ppm 3.07 (s, 3H), 7.32 (d, J=2.0 Hz, 1H), 7.56-7.62 (m, 1H), 7.65-7.72 (m, 4H), 7.92 (d, J=8.7 Hz, 1H) (for B-3a). $^1$H NMR (500 MHz, $CDCl_3$) δ ppm 3.09 (s, 3H), 7.10 (d, J=9.0 Hz, 1H), 7.46 (dd, J=9.0, 2.3 Hz, 1H), 7.54-7.58 (m, 1H), 7.63-7.71 (m, 3H), 8.22 (d, J=2.0 Hz, 1H) (for B-3b).

Example 4

1-(2-Chlorophenyl)-4-methyl-8-(trifluoromethoxy)[1,2,4]triazolo[4,3-a]quinoxaline (B-4a) and 1-(2-Chlorophenyl)-4-methyl-7-(trifluoromethoxy)[1,2,4]triazolo[4,3-a]quinoxaline (B-4b)

(B-4a)

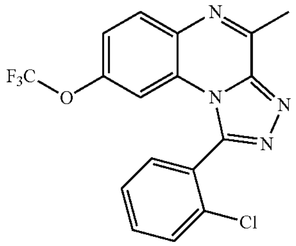

(B-4b)

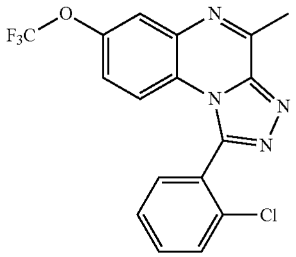

Final compounds B-4a and B-4b were synthesized following the same procedure described in Example 1. Starting from a mixture of intermediates I-6a and I-6b (0.25 g, 0.95 mmol), final product B-4a as white solid (0.03 g, 8.1%) and final product B-4b as sticky solid (0.07 g, 19.4%) were obtained. $^1$H NMR (400 MHz, $CDCl_3$) δ ppm 3.09 (s, 3H), 7.07-7.10 (m, 1H), 7.40 (dd, J=8.8, 2.3 Hz, 1H), 7.55-7.61 (m, 1H), 7.64-7.73 (m, 3H), 8.09 (d, J=9.0 Hz, 1H). (for B-4a). $^1$H NMR (500 MHz, $CDCl_3$) δ ppm 3.10 (s, 3H), 7.23 (dd, J=9.2, 2.3 Hz, 1H), 7.27 (d, J=8.7 Hz, 1H), 7.54-7.60 (m, 1H), 7.64-7.72 (m, 3H), 7.94 (br. s, 1H) (for B-4b).

Example 5

1-(2-Chlorophenyl)-8-methoxy-4-methyl[1,2,4]triazolo[4,3-a]quinoxaline (B-5)

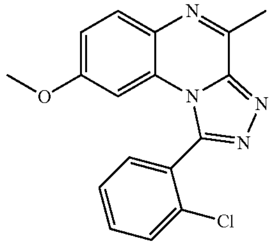

To a mixture of intermediate I-8 (0.170 g, 0.815 mmol) dissolved in BuOH (4 mL), 2-chlorobenzhydrazide (0.146 g, 0.855 mmol) was added. The r.m. was heated in a sealed tube at 160° C. for 35 min. The mixture was then evaporated till dryness and the residue taken up in EtOAc. The organic layer was washed with $NaHCO_3$ (sat. sol.), then separated, dried ($MgSO_4$), filtered and the solvent evaporated in vacuo. The crude mixture was purified by chromatography (silica, MeOH in DCM 0/100 to 25/75), the desired fractions were collected and evaporated. The solid compound obtained was triturated with diethyl ether to give final compound B-5 (0.203 g, 77%). $^1$H NMR (300 MHz, DMSO-$d_6$) δ ppm 2.90 (s, 3H) 3.52 (s, 3H) 6.49 (d, J=2.6 Hz, 1H) 7.26 (dd, J=9.0, 2.7 Hz, 1H) 7.65-7.75 (m, 1H) 7.76-7.90 (m, 3H) 7.98 (d, J=8.9 Hz, 1H).

Example 6

8-Bromo-1-(5-butoxy-2-chlorophenyl)-4-methyl[1,2,4]triazolo[4,3-a]quinoxaline (B-6a) and 7-Bromo-1-(5-butoxy-2-chlorophenyl)-4-methyl[1,2,4]triazolo[4,3-a]quinoxaline (B-6b)

(B-6a)

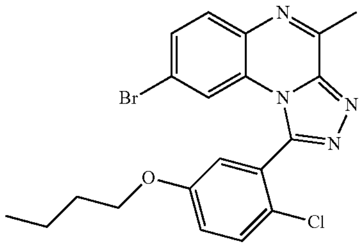

(B-6b)

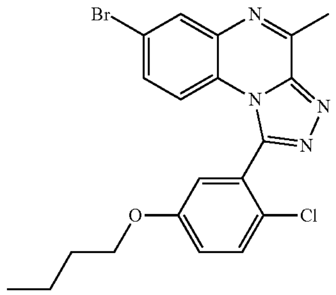

Final compounds B-6a and B-6b were synthesized following the same procedure described in Example 1. Starting from a mixture of intermediates I-4a and I-4b (0.2 g, 0.77 mmol) and intermediate I-11, final product B-6a (0.05 g, 14.4%) and final product B-6b (0.075 g, 21.6%) as pure isomers (both as off-white solids) were obtained. $^1$H NMR (500 MHz, $CDCl_3$) δ ppm 0.98 (t, J=7.4 Hz, 3H), 1.50 (sxt, J=7.5 Hz, 2H), 1.76-1.84 (m, 2H), 3.06 (s, 3H), 3.93-4.10 (m, 2H), 7.16-7.21 (m, 2H), 7.44 (d, J=1.7 Hz, 1H), 7.50-7.58 (m, 1H), 7.68 (dd, J=8.7, 2.0 Hz, 1H), 7.91 (d, J=8.7 Hz, 1H) (for B-6a). $^1$H NMR (500 MHz, $CDCl_3$) δ ppm 0.97 (t, J=7.4 Hz, 3H), 1.49 (sxt, J=7.5 Hz, 2H), 1.74-1.84 (m, 2H), 3.08 (s, 3H), 3.93-4.08 (m, 2H), 7.14-7.21 (m, 3H), 7.45-7.54 (m, 2H), 8.22 (d, J=2.0 Hz, 1H). (for B-6b).

Example 7

8-Bromo-1-(5-butoxypyridin-3-yl)-4-methyl[1,2,4]triazolo[4,3-a]quinoxaline (B-7)

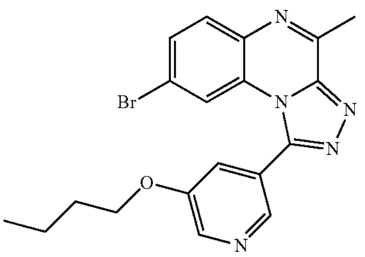 [SMILES: CCCCOc1cncc(-c2nnc3c(C)nc4ccc(Br)cc4n23)c1]

To a solution of intermediate I-4a (5 g, 19.4 mmol) in BuOH (40 ml) intermediate I-12 (4.06 g, 19.4 mmol) was added. The r.m. was heated in a sealed reactor at 160° C. for 30 min. The mixture was then evaporated till dryness and the residue taken up in EtOAc. The organic layer was washed with $NaHCO_3$ (sat. sol.), then separated, dried ($MgSO_4$), filtered and the solvent evaporated in vacuo. The crude mixture was purified by chromatography (silica, EtOAc in DCM 5/95 to 25/75), the desired fractions were collected and evaporated, and the solid compound obtained was further triturated with heptane to give final compound B-7 (3.3 g, 41%). $^1$H NMR (300 MHz, DMSO-$d_6$) δ ppm 0.93 (t, J=7.4 Hz, 3H), 1.45 (sxt, J=7.5 Hz, 2H), 1.75 (quin, J=6.3 Hz, 2H), 2.92 (s, 3H), 4.13 (t, J=6.3 Hz, 2H), 7.48 (d, J=1.6 Hz, 1H), 7.82 (dd, J=8.7, 1.8 Hz, 1H), 7.91 (br. s., 1H), 7.99 (d, J=8.7 Hz, 1H), 8.55 (br. s, 1H), 8.65 (d, J=2.6 Hz, 1H).

Example 8

Benzyl 4-methyl-1-phenyl[1,2,4]triazolo[4,3-a]quinoxaline-8-carboxylate (B-8)

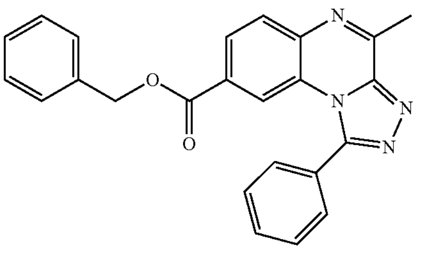 [SMILES: Cc1nc2ccc(C(=O)OCc3ccccc3)cc2n2c(-c3ccccc3)nnc12]

Intermediate I-14 (0.055 g, 0.181 mmol) was dissolved in DMF (2 mL), then DBU (0.06 mL, 0.39 mmol) and benzyl bromide (0.032 mL, 0.27 mmol) were added. The r.m. was stirred at r.t. for 3 h. The solvent was then evaporated in vacuo, the crude compound taken up in $H_2O$ and extracted with DCM. The organic layer was separated, dried ($Na_2SO_4$), filtered and the solvent evaporated in vacuo. The crude compound was purified by chromatography (silica, EtOAC in heptane 60/40 to 100/0) the desired fractions were collected and the solvent evaporated to give final compound B-8 as pale yellow solid (0.046 g, 65.5%). $^1$H NMR (400 MHz, $CDCl_3$) δ ppm 3.09 (s, 3H), 5.24 (s, 2H), 7.28-7.34 (m, 2H), 7.38-7.44 (m, 3H), 7.47-7.54 (m, 3H), 7.64-7.72 (m, 2H), 8.09 (d, J=8.3 Hz, 1H), 8.23 (dd, J=8.3, 1.8 Hz, 1H), 8.26 (d, J=1.8 Hz, 1H).

Example 9

N-Benzyl-4-methyl-1-phenyl[1,2,4]triazolo[4,3-a]quinoxaline-8-carboxamide (B-9)

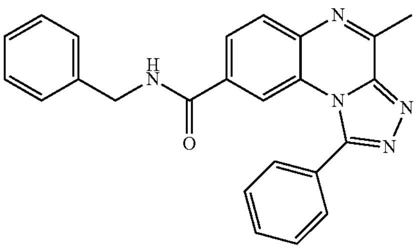 [SMILES: Cc1nc2ccc(C(=O)NCc3ccccc3)cc2n2c(-c3ccccc3)nnc12]

Intermediate I-14 (0.2 g, 0.66 mmol), HATU (0.3 g, 0.79 mmol) and DIPEA (0.11 mL, 0.66 mmol) in DMF (2 mL) were treated with a solution of benzyl amine (0.086 mL, 0.79 mmol) in DCM (5 mL). The r.m. was stirred at r.t. for 2 h and then quenched with $H_2O$ and extracted with DCM. The organic layer was separated, dried ($Na_2SO_4$), filtered and the solvent evaporated till dryness. The solid compound obtained was then washed several times with iPrOH and then diethyl ether to give final product B-9 as white solid (0.22 g, 85%). $^1$H NMR (400 MHz, $CDCl_3$) δ ppm 3.08 (s, 3H), 4.53 (d, J=5.5 Hz, 2H), 6.01 (br. t, J=4.6, 4.6 Hz, 1H), 7.24-7.29 (m, 2H), 7.33-7.43 (m, 3H), 7.46-7.56 (m, 3H), 7.65-7.71 (m, 2H), 7.88 (d, J=1.4 Hz, 1H), 7.96 (dd, J=8.3, 1.8 Hz, 1H), 8.07 (d, J=8.3 Hz, 1H).

Example 10

1-(2-Chlorophenyl)-N-ethyl-4-methyl[1,2,4]triazolo[4,3-a]quinoxaline-8-carboxamide (B-10)

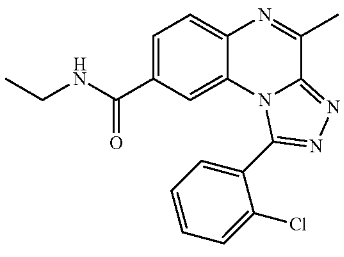 [SMILES: CCNC(=O)c1ccc2nc(C)c3nnc(-c4ccccc4Cl)n3c2c1]

Intermediate I-13 (0.06 g, 0.177 mmol), HATU (0.08 g, 0.21 mmol) and DIPEA (0.037 mmol, 0.21 mmol) in DMF (1 mL) were treated with a solution of ethylamine (2 M in THF, 0.132 mL, 0.266 mmol) in DCM (3 mL). The r.m. was stirred at r.t. for 2 h and then quenched with $H_2O$ and extracted with DCM. The organic layers were separated, dried ($Na_2SO_4$), filtered and the solvent evaporated till dryness. The solid compound obtained was then washed several times with iPrOH and then with diethyl ether to give final product B-10 as white solid (0.035 g, 54%). $^1H$ NMR (500 MHz, $CDCl_3$) δ ppm 1.20 (t, J=7.4 Hz, 3H), 3.11 (s, 3H), 3.39-3.47 (m, 2H), 5.79 (br. s., 1H), 7.57-7.63 (m, 1H), 7.68-7.74 (m, 4H), 7.88 (dd, J=8.5, 1.9 Hz, 1H), 8.09 (d, J=8.4 Hz, 1H).

Example 11

1-(2,5-Dichlorophenyl)-4-methyl-N-(pyridin-2-ylmethyl)[1,2,4]triazolo[4,3-a]quinoxaline-8-carboxamide (B-11)

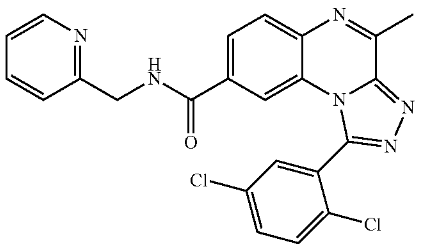 [SMILES: Cc1nc2ccc(C(=O)NCc3ccccn3)cc2n2c(-c3cc(Cl)ccc3Cl)nnc12]

A stainless steel autoclave system was charged under nitrogen atmosphere with: intermediate I-24 (0.475 g, 1.16 mmol), $Pd(AcO)_2$ (0.005 g, 0.023 mmol), XantPhos (0.013 g, 0.023 mmol), $Et_3N$ (0.324 mL, 2.33 mmol), 2-(aminomethyl) pyridine (0.125 g, 1.16 mmol) dissolved in toluene (40 mL). The autoclave was closed and pressurized to 30 bar of CO and the reaction was carried out for 16 h at 150° C. Then the r.m. was cooled down and the solvent evaporated in vacuo. The crude mixture was purified by preparative HPLC on RP (Vydac® Denali® C18-10 μm, 250 g, 5 cm), mobile phase (0.5% amoniumacetate solution in $H_2O$+10% $CH_3CN$, MeOH), yielding a compound that was treated with DCM. Since during the extraction a white suspension was formed between the layers, this solid was collected by filtration and washed with $H_2O$ giving final compound B-11 (0.137 g, 25%). $^1H$ NMR (360 MHz, DMSO-$d_6$) δ ppm 2.98 (s, 3H), 4.45-4.61 (m, 2H), 7.25 (d, J=7.7 Hz, 1H), 7.26-7.30 (m, 1H), 7.77 (td, J=7.7, 1.8 Hz, 1H), 7.82 (d, J=1.5 Hz, 1H), 7.85-7.88 (m, 1H), 7.88-7.93 (m, 1H), 7.98 (d, J=2.2 Hz, 1H), 8.17 (d, J=8.4 Hz, 1H), 8.20-8.25 (m, 1H), 8.51 (br. d, J=5.1 Hz, 1H), 9.34 (br. t, J=6.0, 6.0 Hz, 1H).

Example 12

8-(Ethoxymethyl)-4-methyl-1-phenyl[1,2,4]triazolo[4,3-a]quinoxaline (B-12)

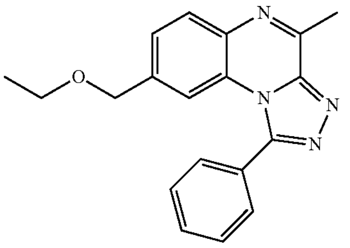 [SMILES: CCOCc1ccc2nc(C)c3nnc(-c4ccccc4)n3c2c1]

To a suspension of Raney-Nickel (0.1 g, 1.7 mmol), in THF (40 mL) under nitrogen atmosphere, intermediate 1-15 (0.059 g, 0.17 mmol) was added. The mixture was stirred at r.t. for 1 h, then the catalyst was removed by filtration over diatomaceous earth and the solvent evaporated in vacuo. The crude product was purified by preparative HPLC on RP (Vydac® Denali® C18-10 μm, 250 g, 5 cm), mobile phase (0.25% $NH_4HCO_3$ solution in $H_2O$, $CH_3CN$). The desired fractions were collected and the solvent was evaporated and co-evaporated with MeOH, yielding two fractions. Since the second fraction was not pure enough, it was re-purified again in the same conditions as before. The first pure fraction isolated and the one from the second purification were combined together and crystallized from DIPE yielding final product B-12 (0.025 g, 46.5%) as solid compound. $^1H$ NMR (360 MHz, DMSO-$d_6$) δ ppm 1.03 (t, J=7.0 Hz, 3H), 2.91 (s, 3H), 3.30-3.39 (m, 2H), 4.42 (s, 2H), 7.40-7.51 (m, 2H), 7.63-7.80 (m, 5H), 7.97 (d, J=8.1 Hz, 1H).

Example 13

1-(2-Chlorophenyl)-4-methyl[1,2,4]triazolo[4,3-a]quinoxalin-8-ol (B-13)

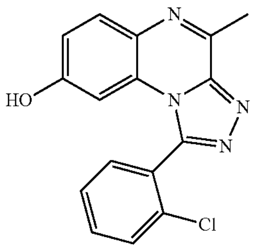 [SMILES: Cc1nc2ccc(O)cc2n2c(-c3ccccc3Cl)nnc12]

To a degassed mixture of final product B-3a (0.1 g, 0.268 mmol), bispinacolate diboron (0.095 g, 0.375 mmol) and potassium acetate (0.078 g, 0.8 mmol) in 1,4-dioxane (3 mL), $Pd(dppf)_2Cl_2$ (0.011 g, 0.016 mmol) was added, and the mixture was heated at 115° C. for 1 h. After this time the r.m. was cooled down to 0° C., then $CH_3COOH$ (0.068 mL, 1.2 mmol) was added, and then $H_2O_2$ (0.041 mL, 0.4 mmol) was added dropwise. The r.m. was allowed to reach r.t. and stirred for 45 min. The mixture was filtered through diatomaceous earth, the organic solvent evaporated in vacuo and then the crude mixture was purified by chromatography (silica, MeOH in EtOAC 0:100 to 3:97) to give final product B-13 as pale brown solid (0.06 g, 72%). $^1H$ NMR (400 MHz, DMSO-$d_6$) δ ppm 2.86 (s, 3H), 6.49 (d, J=2.5 Hz, 1H), 7.06 (dd, J=8.8, 2.5 Hz, 1H), 7.64-7.70 (m, 1H), 7.77-7.84 (m, 3H), 7.86 (d, J=8.8 Hz, 1H), 10.45 (br. s., 1H).

Example 14

1-(2-Chlorophenyl)-8-ethenyl-4-methyl[1,2,4]triazolo[4,3-a]quinoxaline (B-14)

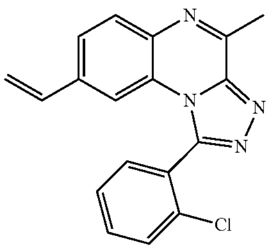 [SMILES: C=Cc1ccc2nc(C)c3nnc(-c4ccccc4Cl)n3c2c1]

A mixture of compound B-3a (0.65 g, 1.74), (tetrakis) triphenylphosphine palladium(0) (0.080 g, 0.07 mmol) and LiCl (0.221 g, 5.21 mmol) in toluene (30 mL) was treated with tributylvinyl tin (0.661 g, 2.088 mmol) and heated in a sealed tube at 120° C. for 1 h (the reaction was divided in two batches). After cooling to r.t. the mixture was partitioned between EtOAc and $H_2O$. The organic phase was washed with brine, separated, dried ($Na_2SO_4$), filtered, and the solvent concentrated in vacuo. The crude compound was purified by chromatography (silica EtOAc in DCM 10/90 to 50/50) giving a light yellow solid that was further washed with DIPE/diethyl ether to yield final compound B-14 as white product (0.52 g, 93.1%). $^1H$ NMR (400 MHz, $CDCl_3$) δ ppm 3.08 (s, 3H), 5.25 (d, J=10.9 Hz, 1H), 5.43 (d, J=17.6 Hz, 1H), 6.53 (dd, J=17.5, 11.0 Hz, 1H), 7.24 (d, J=1.6 Hz, 1H), 7.54-7.62 (m, 2H), 7.64-7.74 (m, 3H), 7.99 (d, J=8.3 Hz, 1H).

Example 15

1-(2-Chlorophenyl)-4-methyl-8-(2-pyridin-2-ylethoxy) [1,2,4]triazolo[4,3-a]quinoxaline (B-15)

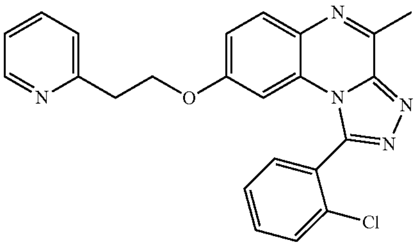 [SMILES: Cc1nc2ccc(OCCc3ccccn3)cc2n2c(-c3ccccc3Cl)nnc12]

A mixture of compound B-13 (1.5 g, 4.83 mmol), 2-(2-hydroxyethyl)pyridine (0.654 mL, 5.79 mmol), di-tert-butylazadicarboxylate (1.33 g, 5.79 mmol) and triphenylphosphine (1.52 g, 5.79 mmol), in THF (36 mL) was heated in a microwave oven for 20 min at 120° C. (the reaction mixture was divided in three batches). Then 1 equiv. more of di-tert-butylazadicarboxylate and triphenylphosphine were added and the r.m. was heated again at the same conditions as before. Then the solvent was evaporated, the crude compound taken up in aq. sat. $NaHCO_3$ and then extracted with DCM. The organic layer was separated, dried ($Na_2SO_4$), filtered and the solvent concentrated in vacuo. The crude mixture was purified by chromatography (silica, MeOH in EtOAc 0:100 to 15:85) to give an oil that was made solid by addition of diethylether to yield final product B-15 as white solid (1.32 g, 65.7%). $^1H$ NMR (500 MHz, $CDCl_3$) δ ppm 3.04 (s, 3H), 3.14 (t, J=6.8 Hz, 2H), 3.91-4.05 (m, 2H), 6.67 (d, J=2.6 Hz, 1H), 7.11 (dd, J=9.2, 2.6 Hz, 1H), 7.17 (d, J=8.4 Hz, 1H), 7.18-7.24 (m, 1H), 7.48-7.54 (m, 2H), 7.56-7.61 (m, 1H), 7.64 (td, J=7.7, 1.9 Hz, 1H), 7.68 (dd, J=5.9, 3.3 Hz, 1H), 7.92 (d, J=9.0 Hz, 1H), 8.57 (d, J=4.3 Hz, 1H).

Example 16

1-(2-Chlorophenyl)-4-methyl-8-(4-methylpiperazin-1-yl)[1,2,4]triazolo[4,3-a]quinoxaline (B-16)

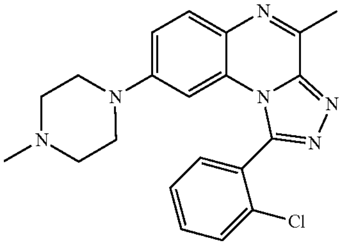

A mixture of final product B-3a (0.1 g, 0.268 mmol), $Pd(AcO)_2$ (0.012 g, 0.053 mmol), 4,5-bis(diphenylphosphino)-9,9-dimethylxanthene (0.061 g, 0.107 mmol), $CsCO_3$ (0.13 g, 0.4 mmol) and N-methyl-piperazine (0.032 g, 0.32 mmol) in a mixture of DMF/1,4-dioxane (1:1, 4 mL) was heated in a microwave oven at 150° C. for 10 min. The solvent was then evaporated; the crude compound was taken up in $H_2O$ and extracted with DCM. The organic layer was separated, dried ($Na_2SO_4$), filtered and the solvent concentrated in vacuo. The crude compound was purified by chromatography (silica, MeOH—$NH_3$ (7 M) in DCM from 2:98 to 5:95) to give the desired compound only 65% pure, thus, the product was further purified by preparative HPLC on RP (C18 XBridge™ 19×100 5 μm), mobile phase (Gradient from 80% 0.1% $NH_4CO_3H/NH_4OH$ pH 9 solution in $H_2O$, 20% $CH_3CN$ to 0% 0.1% $NH_4CO_3H/NH_4OH$ pH 9 solution in $H_2O$, 100% $CH_3CN$), yielding final compound B-16 as pale yellow solid (0.019 g, 17.4%). $^1H$ NMR (500 MHz, $CDCl_3$) δ ppm 2.31 (s, 3H), 2.43 (t, J=5.1 Hz, 4H), 2.91-3.02 (m, 4H), 3.03 (s, 3H), 6.59 (d, J=2.3 Hz, 1H), 7.13 (dd, J=9.2, 2.6 Hz, 1H), 7.54 (td, J=7.5, 1.4 Hz, 1H), 7.61 (td, J=7.5, 1.4 Hz, 1H), 7.63-7.66 (m, 1H), 7.69 (dd, J=7.5, 1.4 Hz, 1H), 7.87 (d, J=9.0 Hz, 1H).

Example 17a and 17b 1-(5-Butoxypyridin-3-yl)-4-methyl-8-(morpholin-4-ylmethyl) [1,2,4]triazolo[4,3-a]quinoxaline hydrochloride (B-17a) and oxalate (B-17b)

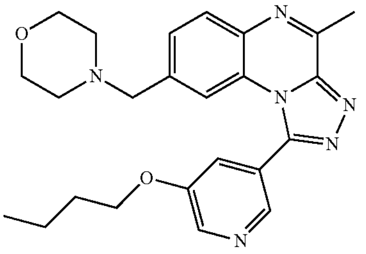

.2 HCl (B-17a) or .x $C_2H_2O_4$ (B-17b)

Formation of B-17a

To a solution of compound B-7 (7.5 g, 18.19 mmol) in THF/$H_2O$ (10:1, 180 mL), $Pd(AcO)_2$ (0.12 g, 0.54 mmol), XantPhos (0.52 g, 1.09 mmol), $Cs_2CO_3$ (23.88 g, 72.76 mmol) and intermediate compound I-17 (4.51 g, 21.82 mmol) were added. The r.m. was closed in a sealed tube and stirred at r.t. for 10 min and then at 114° C. for 45 min. Then, the crude mixture was diluted with EtOAc and $H_2O$, the organic layer separated, dried ($MgSO_4$), filtered and the solvent concentrated in vacuo. The crude mixture was purified by chromatography (silica, MeOH in DCM 0/100 to 2/98) the desired fractions were collected and the solvent concentrated in vacuo to give a pale red oil. This material was then dissolved in EtOAc (50 mL) and treated dropwise with HCl (4 M in dioxane, 1.2 eq, and 3.55 mL). The mixture was stirred at room temperature for 30 min and then evaporated under vacuum. The slurry was treated with 120 mL of DIPE and stirred again for additional 40 min. The formed precipitate was filtered off, washed with DIPE, dried under vacuum to yield final compound B-17a as a hydrochloride salt (5.2 g, 61%) $^1$H NMR (400 MHz, DMSO-$d_6$) δ ppm 0.94 (t, J=7.5 Hz, 3H), 1.46 (sxt, J=7.4 Hz, 2H), 1.69-1.82 (m, 2H), 2.88-3.04 (m, 2H), 2.96 (s, 3H), 3.19 (br. d, J=12.5 Hz, 2H), 3.75-3.98 (m, 4H), 4.18 (t, J=6.5 Hz, 2H), 4.34 (br. s., 2H), 7.68 (d, J=1.2 Hz, 1H), 8.00 (dd, J=8.5, 1.6 Hz, 1H), 8.09 (dd, J=2.4, 1.6 Hz, 1H), 8.13 (d, J=8.1 Hz, 1H), 8.70 (d, J=1.6 Hz, 1H), 8.75 (d, J=2.8 Hz, 1H), 12.03 (br. s., 1H).

Formation of B-17b

To a stirred solution of intermediate 1-30 (0.108 g, 0.3 mmol), morpholine (0.03 mL, 0.33 mmol) and acetic acid (0.017 mL, 0.3 mmol) in DCE (5 mL) was added triacetoxy sodium borohydride (0.076 g, 0.3 mmol) and the mixture was stirred at room temperature overnight. Water and ethyl acetate were added, and the organic phase was separated, dried ($MgSO_4$), filtered and concentrated in vacuo. The crude mixture was purified by chromatography (silica, MeOH in DCM 0/100 to 10/90), the desired fractions were collected and concentrated in vacuo. The product was dissolved in dioxane (2 mL), oxalic acid was added (0.024 g, 0.27 mmol), the mixture was stirred for 45 min, concentrated in vacuo and recrystallized from diethyl ether to yield final compound B-17b as an oxalate salt (0.084 g, 54%).

(Spectrum of the free base) $^1$H NMR (300 MHz, DMSO-$d_6$) δ ppm 0.93 (t, J=7.4 Hz, 3H), 1.45 (sxt, J=7.4 Hz, 2H), 1.67-1.82 (m, 2H), 2.37 (br. s., 4H), 2.93 (s, 3H), 3.50 (br. s., 4H), 3.60 (s, 2H), 4.11 (t, J=6.5 Hz, 2H), 7.54 (s, 1H), 7.55 (d, J=8.8 Hz, 1H), 7.88 (br. s, 1H), 8.01 (d, J=8.1 Hz, 1H), 8.54 (s, 1H), 8.66 (d, J=2.5 Hz, 1H).

Example 18

1-(5-Butoxy-2-chlorophenyl)-4-methyl-8-(morpholin-4-ylmethyl) [1,2,4]triazolo-[4,3-a]quinoxaline hydrochloride (B-18)

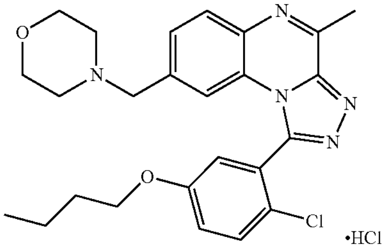 [SMILES: CCCCOc1ccc(Cl)c(-c2nnc3c(C)nc4ccc(CN5CCOCC5)cc4n23)c1 ; Cl]

•HCl

B-18 was synthesized as previously described for the synthesis of final compound B-17a. Starting from B-6a (0.2 g, 0.45 mmol) and intermediate compound I-17 final compound B-18 was obtained (0.03 g, 14%). $^1$H NMR (300 MHz, DMSO-$d_6$) δ ppm 0.93 (t, J=7.4 Hz, 3H), 1.44 (sxt, J=7.3 Hz, 2H), 1.73 (quin, J=6.9 Hz, 2H), 2.93 (br. s., 1H), 2.97 (s, 3H), 3.19 (br. s., 1H), 3.77 (br. s., 2H), 3.92 (br. s., 2H), 3.98-4.14 (m, 2H), 4.31 (br. s., 2H), 5.76 (s, 2H), 7.25 (br. s, 1H), 7.33-7.50 (m, 2H), 7.73 (d, J=8.8 Hz, 1H), 7.96 (br. s., 1H), 8.16 (d, J=8.1 Hz, 1H), 11.31 (br. s., 1H).

Example 19

1-(2-Chlorophenyl)-4-methyl-8-(morpholin-4-ylmethyl)[1,2,4]triazolo[4,3-a]-quinoxaline (B-19)

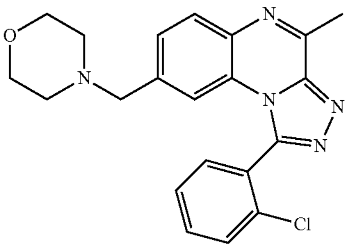 [SMILES: Cc1nc2ccc(CN3CCOCC3)cc2n2c(-c3ccccc3Cl)nnc12]

Morpholine (1.37 mL, 15.67 mmol) was added to a stirred solution of intermediate I-16 (2.3 g, 7.12 mmol) dissolved in DCE (50 mL) and the mixture was heated at 80° C. for 15 min under microwave irradiation (the reaction was divided in three batches). Then triacetoxy sodium borohydride (1.81 g, 8.55 mmol) was added portionwise and the mixture was heated again at the same conditions as before for 20 min. The mixture was then quenched with $H_2O$ and extracted with DCM. The organic layer was separated, dried ($Na_2SO_4$), filtered and the solvent evaporated in vacuo. The crude compound was purified by chromatography (silica, MeOH in EtOAC 2/98 to 10/90) the desired fractions were collected and the solvent evaporated to yield final compound B-19 as pale yellow solid that was further washed with diethyl ether/DIPE (1.6 g, 57%). $^1H$ NMR (400 MHz, $CDCl_3$) δ ppm 2.24-2.41 (m, 4H), 3.08 (s, 3H), 3.42 (s, 2H), 3.53-3.69 (m, 4H), 7.37 (d, J=1.2 Hz, 1H), 7.49 (dd, J=8.3, 1.6 Hz, 1H), 7.54-7.62 (m, 1H), 7.64-7.75 (m, 3H), 7.99 (d, J=8.3 Hz, 1H).

Example 20

N-{[1-(2-Chlorophenyl)-4-methyl[1,2,4]triazolo[4,3-a]quinoxalin-8-yl]methyl}-ethanamine (B-20)

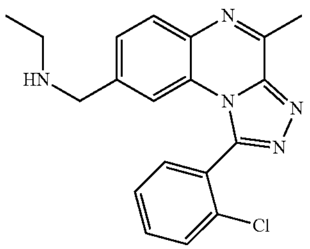 [SMILES: CCNCc1ccc2nc(C)c3nnc(-c4ccccc4Cl)n3c2c1]

Intermediate I-16 (0.300 g, 0.93 mmol), ethylamine hydrochloride (0.227 mL, 2.78 mmol) and $Et_3N$ (0.388 mL, 2.78 mmol) were dissolved in DCE (11 mL). To this mixture 300 mg of $MgSO_4$ was added and everything was stirred at r.t. for 1.3 h. The solid was filtered off, and then MeOH (3 mL) followed by $NaBH_4$ (0.07 g, 1.85 mmol) were added to the filtrate and the solution was stirred at r.t. for additional 15 min. The r.m. was quenched with $H_2O$ and extracted with DCM. The organic layers were separated, dried ($MgSO_4$), filtered and the solvent concentrated in vacuo. The crude mixture was purified by chromatography (silica; MeOH in DCM 0/100 to 10/90) yielding final compound B-20 as solid material (0.186 g, 57%). $^1H$ NMR (500 MHz, $CDCl_3$) δ ppm 1.03 (t, J=7.1 Hz, 3H), 2.45-2.57 (m, 2H), 3.08 (s, 3H), 3.69-3.79 (m, 2H), 7.27 (br. s., 1H), 7.50 (d, J=8.4 Hz, 1H), 7.53-7.59 (m, 1H), 7.61-7.68 (m, 2H), 7.70 (d, J=6.9 Hz, 1H), 7.99 (d, J=8.1 Hz, 1H).

Example 21

1-[1-(2-Chlorophenyl)-4-methyl[1,2,4]triazolo[4,3-a]quinoxalin-8-yl]-2,2,2-trifluoroethanol (B-21)

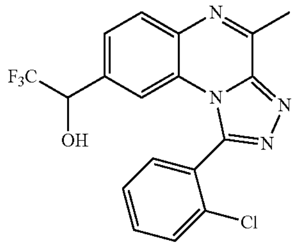 [SMILES: Cc1nc2ccc(C(O)C(F)(F)F)cc2n2c(-c3ccccc3Cl)nnc12]

Trimethyl(trifluoromethyl) silane (0.105 g, 0.74 mmol) was added to a stirred suspension of intermediate 1-16 (0.2 g, 0.62 mmol) containing a catalytic amount of CsF (0.003 g, 0.025 mmol) in 1,2-dimethoxyethane (4 mL) at r.t. and under argon atmosphere. After being stirred for 30 min at r.t., the mixture was treated with HCl (1M in $H_2O$, 1.24 mL) and stirred for further 15 min. Then the r.m. was diluted with EtOAc, the organic layer was separated, dried ($Na_2SO_4$), filtered and the solvent concentrated in vacuo. The crude product was purified by chromatography (silica, EtOAc in DCM 50/50) to give final compound B-21 as pale yellow solid (0.12 g, 49.3%). (1:1 mixture of rotamers) $^1H$ NMR (400 MHz, DMSO-$d_6$) δ ppm 2.95 (s, 3H), 5.06-5.25 (m, 1H), 6.86 (br. s., 0.5H), 6.94 (br. s., 0.5H), 7.32 (s, 0.5H), 7.38 (s, 0.5H), 7.63-7.71 (m, 2H), 7.71-7.76 (m, 1H), 7.76-7.86 (m, 4H), 8.07 (dd, J=8.3, 4.4 Hz, 1H).

Example 22

1-(2-Chlorophenyl)-4-methyl-8-(2,2,2-trifluoro-1-morpholin-4-ylethyl) [1,2,4]triazolo[4,3-a]quinoxaline (B-22)

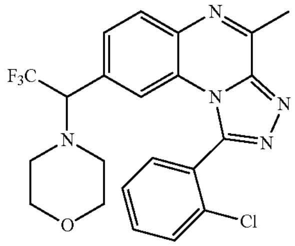 [SMILES: Cc1nc2ccc(C(N3CCOCC3)C(F)(F)F)cc2n2c(-c3ccccc3Cl)nnc12]

Methanesulphonyl chloride (0.079 mL, 1.02 mmol) was added to a stirred solution of final product B-21 (0.08 g, 0.2 mmol) and pyridine (0.161 mL, 2.04 mmol) dissolved in DCM (1 mL). The mixture was stirred at r.t. overnight, then it was basified with $NaHCO_3$ (sat. sol) and extracted with DCM. The organic layer was separated, dried ($Na_2SO_4$), filtered and the solvent concentrated in vacuo. Then, morpholine (0.528 mL, 6.11 mmol) was added to the crude residue and the r.m. was stirred at r.t. 4 h. The crude mixture was then diluted with $H_2O$ and extracted with DCM, the organic layer was separated, dried ($Na_2SO_4$), filtered and the solvent concentrated in vacuo. The crude product was purified by chromatography (silica, MeOH in EtOAc 0/100 to 5/95, and then with EtOAC in heptane 70/30 to 100/0) to give the desired compound only 75% pure. Thus the material was further purified by preparative HPLC on RP (C18 XBridge™ 19×100 5 μm), mobile phase (Gradient from 80% 0.1% $NH_4CO_2CH_3$ solution in $H_2O$, 20% $CH_3CN$ to 0% 0.1% $NH_4CO_2CH_3$ solution in $H_2O$, 100% $CH_3CN$), yielding final compound B-22 as white solid (0.007 g, 7.1%). (1:1 mixture of rotamers) $^1H$ NMR (400 MHz, $CDCl_3$) δ ppm 2.37-2.45 (m, 2H), 2.45-2.53 (m, 2H), 3.10 (s, 3H), 3.51-3.57 (m, 2H), 3.58-3.70 (m, 2H), 3.86-3.97 (m, 1H), 7.41 (d, J=1.2 Hz, 0.5H), 7.44 (br. s, 0.5H), 7.49-7.55 (m, 1H), 7.55-7.61 (m, 1H), 7.63-7.68 (m, 2H), 7.68-7.72 (m, 1H), 8.07 (dd, J=8.3, 1.8 Hz, 1H).

Example 23

1-(2-Chloro-6-fluorophenyl)-4-methyl-8-(morpholin-4-ylmethyl) [1,2,4]triazolo[4,3-a]quinoxaline (B-23)

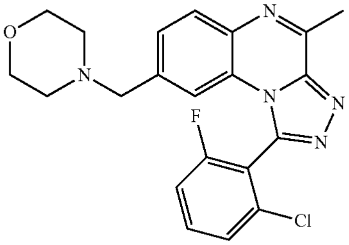 [SMILES: Cc1nc2ccc(CN3CCOCC3)cc2n2c(-c3c(F)cccc3Cl)nnc12]

Morpholine (0.056 mL, 0.64 mmol) was added to a stirred solution of Intermediate I-22 (0.1 g, 0.29 mmol) dissolved in DCE (5 mL) and the mixture was heated at 120° C. for 15 min under microwave irradiation. Then sodium triacetoxy borohydride (0.075 g, 0.35 mmol) was added portionwise and the mixture was heated again at 80° C. for 20 min under microwave irradiation. The r.m. was then quenched with $H_2O$ and extracted with DCM. The organic layer was separated, dried ($Na_2SO_4$), filtered and the solvent evaporated in vacuo. The crude compound was purified by chromatography (silica, MeOH in EtOAc 2/98 to 10/90) the desired fractions were collected and the solvent evaporated to yield final compound B-23 as pale yellow solid that was further washed with diethyl ether/DIPE (0.045 g, 37%). $^1H$ NMR (400 MHz, CHLOROFORM-d) δ ppm 2.25-2.41 (m, 4H) 3.09 (s, 3H) 3.39-3.52 (m, 2H) 3.54-3.68 (m, 4H) 7.32 (t, J=8.3 Hz, 1H) 7.41 (br. s, 1H) 7.47-7.51 (m, 1H) 7.52 (d, J=8.3 Hz, 1H) 7.68 (td, J=8.3, 5.8 Hz, 1H) 8.01 (d, J=8.3 Hz, 1H).

Example 24

Cyclopropyl [4-methyl-1-(4-methylpyridin-3-yl) [1,2,4]triazolo[4,3-a]quinoxalin-8-yl]methanone (B-24)

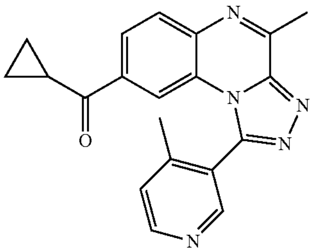 [SMILES: Cc1ccncc1-c1nnc2c(C)nc3ccc(C(=O)C4CC4)cc3n12]

Intermediate I-28 (0.079 g, 0.231 mmol), was dissolved in DCM (0.6 mL), and $MnO_2$ (0.1 g, 1.155 mmol) was added. The mixture was stirred at r.t. for 4 h. The r.m. was then filtered over diatomaceous earth and concentrated under vacuum. The crude product was then purified by flash chromatography but since the compound was not pure enough the material was further purified by RP HPLC on (C18, LUNA® 19×100 5 μm), mobile phase (25 mM $NH_4HCO_3$ solution in $H_2O$, MeOH+$CH_3CN$) yielding final compound B-24 as amorphous solid that was further triturated with pentane (0.007 g, 9%).

Example 25

1-(2-Chlorophenyl)-8-(1,1-difluoroethoxy)-4-methyl [1,2,4]triazolo[4,3-a]-quinoxaline (B-25)

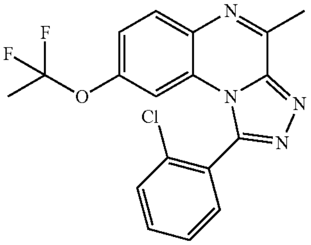 [SMILES: Cc1nc2ccc(OC(C)(F)F)cc2n2c(-c3ccccc3Cl)nnc12]

In a polyethylene vial, Xenon difluoride (0.1 g, 0.59 mmol) followed by hydrogen fluoride-pyridine complex (1.26 g, 8.9 mmol) were added to a solution of intermediate 1-23 (0.1 g, 0.29 mmol) dissolved in DCM (1 mL). The vial was sealed and stirred overnight at r.t. After this time the r.m. was diluted with DCM (10 mL) and quenched by slow addition of NaOH (2M in $H_2O$) until basic pH. The organic phase was then separated, dried ($Na_2SO_4$), filtered and concentrated in vacuo. The crude compound was purified by chromatography (silica, EtOAc in $CH_2Cl_2$ 30/70 to 50/50), the desired fractions were collected and concentrated in vacuo, the solid compound obtained was then washed with DIPE to give final product B-25 as pale yellow solid (0.03 g, 27%). $^1H$ NMR (400 MHz, $CDCl_3$) δ ppm 1.85 (t, J=13.5 Hz, 3H) 3.08 (s, 3H) 7.13 (d, J=2.8 Hz, 1H) 7.32 (dd, J=8.8, 2.5 Hz, 1H) 7.52-7.59 (m, 1H) 7.62-7.71 (m, 3H) 8.02 (d, J=8.8 Hz, 1H).

Example 26

1-(5-Butoxy-2-chlorophenyl)-4-methyl-8-(4-methyl-piperazin-1-yl) [1,2,4]triazolo-[4,3-a]quinoxaline (B-26)

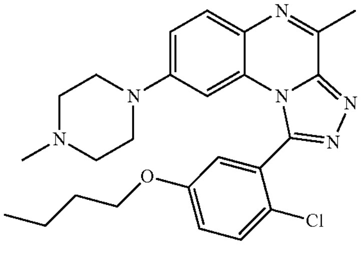 [SMILES: CCCCOc1ccc(Cl)c(-c2nnc3c(C)nc4ccc(N5CCN(C)CC5)cc4n23)c1]

To a solution of compound B-6a (0.23 g, 0.51 mmol) in toluene (5 mL), $Pd_2(dba)_3$ (0.014 g), XantPhos (0.024 g, 0.05 mmol) and $Cs_2CO_3$ (0.33 g, 1.03 mmol) were added. The r.m. was stirred for 10 min at r.t. and then N-methyl-piperazine (0.062 mL, 0.56 mmol) was added. Then, the r.m. was stirred in a sealed tube at 100° C. for 5 h. After cooling to r.t. the mixture was then diluted with EtOAc and $H_2O$, the organic phase was separated, dried ($Na_2SO_4$), filtered and concentrated in vacuo. The crude compound was purified by chromatography (silica, MeOH in DCM 0/100 to 3/97), the desired fractions were collected and concentrated in vacuo, and the solid compound obtained was then re-crystallized with DIPE-MeOH (~40:1) yielding final compound B-26 (0.077 g, 32%). $^1$H NMR (300 MHz, DMSO-$d_6$) δ ppm 0.91 (t, J=7.4 Hz, 3H), 1.42 (sxt, J=7.3 Hz, 2H), 1.62-1.78 (m, 2H), 2.17 (s, 3H), 2.30 (br. t, J=4.3, 4.3 Hz, 4H), 2.85 (s, 3H), 2.94 (br. d, J=3.3 Hz, 2H), 4.05 (t, J=6.5 Hz, 2H), 6.43 (d, J=1.9 Hz, 1H), 7.23-7.38 (m, 2H), 7.43 (d, J=2.7 Hz, 1H), 7.71 (d, J=8.9 Hz, 1H), 7.82 (d, J=9.1 Hz, 1H).

Example 27

1-(2-Chlorophenyl)-4-methyl[1,2,4]triazolo[4,3-a]quinoxalin-8-amine (B-27)

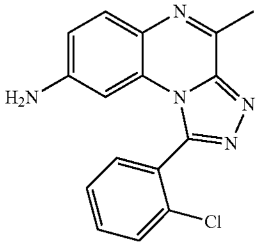 [SMILES: Cc1nc2ccc(N)cc2n2c(-c3ccccc3Cl)nnc12]

To a solution of compound B-3a (0.05 g, 0134 mmol) in toluene (2 mL), sodium tert-butoxide (0.018 g, 0.19 mmol), (±) BINAP (0.013 g, 0.021 mmol), $Pd_2(dba)_3$ (0.008 g, 0.009 mmol) and benzophenone imine (0.03 mL, 0.174 mmol) were added at r.t. The r.m. was then heated at 120° C. for 1 h. After cooling, a solution of HCl (1 M in $H_2O$)/THF (1:1, 10 mL) was added and the mixture was stirred for an additional h. Then, the mixture was washed with EtOAc, the aq. layer was basified with $NaHCO_3$ (sat. sol.) and extracted with EtOAc. The combined organic layers were separated, dried ($Na_2SO_4$), filtered and concentrated in vacuo. The residue was purified by chromatography (MeOH—$NH_3$ in DCM from 0/100 to 5/95) to give final product B-27 as pale yellow solid (0.015 g, 36.2%). $^1$H NMR (400 MHz, $CDCl_3$) δ ppm 3.01 (s, 3H), 3.88 (br. s, 2H), 6.36 (d, J=2.5 Hz, 1H), 6.86 (dd, J=8.8, 2.3 Hz, 1H), 7.49-7.58 (m, 1H), 7.61-7.65 (m, 2H), 7.65-7.69 (m, 1H), 7.82 (d, J=8.6 Hz, 1H).

Example 28

N-[1-(2-Chlorophenyl)-4-methyl[1,2,4]triazolo[4,3-a]quinoxalin-8-yl]propanamide (B-28)

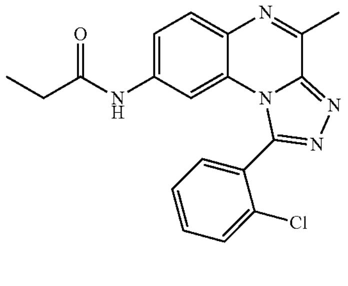 [SMILES: CCC(=O)Nc1ccc2nc(C)c3nnc(-c4ccccc4Cl)n3c2c1]

To a solution of propionic acid (0.055 g, 0.178 mmol), HATU (0.08 g, 0.213 mmol) and DIPEA (0.036 mL, 0.213 mmol) in DMF (1 ml) was added a solution of B-27 (0.055 g, 0.178 mmol) in DCM. The r.m. was stirred at r.t. for 2 h and then quenched with $H_2O$ and extracted with DCM. The organic extracts were separated, dried ($Na_2SO_4$) and evaporated till dryness. The crude compound was purified by chromatography (silica, MeOH in DCM 0/100 to 5/95) to give the desired compound only 92% pure. This material was further purified by RP HPLC on C18 (XBridge™ 19×100 5 μm). Mobile phase (Gradient from 80% 0.1% $NH_4CO_3H/NH_4OH$ pH 9 solution in $H_2O$, 20% $CH_3CN$ to 0% 0.1% $NH_4CO_3H/NH_4OH$ pH 9 solution in $H_2O$, 100% $CH_3CN$), yielding final compound B-28 as white solid (0.007 g, 11%). $^1$H NMR (500 MHz, DMSO-$d_6$) δ ppm 0.99 (t, J=7.7 Hz, 3H), 2.24 (q, J=7.5 Hz, 2H), 2.89 (s, 3H), 7.46 (dd, J=8.7, 2.0 Hz, 1H), 7.60-7.68 (m, 1H), 7.75 (d, J=7.5 Hz, 1H), 7.77 (d, J=3.8 Hz, 2H), 7.95 (d, J=8.7 Hz, 1H), 8.15 (d, J=1.7 Hz, 1H), 10.20 (s, 1H).

Example 29

(4-Methyl-1-phenyl[1,2,4]triazolo[4,3-a]quinoxalin-8-yl)methanol (B-29)

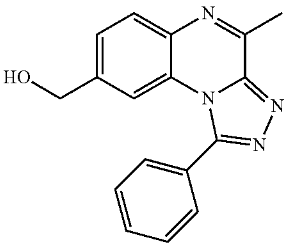 [SMILES: Cc1nc2ccc(CO)cc2n2c(-c3ccccc3)nnc12]

Compound B-2a (1 g, 3 mmol) was dissolved in THF (10 mL) and then lithium aluminium hydride (1M in diethyl ether, 9 mL) was added dropwise at 0° C. The r.m. was stirred at this temperature for 30 min. The mixture was then quenched with $NH_4Cl$ (sat. sol.) and extracted with DCM. The organic layer was separated, dried ($Na_2SO_4$) and the solvent evaporated in vacuo. The crude residue was purified by chromatography (silica, MeOH in EtOAc 0/100 to 0/90) to give a sticky oil that was found to be an over-reduced product (the compound was reduced both in the carboxyl moiety and in one of the double bonds of the aromatic system). Thus, this material (0.7 g, 2.4 mmol) was dissolved in toluene (30 mL) and Pd—C (10%, 0.2 g) was added. The reaction mixture was heated in a sealed tube at 150° C. for 5 h. Then the r.m. was filtered off over a diatomaceous earth pad, and the filtrate washed several times with a solution of DCM/MeOH (9:1) to give the desired compound 50% pure. This material was further purified by RP HPLC on C18 (XBridge™ 30×100 5 μm). Mobile phase (Gradient from 80% 0.1% $NH_4CO_3H/NH_4OH$ pH 9 solution in $H_2O$, 20% $CH_3CN$ to 0% 0.1% $NH_4CO_3H/NH_4OH$ pH 9 solution in $H_2O$, 100% $CH_3CN$), yielding compound B-29 as white solid (0.02 g, 3%). $^1$H NMR (400 MHz, $CDCl_3$) δ ppm 1.73 (t, J=5.9 Hz, 1H), 3.07 (s, 3H), 4.64 (d, J=5.8 Hz, 2H), 7.49-7.56 (m, 2H), 7.58-7.75 (m, 5H), 8.02 (d, J=8.3 Hz, 1H).

Example 30

1-(2-Chlorophenyl)-4-methyl-8-(pyridin-4-yloxy)[1,2,4]triazolo[4,3-a]quinoxaline (B-30)

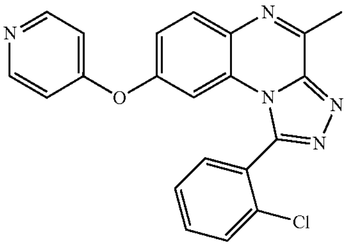 [SMILES: Cc1nc2ccc(Oc3ccncc3)cc2n2c(-c3ccccc3Cl)nnc12]

Potassium hexamethyldisilazide (KHMDS) (0.258 g, 1.3 mmol) was added to a stirred solution of B-13 (0.1 g, 0.322 mmol) in DMF (1.2 mL) and the r.m. was stirred at r.t. for 10 min. To this mixture 4-chloropyridine hydrochloride (0.063 g, 0.418 mmol) and then $K_2CO_3$ (0.054 g, 0.386 mmol) were added and the mixture was heated in a sealed tube at 180° C. for 5 h. The r.m. was quenched with $H_2O$ and extracted with DCM. The organic layer was separated, dried ($Na_2SO_4$), filtered and the solvent evaporated in vacuo. The crude product was purified by chromatography (silica; MeOH in EtOAc 0/100 to 5/95), the desired fractions were collected and concentrated in vacuo to give a yellow oil that was made solid by addition of diethyl ether. The solid compound obtained was filtered off, washed again with diethyl ether to yield finally B-30 as pale yellow solid (0.02 g, 16%). $^1H$ NMR (400 MHz, $CDCl_3$) δ ppm 3.08 (s, 3H), 6.73 (d, J=2.3 Hz, 1H), 6.82-6.87 (m, 2H), 7.32-7.36 (m, 1H), 7.36-7.39 (m, 1H), 7.39-7.49 (m, 2H), 7.58 (dd, J=7.3, 1.7 Hz, 1H), 8.10 (d, J=9.0 Hz, 1H), 8.50-8.56 (m, 2H).

1-(5-Butoxypyridin-3-yl)-4-methyl-8-(morpholin-4-yl-[$^3H$]methyl)[1,2,4]triazolo[4,3-a]quinoxaline ([$^3H$]B-17a)

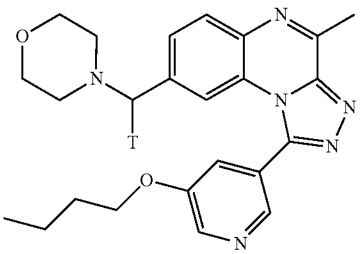

Intermediate compound I-30 (0.002 g, 5.53 μmol) was dissolved in dichloromethane (0.1 mL) in a dry wheaton vial. Morpholine (0.271 mL, 27.67 μmol) and titanium tetra(isopropoxide) (0.82 mL, 27.67 μmol) were added under argon atmosphere and stirred overnight at room temperature. The reaction mixture was transferred to a tritiation ampoule and attached to a tritium manifold (RC Tritec). Dichloromethane was lyophilized of and replaced by dry THF (0.2 mL). The mixture was lyophilized again and Platinum on carbon (4 mg, 5%) was added together with dry THF (0.2 mL). The reaction mixture was degassed (3×) and placed under tritium atmosphere (750 mbar at room temperature) for 60 minutes at room temperature. The tritium atmosphere was removed and the volatile components lyophilized to a waste ampoule. The crude mixture was rinsed and lyophilized with MeOH (3×0.15 mL), filtered over an Acrodisk® and dissolved in ethanol (10 mL). This stock solution was purified over prep-HPLC and resulted in 230 MBq with a radiochemical purity of >98% and specific activity of 726 GBq/mmol.

Radiosynthesis Production of [$^{18}F$]fluoride and of 1-(2-Chloro-6-[$^{18}F$]fluorophenyl)-4-methyl-8-(morpholin-4-ylmethyl)[1,2,4]triazolo[4,3-a]quinoxaline ([$^{18}F$]B-23)

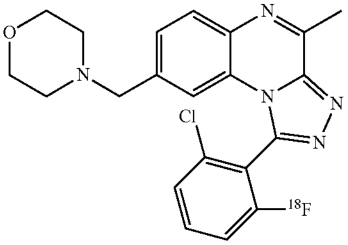 [SMILES: Cc1nc2ccc(CN3CCOCC3)cc2n2c(-c3c([18F])cccc3Cl)nnc12]

[$^{18}F$]fluoride ([$^{18}F]F^-$) was produced by an [$^{18}O(p,n)^{18}F$] reaction by irradiation of 2 mL of 97% enriched [$^{18}O]H_2O$ (Rotem HYOX18, Rotem Industries, Beer Sheva, Israel) in a niobium target using 18-MeV protons from a Cyclone 18/9 cyclotron (Ion Beam Applications, Louvain-la-Neuve, Belgium). After irradiation, the resultant [$^{18}F]F^-$ was separated from [$^{18}O]H_2O$ using a SepPak™ Light Accell plus QMA anion exchange cartridge (Waters, $CO_3^{2-}$ form). [18F]$F^-$ was eluted from the cartridge using a mixture of 0.38 mL of a solution containing $K_2CO_3$ (0.00247 g) and Kryptofix 222 (0.00279 g) dissolved in $H_2O$/MeCN (0.75 mL; 5:95 v/v) and 0.38 mL MeCN. The solution was evaporated under a stream of helium at 80° C. and 35 watt by applying microwave heating and further dried by azeotropic distillation using MeCN (1 mL) at a temperature of 80° C. and a power of 35 watt in the microwave cavity. The precursor for the radiolabeling, I-35 (0.0013 g, 0.0029 mmol) was dissolved in anhydrous DMF (0.35 mL), this solution was added to the dried [$^{18}F]F^-/K_2CO_3$/Kryptofix® 222 complex, and the nucleophilic substitution reaction was carried out using microwave heating at 140° C. and 50 watt for 6 min. Next, the crude mixture was diluted with 0.05 M NaOAc buffer pH 5.5 (0.6 mL) and injected onto the HPLC system consisting of a semi-preparative XBridge™ column ($C_{18}$, 5 μm, 4.6 mm×150 mm; Waters) that was eluted with a mixture of 0.05 M NaOAc buffer pH 5.5 and EtOH (73:27 v/v) at a flow rate of 1 mL/min. UV detection of the HPLC eluate was performed at 254 nm. The radiolabeled product [$^{18}$]B-23 was collected after about 25 min. The collected peak corresponding to [$^{18}$]B-23 was then diluted with saline (Mini Plasco®, Braun, Melsungen, Germany) to obtain a final EtOH concentration of <10% and the solution was sterile filtered through a 0.22 μm membrane filter (Millex®-GV, Millipore). The purity of the radiotracer was analyzed using an HPLC system consisting of an XBridge™ column ($C_{18}$, 5 μm, 4.6 mm×150 mm; Waters) eluted with a mixture of 0.05 M NaOAc buffer pH 5.5 and EtOH (65:35 v/v) at a flow rate of 1 mL/min (Rt=7.5 min). UV detection of the HPLC eluate was performed at 254 nm. [$^{18}F$]B-23 was synthesized in 45% radiochemical yield (relative to starting radioactivity

[$^{18}F]F^-$, decay corrected, n=6). The radiochemical purity as examined using the above described analytical HPLC system was >99% and the average specific radioactivity was found to be 215 GBq/μmol at EOS (n=6).

TABLE 1

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

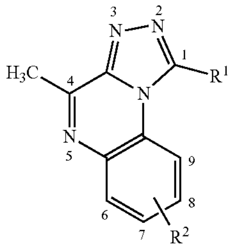

| Co. no. | Ex. no. | $R^1$ | $R^2$ | Salt form |
|---|---|---|---|---|
| B-1a | E1* | 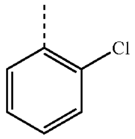 | 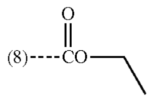 | |
| B-1b | E1* | 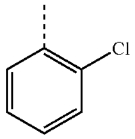 | 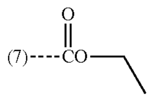 | |
| B-2a | E2* | 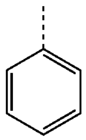 | 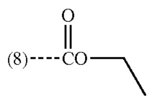 | |
| B-2b | E2* | 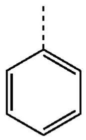 | 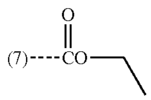 | |
| B-3a | E3* | 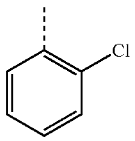 | (8)----Br | |
| B-3b | E3* | 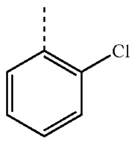 | (7)----Br | |
| B-4a | E4* | 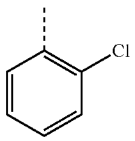 | (8)----$OCF_3$ | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

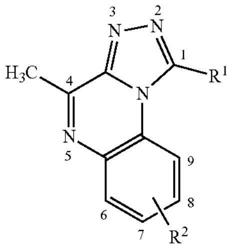

| Co. no. | Ex. no. | $R^1$ | $R^2$ | Salt form |
|---|---|---|---|---|
| B-4b | E4* | 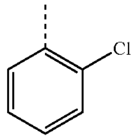 | (7)----$OCF_3$ | |
| B-5 | E5* | 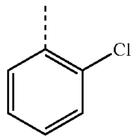 | (8)----OMe | |
| B-6a | E6* | 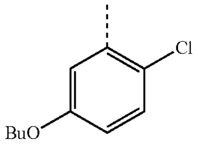 | (8)----Br | |
| B-6b | E6* | 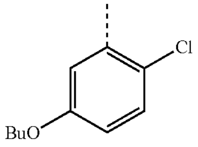 | (7)----Br | |
| B-7 | E7* | 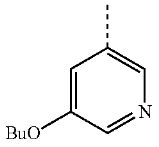 | (8)----Br | |
| B-8 | E8* | 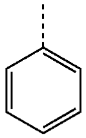 | 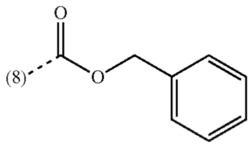 | |
| B-9 | E9* | 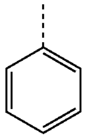 | 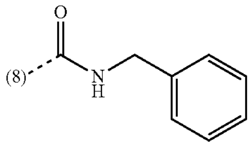 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

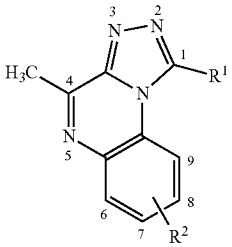

| Co. no. | Ex. no. | $R^1$ | $R^2$ | Salt form |
|---|---|---|---|---|
| B-10 | E10* | 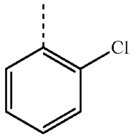 | 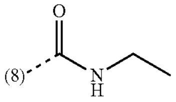 | |
| B-11 | E11* | 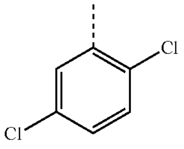 | 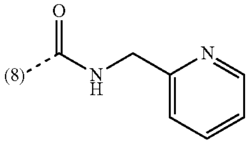 | |
| B-12 | E12* | 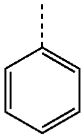 | 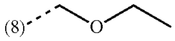 | |
| B-13 | E13* | 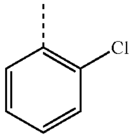 | (8)----OH | |
| B-14 | E14* | 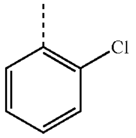 | 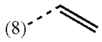 | |
| B-15 | E15* | 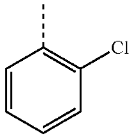 | 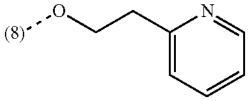 | |
| B-16 | E16* | 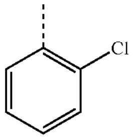 | 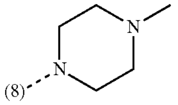 | |
| B-17a | E17a* | 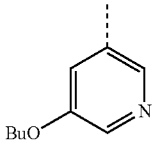 | 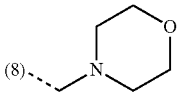 | .2HCl |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

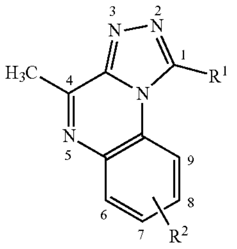

| Co. no. | Ex. no. | $R^1$ | $R^2$ | Salt form |
|---|---|---|---|---|
| $[^3H]$B-17a | $[^3H]$B-17a* | 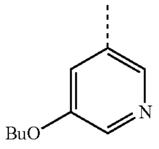 | 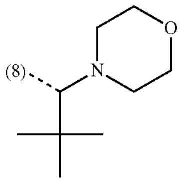 | |
| B-17b | E17b* | 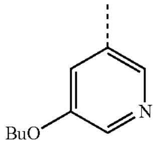 | 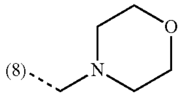 | .x $C_2H_2O_4$ |
| B-18 | E18* | 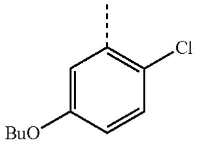 | 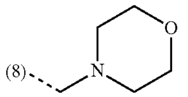 | .HCl |
| B-19 | E19* | 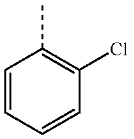 | 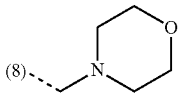 | |
| B-20 | E20* | 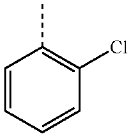 | 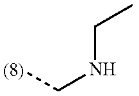 | |
| B-21 | E21* | 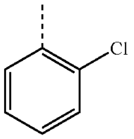 | 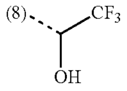 | |
| B-22 | E22* | 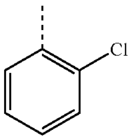 | 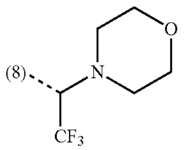 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

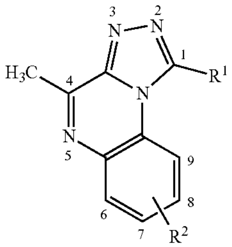

| Co. no. | Ex. no. | $R^1$ | $R^2$ | Salt form |
|---|---|---|---|---|
| B-23 | E23* | 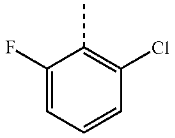 | 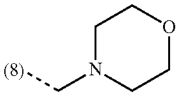 | |
| [$^{18}$F]B-23 | [$^{18}$F]B-23* | 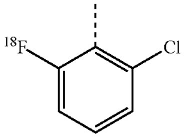 | 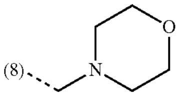 | |
| B-24 | E24* | 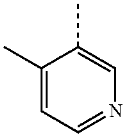 | 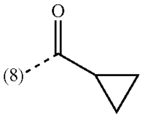 | |
| B-25 | E25* | 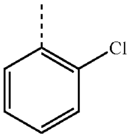 | 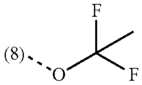 | |
| B-26 | E26* | 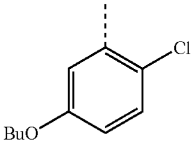 | 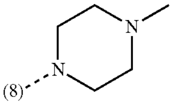 | |
| B-27 | E27* | 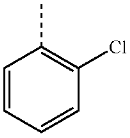 | (8)----$NH_2$ | |
| B-28 | E28* | 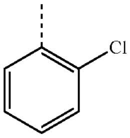 | 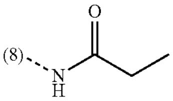 | |
| B-29 | E29* | 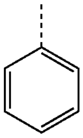 | 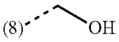 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

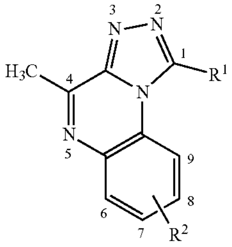

| Co. no. | Ex. no. | $R^1$ | $R^2$ | Salt form |
|---|---|---|---|---|
| B-30 | E30* | 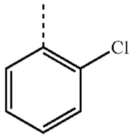 | 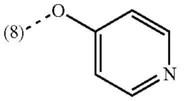 | |
| B-31 | E9 | 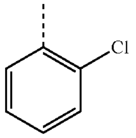 | 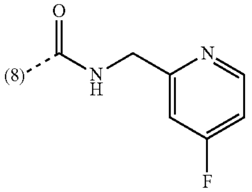 | |
| B-32 | E9 | 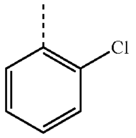 | 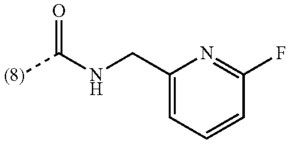 | |
| B-33 | E9 | 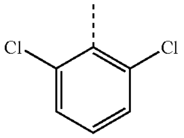 | 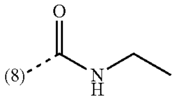 | |
| B-34 | E9 | 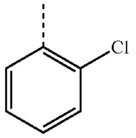 | 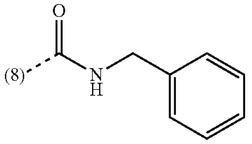 | |
| B-35 | E9 | 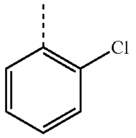 | 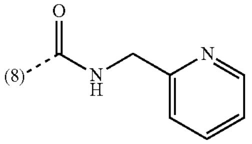 | |
| B-36 | E9 | 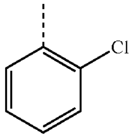 | 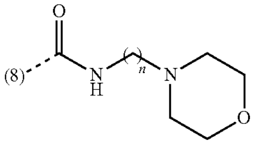 n = 2 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

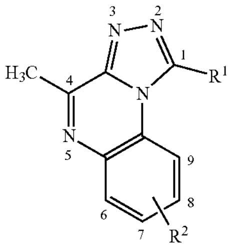

| Co. no. | Ex. no. | $R^1$ | $R^2$ | Salt form |
|---|---|---|---|---|
| B-37 | E9 | 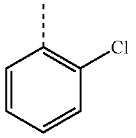 | 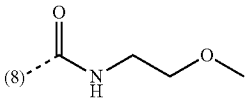 | |
| B-38 | E9 | 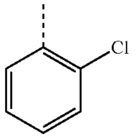 | 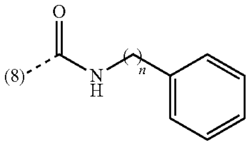 n = 2 | |
| B-39 | E11 | 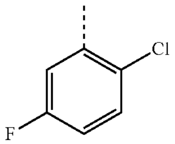 | 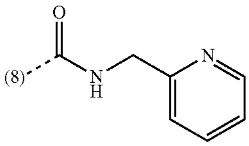 | |
| B-40 | E9 | 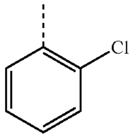 | 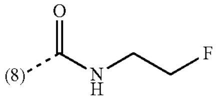 | |
| B-41 | E9 | 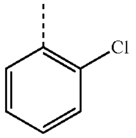 | 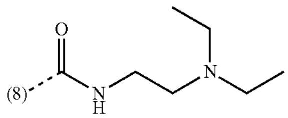 | |
| B-42 | E9 | 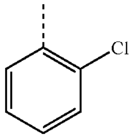 | 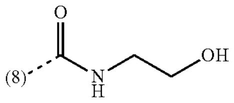 | |
| B-43 | E11 | 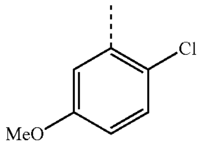 | 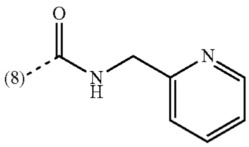 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

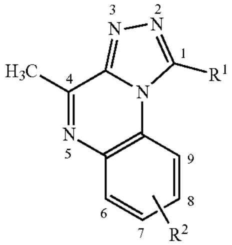

| Co. no. | Ex. no. | $R^1$ | $R^2$ | Salt form |
|---|---|---|---|---|
| B-44 | E11 | 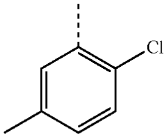 | 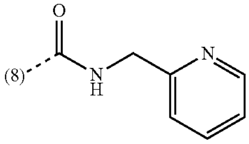 | |
| B-45 | E9 | 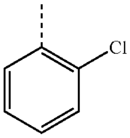 | 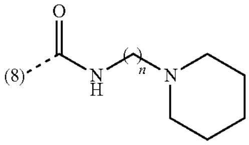 n = 2 | |
| B-46 | E9 | 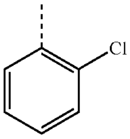 | 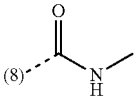 | |
| B-47 | E9 | 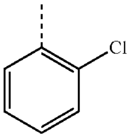 | 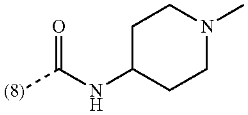 | |
| B-48 | E9 | 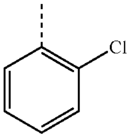 | 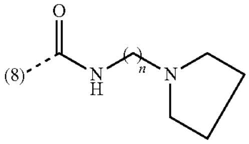 n = 2 | |
| B-49 | E9 | 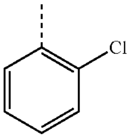 | 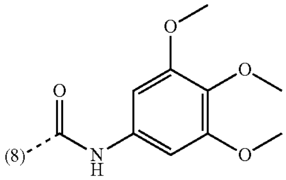 | |
| B-50 | E20 | 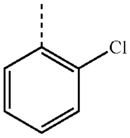 | 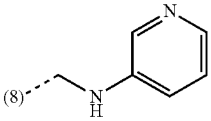 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

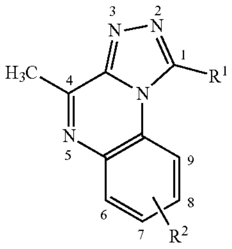

| Co. no. | Ex. no. | $R^1$ | $R^2$ | Salt form |
|---|---|---|---|---|
| B-51 | E9 | 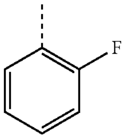 | 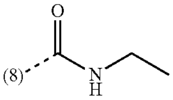 | |
| B-52 | E9 | 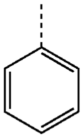 | 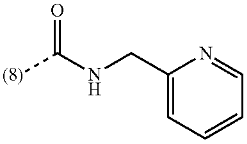 | |
| B-53 | E9 | 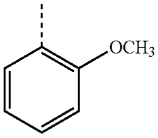 | 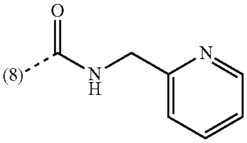 | |
| B-54 | E9 | 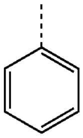 | 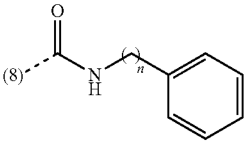 n = 2 | |
| B-55 | E19 | 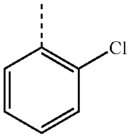 | 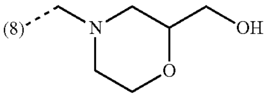 | |
| B-56 | E9 | 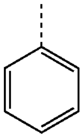 | 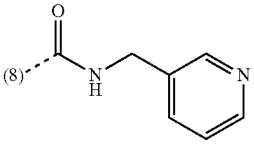 | |
| B-57 | E19 | 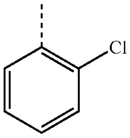 | 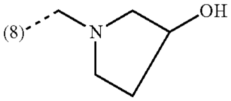 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

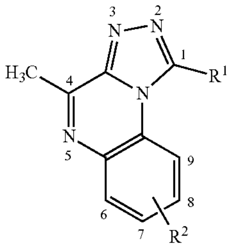

| Co. no. | Ex. no. | $R^1$ | $R^2$ | Salt form |
|---|---|---|---|---|
| B-58 | E17b | 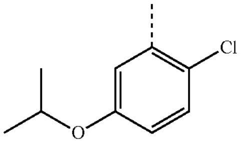 | 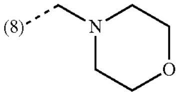 | .HCl |
| B-59 | E19 | 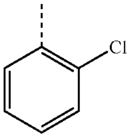 | 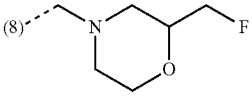 | |
| B-60 | E16 | 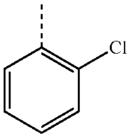 | 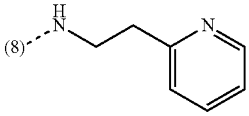 | |
| B-61 | E19 | 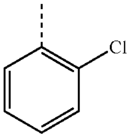 | 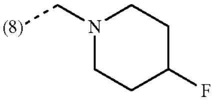 | |
| B-62 | E19 | 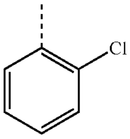 | 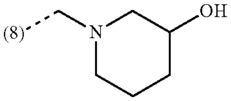 | |
| B-63 | E19 | 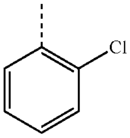 | 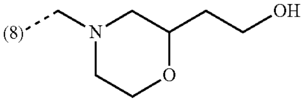 | |
| B-64 | E22 | 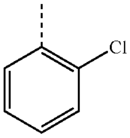 | 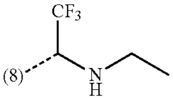 | |
| B-65 | E9 | 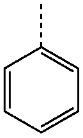 | 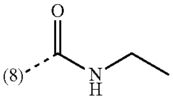 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

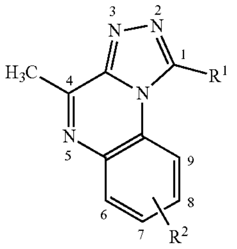

| Co. no. | Ex. no. | $R^1$ | $R^2$ | Salt form |
|---|---|---|---|---|
| B-66 | E9 | 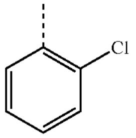 | 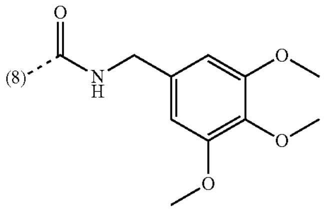 | |
| B-67 | E16 | 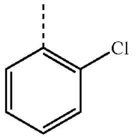 | 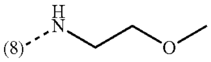 | |
| B-68 | E9 | 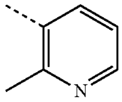 | 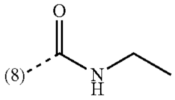 | |
| B-69 | E6 | 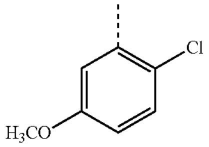 | (8)----Br | |
| B-70 | E17b | 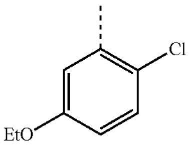 | 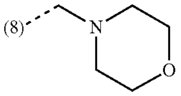 | .HCl |
| B-71 | E16 | 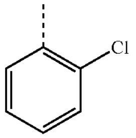 | 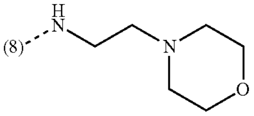 | |
| B-72 | E17b | 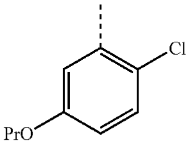 | 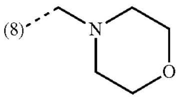 | .HCl |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

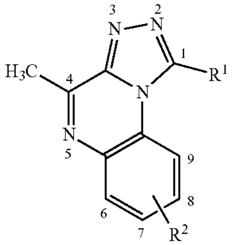

| Co. no. | Ex. no. | $R^1$ | $R^2$ | Salt form |
|---|---|---|---|---|
| B-73 | E19 | 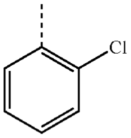 | 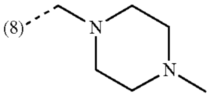 | |
| B-74 | E11 | 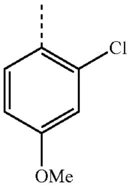 | 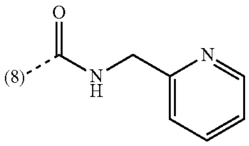 | |
| B-75 | E17b | 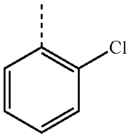 | 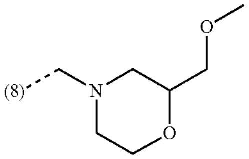 | .1.5HCl |
| B-76 | E20 | 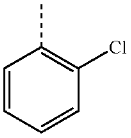 | 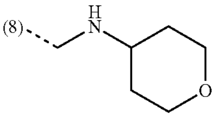 | |
| B-77 | E9 | 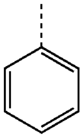 | 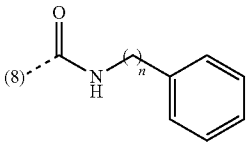 n = 3 | |
| B-78 | E9 | 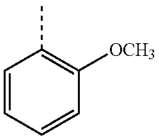 | 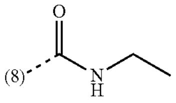 | |
| B-79 | E17b | 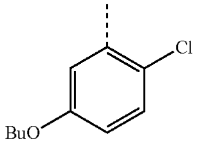 | 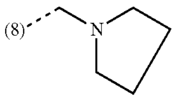 | .HCl |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

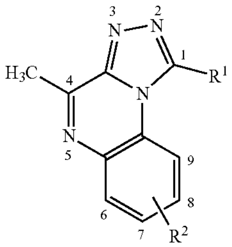

| Co. no. | Ex. no. | $R^1$ | $R^2$ | Salt form |
|---|---|---|---|---|
| B-80 | E9 | 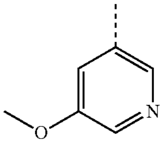 | 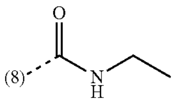 | |
| B-81 | E19 | 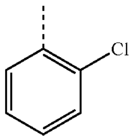 | 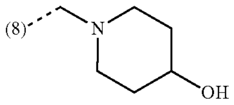 | |
| B-82 | E19 | 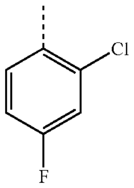 | 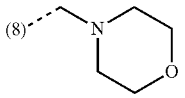 | |
| B-83 | E9 | 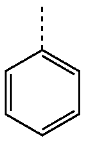 | 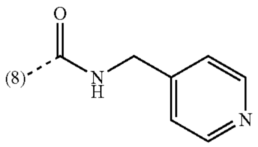 | |
| B-84 | E17a | 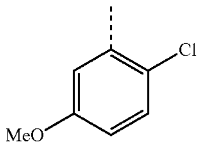 | 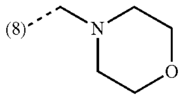 | |
| B-85 | E6 | 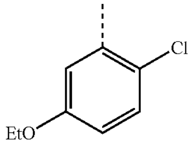 | (8)----Br | |
| B-86 | E19 | 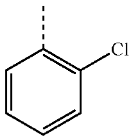 | 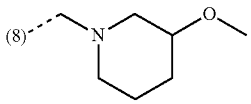 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

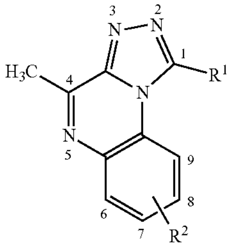

| Co. no. | Ex. no. | $R^1$ | $R^2$ | Salt form |
| --- | --- | --- | --- | --- |
| B-87 | E16 | 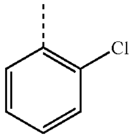 | 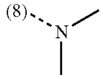 | |
| B-88 | E19 | 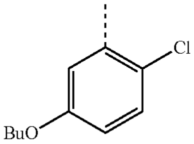 | 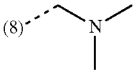 | |
| B-89 | E19 | 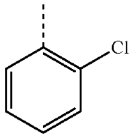 | 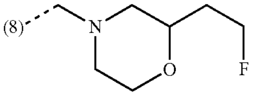 | |
| B-90 | E20 | 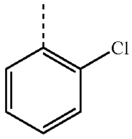 | 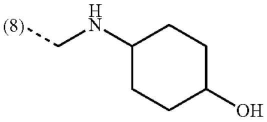 trans | |
| B-91 | E19 | 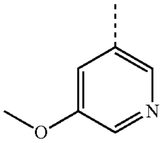 | 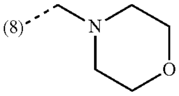 | |
| B-92 | E6 | 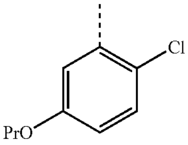 | (8)----Br | |
| B-93 | E19 | 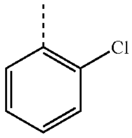 | 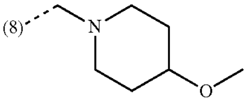 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

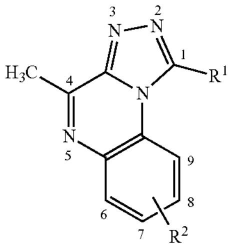

| Co. no. | Ex. no. | $R^1$ | $R^2$ | Salt form |
|---|---|---|---|---|
| B-94 | E19 | 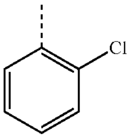 | 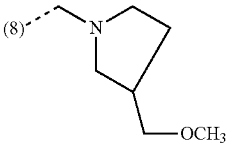 | |
| B-95 | E5 | 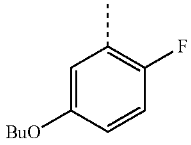 | (8)----Br | |
| B-96 | E3 | 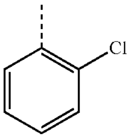 | H | |
| B-97 | E19 | 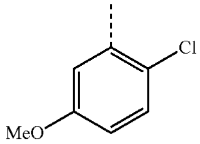 | 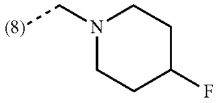 | |
| B-98 | E12 | 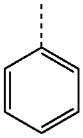 | 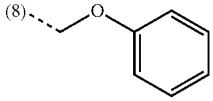 | |
| B-99 | E20 | 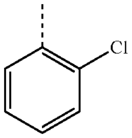 | 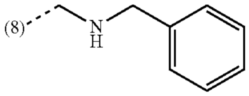 | |
| B-100 | E6 | 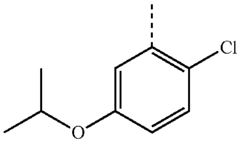 | (8)----Br | |
| B-101 | E20 | 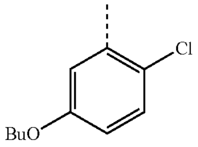 | 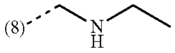 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

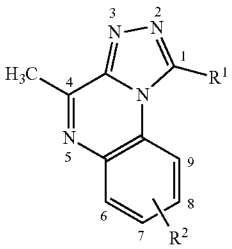

| Co. no. | Ex. no. | $R^1$ | $R^2$ | Salt form |
|---|---|---|---|---|
| B-102 | E26 | 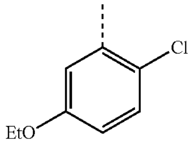 | 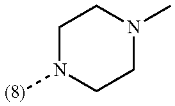 | |
| B-103 | E20 | 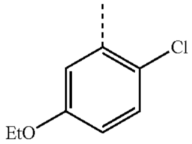 | 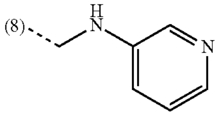 | .HCl |
| B-104 | E9 | 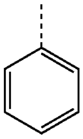 | 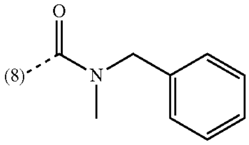 | |
| B-105 | E19 | 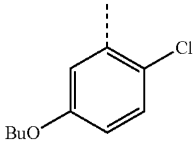 | 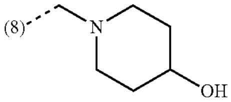 | |
| B-106 | E19 | 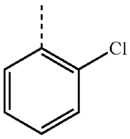 | 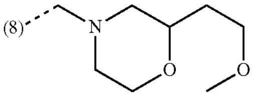 | |
| B-107 | E19 | 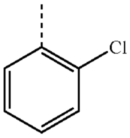 | 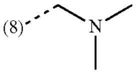 | |
| B-108 | E11 | 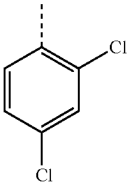 | 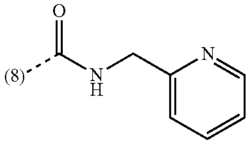 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

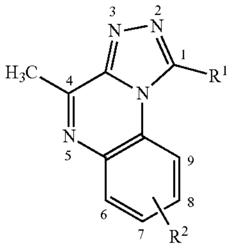

| Co. no. | Ex. no. | $R^1$ | $R^2$ | Salt form |
|---|---|---|---|---|
| B-109 | E9 | 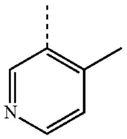 | 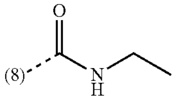 | |
| B-110 | E19 | 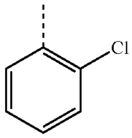 | 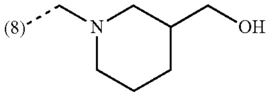 | |
| B-111 | E20 | 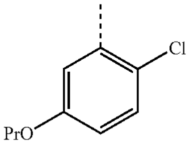 | 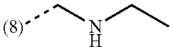 | |
| B-112 | E17b | 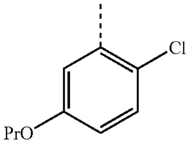 | 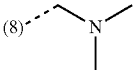 | .0.4HCl |
| B-113 | E15 | 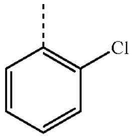 | 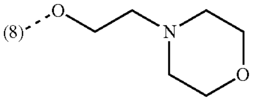 | |
| B-114 | E19 | 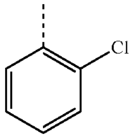 | 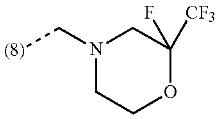 | |
| B-115 | E26 | 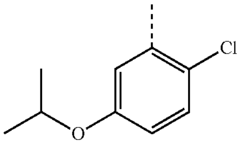 | 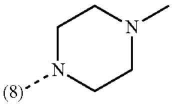 | |
| B-116 | E15 | 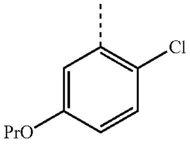 | 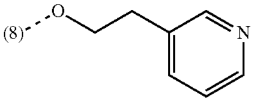 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

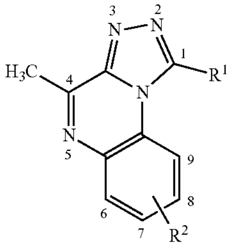

| Co. no. | Ex. no. | $R^1$ | $R^2$ | Salt form |
|---|---|---|---|---|
| B-117 | E26 | 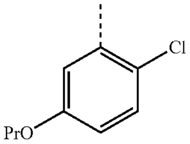 | 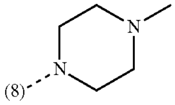 | |
| B-118 | E19 | 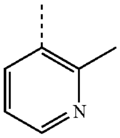 | 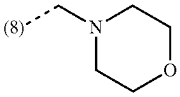 | |
| B-119 | E17b | 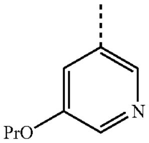 | 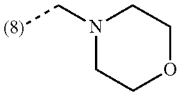 | .HCl |
| B-120 | E5 | 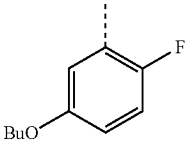 | (8)----CN | |
| B-121 | E15 | 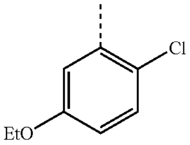 | 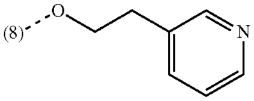 | |
| B-122 | E8 | 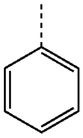 | 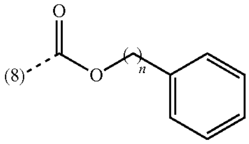 n = 2 | |
| B-123 | E9 | 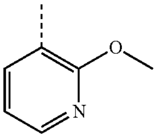 | 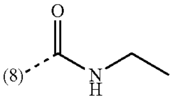 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

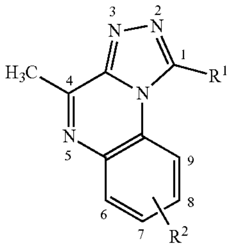

| Co. no. | Ex. no. | $R^1$ | $R^2$ | Salt form |
|---|---|---|---|---|
| B-124 | E7 | 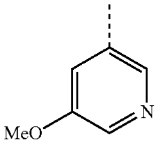 | (8)----Br | |
| B-125 | E7 | 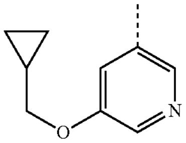 | (8)----Br | |
| B-126 | E20 | 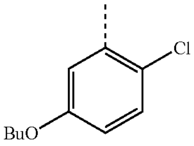 | 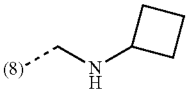 | |
| B-127 | E9 | 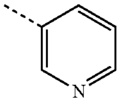 | 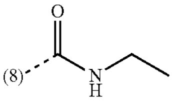 | |
| B-128 | E19 | 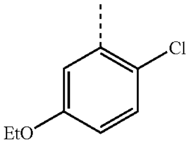 | 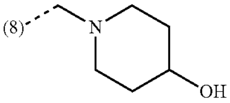 | |
| B-129 | E19 | 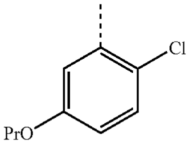 | 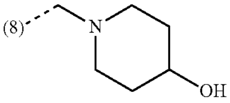 | |
| B-130 | E15 | 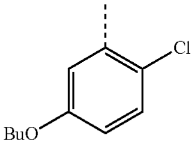 | 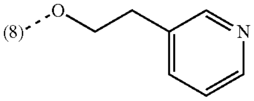 | |
| B-131 | E3 | 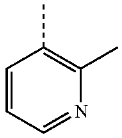 | (8)----Br | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

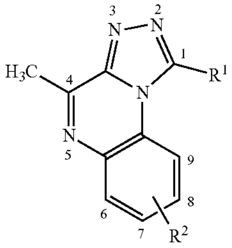

| Co. no. | Ex. no. | $R^1$ | $R^2$ | Salt form |
|---|---|---|---|---|
| B-132 | E19 | 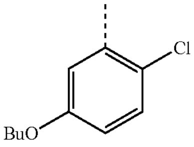 | 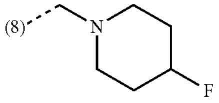 | |
| B-133 | E20 | 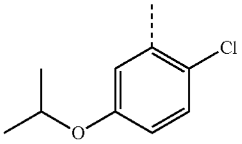 | 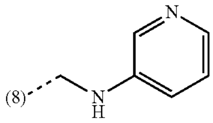 | .xHCl |
| B-134 | E17b | 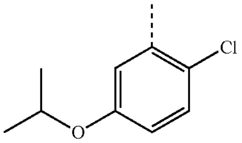 | 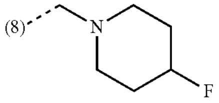 | .0.5HCl |
| B-135 | E19 | 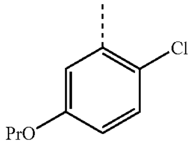 | 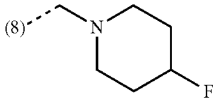 | |
| B-136 | E19 | 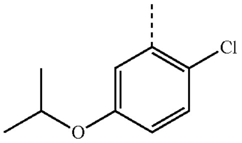 | 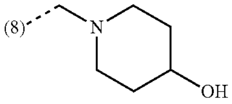 | |
| B-137 | E19 | 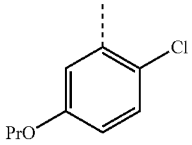 | 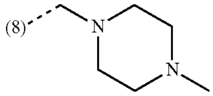 | |
| B-138 | E20 | 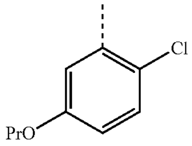 | 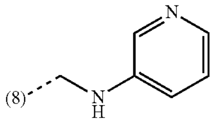 | .xHCl |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

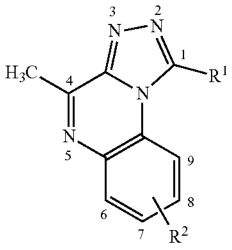

| Co. no. | Ex. no. | $R^1$ | $R^2$ | Salt form |
|---|---|---|---|---|
| B-139 | E15 | 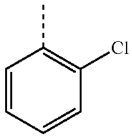 | 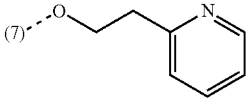 | |
| B-140 | E17b | 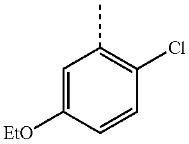 | 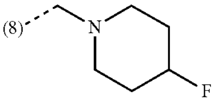 | .0.4HCl |
| B-141 | E19 | 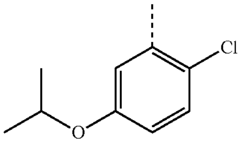 | 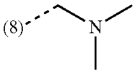 | |
| B-142 | E19 | 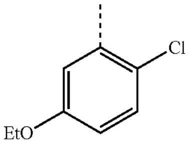 | 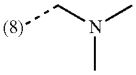 | |
| B-143 | E9 | 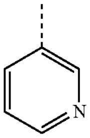 | 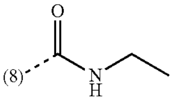 | |
| B-144 | E24 | 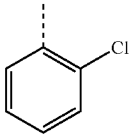 | 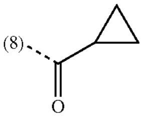 | |
| B-145 | E17b | 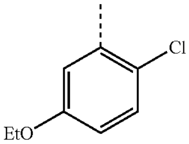 | 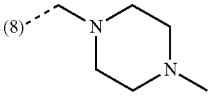 | .2HCl |
| B-146 | E15 | 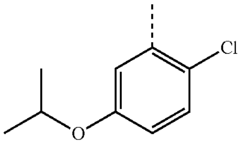 | 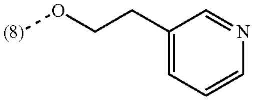 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

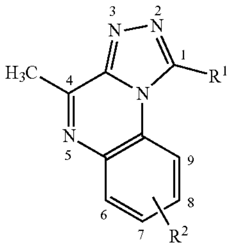

| Co. no. | Ex. no. | $R^1$ | $R^2$ | Salt form |
|---|---|---|---|---|
| B-147 | E16 | 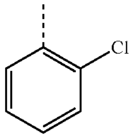 | 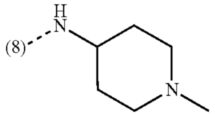 | |
| B-148 | E20 | 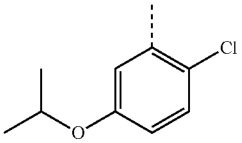 | 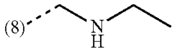 | .HCl |
| B-149 | E20 | 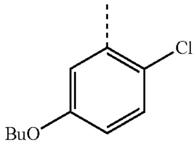 | 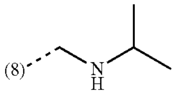 | |
| B-150 | E20 | 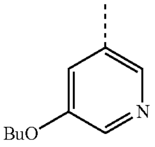 | 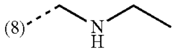 | .1.4HCl |
| B-151 | E20 | 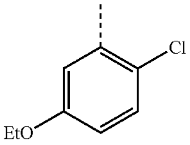 | 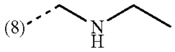 | |
| B-151a | E20 | 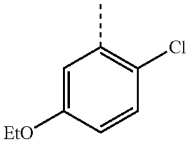 | 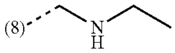 | .HCl |
| B-152 | E20 | 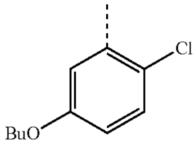 | 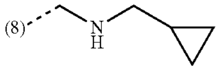 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

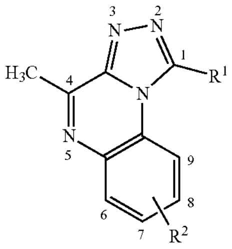

| Co. no. | Ex. no. | $R^1$ | $R^2$ | Salt form |
|---|---|---|---|---|
| B-153 | E20 | 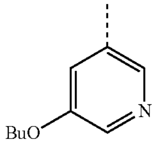 | 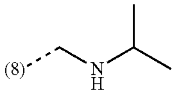 | .0.6HCl |
| B-154 | E7 | 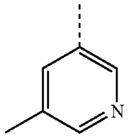 | (8)----Br | |
| B-155 | E20 | 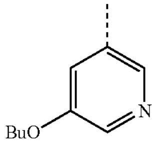 | 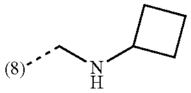 | .1.5HCl |
| B-156 | E20 | 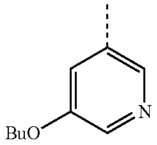 | 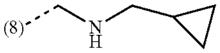 | .1.2HCl |
| B-157 | E19 | 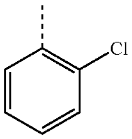 | 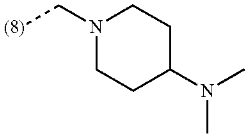 | |
| B-158 | E8 | 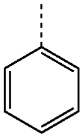 | 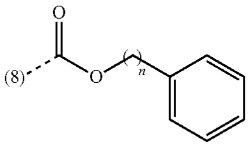 n = 3 | |
| B-159 | E5 | 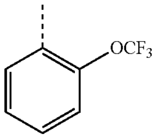 | (8)----Br | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

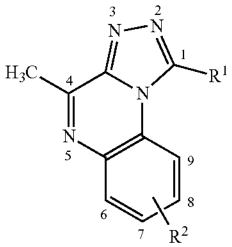

| Co. no. | Ex. no. | $R^1$ | $R^2$ | Salt form |
|---|---|---|---|---|
| B-160 | E20 | 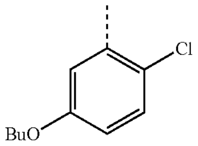 | 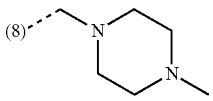 | .1.4HCl |
| B-161 | E15 | 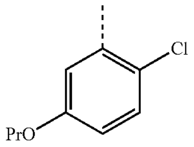 | 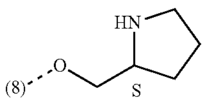 | .HCl |
| B-162 | E7 | 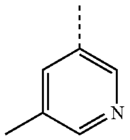 | (8)----$CF_3$ | |
| B-163 | E4 | 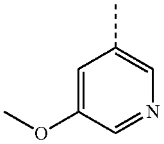 | (8)----$CF_3$ | |
| B-164 | E5 | 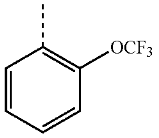 | (8)----OMe | |
| B-165 | E4 | 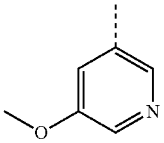 | (8)----$OCF_3$ | |
| B-166 | E3 | 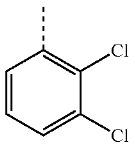 | (8)----Br | |
| B-167 | E4 | 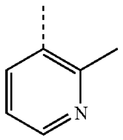 | (8)----$CF_3$ | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

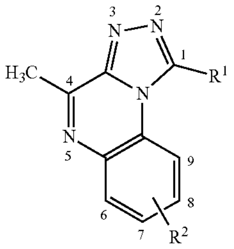

| Co. no. | Ex. no. | $R^1$ | $R^2$ | Salt form |
|---|---|---|---|---|
| B-168 | E4 | 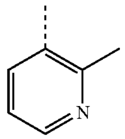 | (8)----$OCF_3$ | |
| B-169 | E9 | 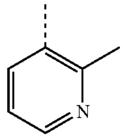 | 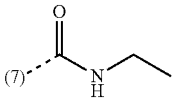 | |
| B-170 | E17b | 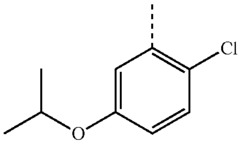 | 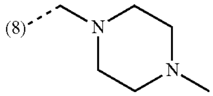 | .1.5HCl |
| B-171 | E7 | 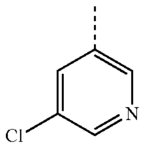 | (8)----Br | |
| B-172 | E9 | 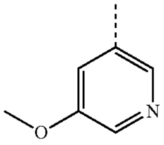 | 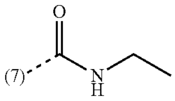 | |
| B-173 | E7 | 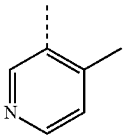 | (8)----$OCH_3$ | |
| B-174 | E1 | 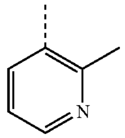 | H | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

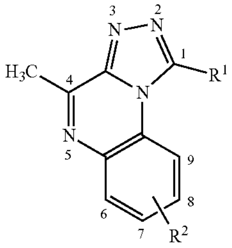

| Co. no. | Ex. no. | $R^1$ | $R^2$ | Salt form |
|---|---|---|---|---|
| B-175 | E3 | 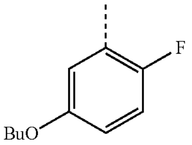 | (7)----Br | |
| B-176 | E5 | 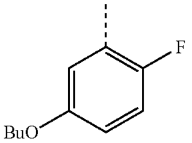 | (7)----CN | |
| B-177 | E5 | 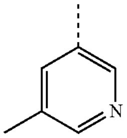 | H | |
| B-178 | E20 | 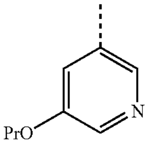 | 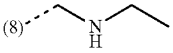 | .HCl |
| B-179 | E9 | 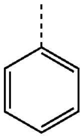 | 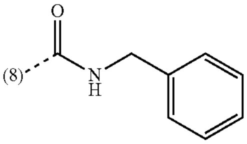 | |
| B-180 | E9 | 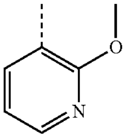 | 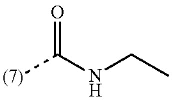 | |
| B-181 | E9 | 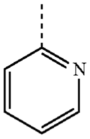 | 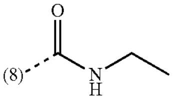 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

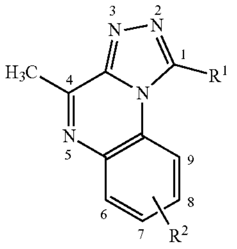

| Co. no. | Ex. no. | $R^1$ | $R^2$ | Salt form |
|---|---|---|---|---|
| B-182 | E9 | 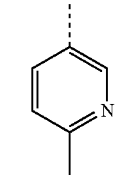 | 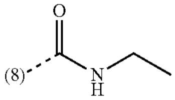 | |
| B-183 | E7 | 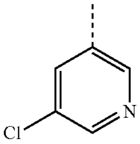 | H | |
| B-184 | I13* | 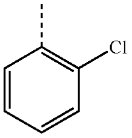 | 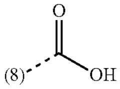 | |
| B-185 | I14* | 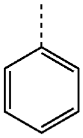 | 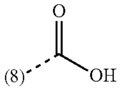 | |
| B-186a | I20* | 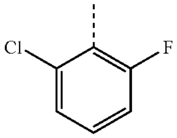 | (8)----Br | |
| B-186b | I20* | 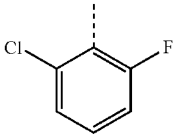 | (7)----Br | |
| B-187 | I21* | 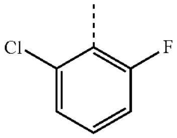 | 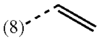 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

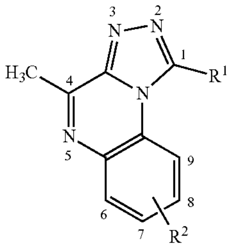

| Co. no. | Ex. no. | $R^1$ | $R^2$ | Salt form |
|---|---|---|---|---|
| B-188 | I24* | 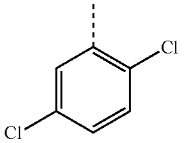 | (8)----Br | |
| B-189 | I25* | 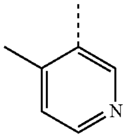 | (8)----Br | |
| B-190 | I26* | 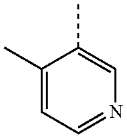 | 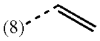 | |
| B-191 | I29* | 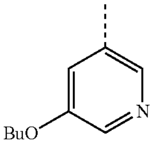 | 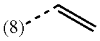 | |
| B-192 | E20 | 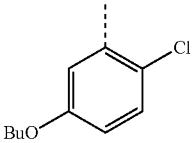 | 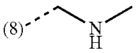 | 2HCl |
| B-193 | E17b | 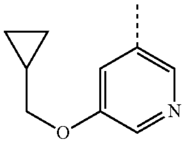 | 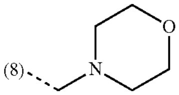 | HCl |
| B-194 | E17a | 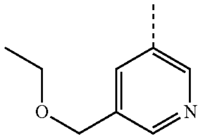 | 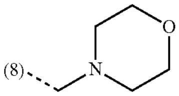 | HCl |
| B-195 | E19 | 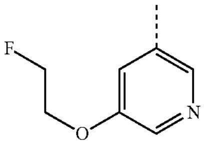 | 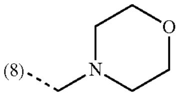 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

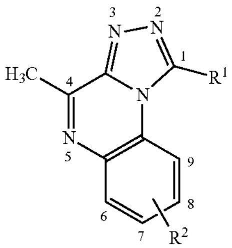

| Co. no. | Ex. no. | $R^1$ | $R^2$ | Salt form |
|---|---|---|---|---|
| B-196 | E19 | 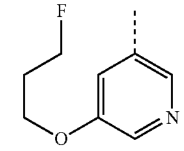 | 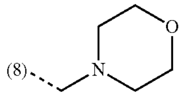 | |
| B-197 | E17b | 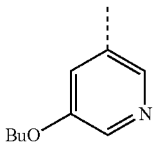 | 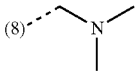 | 2HCl |
| B-198 | E17a | 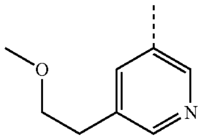 | 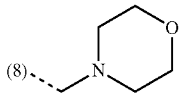 | 1.5HCl |
| B-199 | E17b | 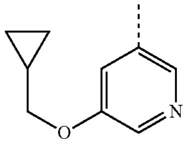 | 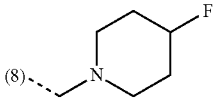 | 1.5HCl |
| B-200 | E20 | 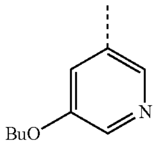 | 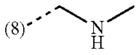 | 1.7HCl |
| B-201 | E17b | 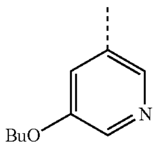 | 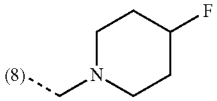 | 1.6HCl |
| B-202 | E19 | 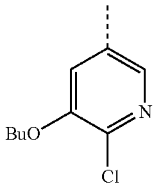 | 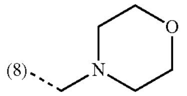 | |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

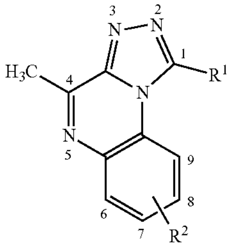

| Co. no. | Ex. no. | $R^1$ | $R^2$ | Salt form |
|---|---|---|---|---|
| B-203 | E19 | 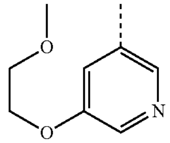 | 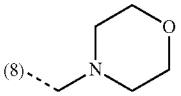 | |
| B-204 | E17a | 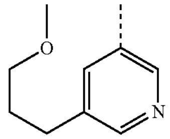 | 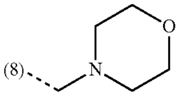 | HCl |
| B-205 | E17b | 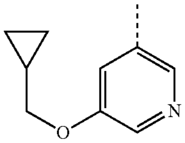 | 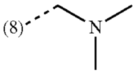 | 1.5HCl |
| B-206 | E17b | 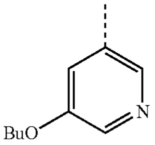 | 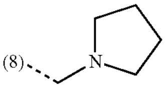 | 1.6HCl |
| B-207 | E20 | 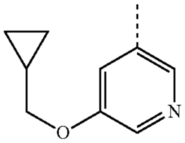 | 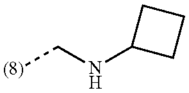 | 1.8HCl |
| B-208 | E17b | 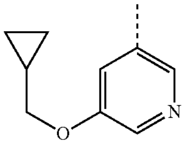 | 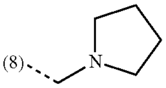 | 1.7HCl |
| B-209 | E20 | 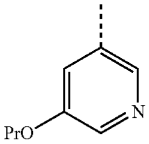 | 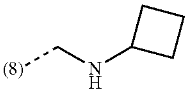 | HCl |

TABLE 1-continued

The following compounds were prepared following the methods exemplified in the Experimental Part (Ex. No.). Compounds exemplified and described in the experimental part are marked with an asterisk *. Bu means 1-butyl. Compound 151 was isolated as the free base and also converted to a hydrochloride salt (compound 151a).

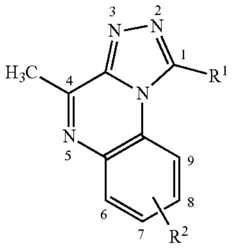

| Co. no. | Ex. no. | $R^1$ | $R^2$ | Salt form |
|---|---|---|---|---|
| B-210 | E20 | 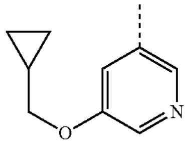 | 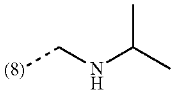 | 1.7HCl |
| B-211 | E20 | 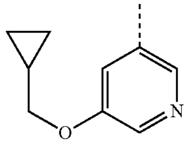 | 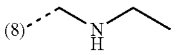 | HCl |
| B-212 | E17b | 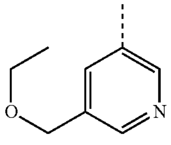 | 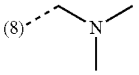 | HCl |
| B-213 | E20 | 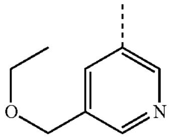 | 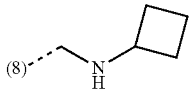 | 2.1HCl |

Analytical Part

LCMS

For LC-MS characterization of the compounds of the present invention, the following methods were used.

General Procedure A

The HPLC measurement was performed using an HP 1100 (Agilent Technologies) system comprising a pump (quaternary or binary) with degasser, an autosampler, a column oven, a diode-array detector (DAD) and a column as specified in the respective methods below. Flow from the column was split to the MS spectrometer. The MS detector was configured with either an electrospray ionization source or an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

General Procedure B

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified in the respective methods below. Column flow was used without split to the MS detector. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

General Procedure C

The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

General Procedure D

The HPLC measurement was performed using an Agilent 1100 module comprising a pump, a diode-array detector (DAD) (Agilent 1200) (wavelength used 254 nm), a column heater and a column as specified in the respective methods below. Flow from the column was split to a Agilent MSD Serie G1956A. MS detector was configured with API-ES (atmospheric pressure electrospray ionization). Mass spectra were acquired by scanning from 105 to 1400. The capillary needle voltage was 3000 V for positive ionization mode. Fragmentation voltage was 70 V. Drying gas temperature was maintained at 350° C. at a flow of 12 l/min.

Method 1

In addition to the general procedure A: Reversed phase HPLC was carried out on a Sunfire-C18 column (2.5 μm, 2.1×30 mm) from Waters, with a flow rate of 1.0 ml/min, at 60° C. The gradient conditions used are: 95% A (0.5 g/l ammonium acetate solution+5% of acetonitrile), 2.5% B (acetonitrile), 2.5% C (methanol) to 50% B, 50% C in 6.5 minutes, kept till 7.0 minutes and equilibrated to initial conditions at 7.3 minutes until 9.0 minutes. Injection volume 2 μl. High-resolution mass spectra (Time of Flight, TOF detector) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

Method 2

In addition to the general procedure B: Reversed phase UPLC was carried out on a BEH-C18 column (1.7 μm, 2.1×50 mm) from Waters, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 4.4 minutes, to 5% A, 95% B in 5.6 minutes, kept till 5.8 minutes and equilibrated to initial conditions at 6.0 minutes until 7.0 minutes. Injection volume 0.5 μl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

Method 3

In addition to the general procedure B: Reversed phase UPLC was carried out on a BEH-C18 column (1.7 μm, 2.1×50 mm) from Waters, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 2.8 minutes, to 5% A, 95% B in 3.6 minutes, kept till 3.8 minutes and equilibrated to initial conditions at 4.0 minutes until 5.0 minutes. Injection volume 0.5 μl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

Method 4

In addition to the general procedure B: Reversed phase UPLC was carried out on a BEH-C18 column (1.7 μm, 2.1×50 mm) from Waters, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 3.8 minutes, to 5% A, 95% B in 4.6 minutes, kept till 5.0 minutes. Injection volume 2.0 μl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

Method 5

In addition to general procedure C: reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

Method 6

In addition to general procedure C: reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (25 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used. Cone voltage was 30 V for positive ionization mode and 30 V for negative ionization mode.

Method 7

In addition to the general procedure D: Reversed phase HPLC was carried out on a YMC pack ODS-AQ C18 column (3 μm, 50 mm×4.6 mm) with a flow rate of 2.6 mL/min, at 35° C. A gradient elution was performed from 95% ($H_2O$+0.1% HCOOH)/5% $CH_3CN$ to 5% ($H_2O$+0.1% HCOOH)/95% $CH_3CN$ in 4.8 min and held for 1.0 min; then to 95% ($H_2O$+0.1% HCOOH)/5% $CH_3CN$ in 0.2 min. The injection volume was 2 μL. Acquisition ranges were set to 190-400 nm for the UV-PDA detector and 100-1400 m/z for the MS detector.

Method 8

In addition to the general procedure A: Reversed phase HPLC was carried out on an Eclipse Plus-C18 column (3.5 μm, 2.1×30 mm) from Agilent, with a flow rate of 1.0 ml/min, at 60° C. without split to the MS detector. The gradient conditions used are: 95% A (0.5 g/l ammonium acetate solution+5% acetonitrile), 5% B (mixture of acetonitrile/methanol, 1/1), to 100% B in 5.0 minutes, kept till 5.15 minutes and equilibrated to initial conditions at 5.30 minutes until 7.0 minutes. Injection volume 2 μl. Low-resolution mass spectra (single quadrupole, SQD detector) were acquired by scanning from 100 to 1000 in 0.1 second using an inter-channel delay of 0.08 second. The capillary needle voltage was 3 kV. The cone voltage was 20 V for positive ionization mode and 30 V for negative ionization mode.

Method 9

Same gradient as method 4; column used: RRHD Eclipse Plus-C18 (1.8 μm, 2.1×50 mm) from Agilent.

Method 10

In addition to the general procedure C: Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute, 100% B for 1 minute and reequilibrate with 100% A for 1.5 minutes. An injection volume of 10 μl was used.

Cone voltage was 10 V for positive ionization mode and 20 V for negative ionization mode.

Method 11

In addition to the general procedure A: Reversed phase HPLC was carried out on an Eclipse Plus-C18 column (3.5 μm, 2.1×30 mm) from Agilent, with a flow rate of 1.0 ml/min, at 60° C. without split to the MS detector. The gradient conditions used are: 95% A (0.5 g/l ammonium acetate solution+5% acetonitrile), 5% B (mixture of acetonitrile/methanol, 1/1), kept 0.2 minutes, to 100% B in 3.0 minutes, kept till 3.15 minutes and equilibrated to initial conditions at 3.30 minutes until 5.0 minutes. Injection volume 2 μl. Low-resolution mass spectra (single quadrupole, SQD detector) were acquired by scanning from 100 to 1000 in 0.1 second using an inter-channel delay of 0.08 second. The capillary needle voltage was 3 kV. The cone voltage was 20 V and 50 V for positive ionization mode and 30 V for negative ionization mode.

Method 12

In addition to the general procedure B: Reversed phase UPLC was carried out on a RRHD Eclipse Plus-C18 (1.8 μm, 2.1×50 mm) from Agilent, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 1.2 minutes, to 5% A, 95% B in 1.8 minutes, kept till 2.0 minutes. Injection volume 2.0 μl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

Method 13

In addition to the general procedure C: Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (10 mM $NH_4AcO$ in $H_2O/CH_3CN$ 95/5; mobile phase B: $CH_3CN$) were used to run a gradient condition from 95% A and 5% B to 5% A and 95% B in 1.3 minutes and hold for 0.7 minutes. An injection volume of 0.75 ml was used. Cone voltage was 10 V for positive ionization mode and 20 V for negative ionization mode.

Method 14

In addition to the general procedure D: Reversed phase HPLC was carried out on a SB-C18 1pk column (4.6×30 mm, 1.8 μm) with a flow rate of 4.0 ml/min, at 65° C. A gradient elution was performed from 88% $H_2O$ and 12% $CH_3CN$ to 88% $CH_3CN$/12% $H_2O$ in 1.10 minutes and held for 0.50 minutes, then to 88% $H_2O$/12% $CH_3CN$ in 0.2 min and held for 0.40 minutes. The injection volume was 1 μL. MS acquisition range and UV detector were set to 150-1200 m/z and 254 nm respectively

GCMS:

General Procedure for Agilent GC/MSD Instrument

The GC measurement was performed using a 6890 Series Gas Chromatograph (Agilent Technologies) system comprising a 7683 Series injector and autosampler, a column oven and a column as specified in the respective methods below, coupled to a 5973N MSD Mass Selective Detector (single quadrupole, Agilent Technologies). The MS detector was configured with an electronic impact ionization source/chemical ionization source (EI/CI). EI low-resolution mass spectra were acquired by scanning from 50 to 550 at a rate of 14.29 scans/s. The source temperature was maintained at 230° C. Helium was used as the nebulizer gas. Data acquisition was performed with Chemstation-Open Action software.

Method 1

In addition to the general procedure: GC was carried out on a J&W HP-5MS column (20 m×0.18 mm, 0.18 μm) from Agilent Technologies, with a flow rate of 0.7 ml/min. The temperature gradient applied was: initial temperature 50° C., hold for 2.0 min, then a 50° C./min ramp applied for 5.0 min until 300° C. and hold for 3.0 min in a 10 min run. Front inlet temperature was 250° C. Split injection mode was used, 0.2 μl injection volume, with a 50/1 ratio into the GC/MS system.

Melting Points

Values are either peak values or melt ranges, and are obtained with experimental uncertainties that are commonly associated with this analytical method.

Mettler FP62 Apparatus

For a number of compounds, melting points were determined in open capillary tubes on a Mettler FP62 apparatus. Melting points were measured with a temperature gradient of 1, 3, 5 or 10° C./minute. Maximum temperature was 300° C. The melting point was read from a digital display.

DSC823e Mettler-Toledo Apparatus

For a number of compounds, melting points were determined with a DSC823e Mettler-Toledo (indicated with DSC in table 2). Melting points were measured with a temperature gradient of 30° C./minute. Maximum temperature was 400° C.

Nuclear Magnetic Resonance (NMR)

$^1$H NMR spectra were recorded either on a Bruker Avance III, on a Bruker DPX-400 or on a Bruker AV-500 spectrometer with standard pulse sequences, operating at 300 MHz, 400 MHz and 500 MHz respectively. Chemical shifts (δ) are reported in parts per million (ppm) downfield from tetramethylsilane (TMS), which was used as internal standard.

TABLE 2

Analytical data - $R_t$ means retention time (in minutes), $[M + H]^+$ means the protonated mass of the compound, method refers to the method used for (LC)MS, dec means decomposition.

| Co. no. | mp (° C.) | [MH+] | Rt | LCMS method |
|---|---|---|---|---|
| B-1a | 219.5 | 367 | 2.78 | 2 |
| B-1b | 222.8 | 367 | 2.91 | 2 |
| B-2a | 191.5 | 333 | 1.84 | 3 |
| B-2b | 171.4 | 333 | 1.93 | 3 |
| B-3a | >300 (dec) | 373 | 2.06 | 3 |
| B-3b | >300 (dec) | 373 | 2.16 | 3 |
| B-4a | 187.8 (DSC) | 379 | 2.75 | 4 |
| B-4b | n.d. | 379 | 3.81 | 8 |
| B-5 | 187.6 | 325 | 2.54 | 7 |
| B-6a | 154.7 | 445 | 3.68 | 4 |
| B-6b | 152.1 (DSC) | 445 | 3.81 | 4 |
| B-7 | 170.2 | 412 | 2.95 | 9 |
| B-8 | 188.5 | 395 | 3.25 | 2 |
| B-9 | 264.3 | 394 | 2.26 | 2 |
| B-10 | >300 (dec) | 366 | 2.86 | 1 |
| B-11 | 274.1 (DSC) | 463 | 0.82 | 6 |

TABLE 2-continued

Analytical data - $R_t$ means retention time (in minutes), $[M + H]^+$ means the protonated mass of the compound, method refers to the method used for (LC)MS, dec means decomposition.

| Co. no. | mp (° C.) | [MH+] | Rt | LCMS method |
|---|---|---|---|---|
| B-12 | 141.9 (DSC) | 319 | 1.43 | 5 |
| B-13 | >300 | 311 | 1.13 | 3 |
| B-14 | >300 (dec) | 321 | 2.01 | 3 |
| B-15 | 159.5 | 416 | 2.22 | 4 |
| B-16 | n.d. | 393 | 1.81 | 2 |
| B-17a | 249.9 (DSC) | 433 | 0.92 | 13 |
| B-17b | 211.3 | 433 | 1.8 | 7 |
| B-18 | 221.7 (DSC) | 466 | 2.18 | 7 |
| B-19 | 160.4 | 394 | 1.89 | 4 |
| B-20 | 106.9 | 352 | 0.93 | 3 |
| B-21 | 228.4 | 393 | 1.98 | 4 |
| B-22 | n.d. | 462 | 251 | 4 |
| B-23 | 159 | 412 | 1.98 | 4 |
| B-24 | n.d. | 344 | 2.09 | 7 |
| B-25 | 170.3 (DSC) | 375 | 2.53 | 4 |
| B-26 | 174.1 | 465 | 2.99 | 9 |
| B-27 | >300 | 310 | 1.06 | 3 |
| B-28 | n.d. | 366 | 1.35 | 3 |
| B-29 | 240.6 (DSC) | 291 | 1.14 | 2 |
| B-30 | n.d. | 438 | 1.66 | 3 |
| B-31 | n.d. | 447 | 1.92 | 2 |
| B-32 | >300 (dec) | 447 | 1.92 | 2 |
| B-33 | 291.8 (DSC) | 400 | 1.82 | 2 |
| B-34 | >300 (dec) | 428 | 3.75 | 1 |
| B-35 | 255.1 | 429 | 1.78 | 2 |
| B-36 | >300 (dec) | 451 | 1.5 | 2 |
| B-37 | >300 (dec) | 396 | 1.58 | 2 |
| B-38 | >300 | 442 | 2.68 | 2 |
| B-39 | 268.3 (DSC) | 447 | 0.77 | 6 |
| B-40 | 232.1 | 384 | 1.54 | 2 |
| B-41 | 201.4 | 437 | 1.23 | 2 |
| B-42 | 259.1 | 382 | 1.12 | 2 |
| B-43 | 240.5 (DSC) | 459 | 0.77 | 6 |
| B-44 | 250 (DSC) | 443 | 1.04 | 10 |
| B-45 | 184.5 | 449 | 1.35 | 2 |
| B-46 | 284.9 | 352 | 1.32 | 2 |
| B-47 | >300 (dec) | 435 | 1.13 | 2 |
| B-48 | 215.1 | 435 | 1.11 | 2 |
| B-49 | 150.6 | 504 | 2.46 | 2 |
| B-50 | n.d. | 401 | 1.68 | 4 |
| B-51 | >300 (dec) | 350 | 1.13 | 3 |
| B-52 | 248.3 | 351 | 1.52 | 2 |
| B-53 | 268.9 | 425 | 1.65 | 2 |
| B-54 | 243.6 | 408 | 2.49 | 2 |
| B-55 | 141.5 | 424 | 1.51 | 4 |
| B-56 | >300 (dec) | 395 | 1.37 | 2 |
| B-57 | 70.1 | 394 | 1.33 | 4 |
| B-58 | 247.6 | 452 | 1.88 | 7 |
| B-59 | n.d. | 426 | 2.11 | 4 |
| B-60 | >300 (dec) | 415 | 1.57 | 3 |
| B-61 | 179.5 | 410 | 2.46 | 4 |
| B-62 | >300 (dec) | 408 | 1.68 | 4 |
| B-63 | 73 | 438 | 1.66 | 4 |
| B-64 | n.d. | 420 | 257 | 4 |
| B-65 | 326.1 (DSC) | 332 | 1.41 | 2 |
| B-66 | 286.4 | 518 | 2.31 | 2 |
| B-67 | >300 (dec) | 368 | 1.44 | 3 |
| B-68 | 241.8 (DSC) | 347 | 1.62 | 7 |
| B-69 | 183.5 | 403 | 2.69 | 4 |
| B-70 | 225.8 | 438 | 1.74 | 7 |
| B-71 | 286 | 423 | 1.35 | 3 |
| B-72 | 250.5 | 452 | 1.96 | 7 |
| B-73 | 196 | 407 | 1.09 | 3 |
| B-74 | 246.9 | 459 | 0.77 | 6 |
| B-75 | 202.3 (DSC) | 438 | 1.99 | 4 |
| B-76 | 163.3 | 408 | 1.29 | 3 |
| B-77 | 267.8 | 422 | 2.77 | 2 |
| B-78 | >300 (dec) | 362 | 1.52 | 2 |
| B-79 | 134.7 | 450 | 2 | 7 |
| B-80 | 313.8 (DSC) | 363 | 1.82 | 7 |
| B-81 | 192.6 | 408 | 1.21 | 3 |
| B-82 | 176.7 | 412 | 2.02 | 4 |
| B-83 | 287.2 | 395 | 1.32 | 3 |
| B-84 | 159.5 | 424 | 1.57 | 7 |
| B-85 | 194.4 (DSC) | 417 | 3.01 | 4 |
| B-86 | n.d. | 422 | 2.34 | 4 |
| B-87 | 267.8 (DSC) | 338 | 1.78 | 3 |
| B-88 | 83.4 | 424 | 1.97 | 7 |
| B-89 | n.d. | 440 | 2.36 | 4 |
| B-90 | 185 | 422 | 0.99 | 3 |
| B-91 | 136.3 | 391 | 1.29 | 4 |
| B-92 | 238.2 | 431 | 3.36 | 4 |
| B-93 | 149.6 | 422 | 2.19 | 4 |
| B-94 | n.d. | 422 | 2.06 | 4 |
| B-95 | 154.6 (DSC) | 429 | 3.74 | 9 |
| B-96 | >300 | 295 | 1.61 | 3 |
| B-97 | 146.7 | 440 | 1.66 | 7 |
| B-98 | n.d. | 367 | 3.12 | 2 |
| B-99 | n.d. | 414 | 2.12 | 3 |
| B-100 | n.d. | 431 | 3.25 | 4 |
| B-101 | 103.8 (DSC) | 424 | 2.01 | 7 |
| B-102 | 189.1 | 437 | 1.67 | 7 |
| B-103 | 245.2 (DSC) | 445 | 1.68 | 7 |
| B-104 | 167.3 | 408 | 2.4 | 2 |
| B-105 | 202.7 (DSC) | 480 | 2.65 | 9 |
| B-106 | n.d. | 452 | 2.23 | 4 |
| B-107 | >300 (dec) | 352 | 1.35 | 3 |
| B-108 | 276.5 (DSC) | 463 | 0.83 | 6 |
| B-109 | 247.9 | 347 | 1.62 | 7 |
| B-110 | 165.4 | 422 | 1.72 | 4 |
| B-111 | 115 | 410 | 1.85 | 7 |
| B-112 | 256 (DSC) | 410 | 1.81 | 7 |
| B-113 | >300 (dec) | 424 | 1.49 | 3 |
| B-114 | 207.2 (DSC) | 480 | 3 | 4 |
| B-115 | 234.3 | 451 | 1.77 | 7 |
| B-116 | 184.7 | 474 | 2.93 | 9 |
| B-117 | 207.2 | 451 | 1.83 | 7 |
| B-118 | 141.7 | 375 | 1.17 | 4 |
| B-119 | 213.8 | 419 | 2.06 | 9 |
| B-120 | 181.3 | 376 | 3.64 | 7 |

TABLE 2-continued

Analytical data - $R_t$ means retention time (in minutes), $[M + H]^+$ means the protonated mass of the compound, method refers to the method used for (LC)MS, dec means decomposition.

| Co. no. | mp (° C.) | [MH⁺] | Rt | LCMS method |
|---|---|---|---|---|
| | (DSC) | | | |
| B-121 | 171.7 | 460 | 2.2 | 7 |
| B-122 | 155 | 409 | 3.47 | 2 |
| B-123 | 240 (DSC) | 363 | 1.9 | 7 |
| B-124 | 247.1 | 370 | 1.71 | 4 |
| B-125 | 208.5 (DSC) | 410 | 2.55 | 9 |
| B-126 | 107.3 | 450 | 2.1 | 7 |
| B-127 | n.d. | 333 | 0.84 | 2 |
| B-128 | 167.8 | 452 | 1.59 | 7 |
| B-129 | 193.4 | 466 | 1.25 | 7 |
| B-130 | 118.5 | 488 | 2.7 | 7 |
| B-131 | 258.8 | 354 | 1.57 | 4 |
| B-132 | 138.6 | 482 | 3.84 | 9 |
| B-133 | n.d. | 459 | 1.8 | 7 |
| B-134 | 97.2 | 468 | 1.94 | 7 |
| B-135 | 142.8 | 468 | 2.02 | 7 |
| B-136 | 157.5 (DSC) | 466 | 1.69 | 7 |
| B-137 | 124.9 | 465 | 2.31 | 9 |
| B-138 | n.d. | 459 | 1.87 | 7 |
| B-139 | 189.4 | 416 | 2.31 | 4 |
| B-140 | 181.2 | 454 | 1.82 | 7 |
| B-141 | 144.2 (DSC) | 410 | 1.73 | 7 |
| B-142 | 127.8 | 396 | 1.62 | 7 |
| B-143 | 309.6 (DSC) | 333 | 0.84 | 2 |
| B-144 | 185.7 (DSC) | 363 | 3.11 | 7 |
| B-145 | 265.4 | 451 | 1.77 | 7 |
| B-146 | 221.3 | 474 | 2.4 | 7 |
| B-147 | 292.8 (DSC) | 407 | 0.92 | 3 |
| B-148 | 235.3 | 410 | 1.79 | 7 |
| B-149 | 118 | 438 | 2.1 | 7 |
| B-150 | 228.8 | 391 | 1.71 | 9 |
| B-151 | 117.4 | 396 | 1.67 | 7 |
| B-151a | n.d. | 396 | 1.66 | 7 |
| B-152 | 105.5 | 450 | 2.1 | 7 |
| B-153 | 249.3 | 405 | 2.01 | 9 |
| B-154 | 249 | 355 | 2.37 | 7 |
| B-155 | 261.5 | 417 | 2.43 | 9 |
| B-156 | 254.9 | 417 | 2.17 | 9 |
| B-157 | 135.5 (DSC) | 435 | 1.27 | 4 |
| B-158 | 241.1 | 423 | 3.76 | 2 |
| B-159 | 142.9 | 423 | 2.98 | 9 |
| B-160 | 229.3 | 479 | 2.68 | 9 |
| B-161 | 170.2 | 452 | 1.94 | 9 |
| B-162 | 224.1 | 344 | 2.49 | 7 |
| B-163 | >300 (dec) | 360 | 1.93 | 4 |
| B-164 | 176.6 | 375 | 2.48 | 9 |
| B-165 | 182.8 | 376 | 1.98 | 4 |
| B-166 | n.d. | 409 | 1.34 | 5 |
| B-167 | 207.3 | 344 | 1.75 | 4 |
| B-168 | 197.6 | 360 | 2.91 | 1 |
| B-169 | 130.3 (DSC) | 347 | 1.59 | 7 |
| B-170 | 220 | 465 | 2.19 | 9 |
| B-171 | 246.7 | 374 | 2.20 | 9 |
| B-172 | 192.3 (DSC) | 363 | 1.82 | 7 |
| B-173 | 210.8 | 306 | 1.92 | 7 |
| B-174 | 235.1 | 276 | 1.03 | 4 |
| B-175 | n.d. | 430 | 4.26 | 7 |
| B-176 | n.d. | 376 | 3.71 | 7 |
| B-177 | 240 | 276 | 1.9 | 7 |
| B-178 | 258 | 377 | 1.35 | 9 |
| B-179 | >300 (dec) | 394 | 2.4 | 2 |

TABLE 2-continued

Analytical data - $R_t$ means retention time (in minutes), $[M + H]^+$ means the protonated mass of the compound, method refers to the method used for (LC)MS, dec means decomposition.

| Co. no. | mp (° C.) | [MH⁺] | Rt | LCMS method |
|---|---|---|---|---|
| B-180 | 242.2 (DSC) | 363 | 1.93 | 7 |
| B-181 | n.d. | 333 | 1.02 | 2 |
| B-182 | 301.9 (DSC) | 347 | 1.64 | 7 |
| B-183 | 248.3 | 296 | 2.14 | 7 |
| B-184 | n.d. | 339 | 0.5 | 3 |
| B-185 | n.d. | 305 | 0.36 | 3 |
| B-186a | n.d. | 391 | 2.58 | 4 |
| B-186b | n-d. | 391 | 2.70 | 4 |
| B-187 | n.d. | 339 | 2.46 | 4 |
| B-188 | 194.7 | 407 | 1.12 | 6 |
| B-189 | nd | nd | nd | |
| B-190 | nd | nd | nd | |
| B-191 | nd | 360 | 1.28 | 14 |
| B-192 | 203.5 | 410 | 1.97 | 7 |
| B-193 | 227.2 | 431 | 1.54 | 7 |
| B-194 | 237.5 | 419 | 1.32 | 7 |
| B-195 | nd | 423 | 1.41 | 4 |
| B-196 | 67.9 | 437 | 1.78 | 9 |
| B-197 | nd | 391 | 1.7 | 7 |
| B-198 | nd | 419 | 1.21 | 7 |
| B-199 | 221.5 | 447 | 1.65 | 7 |
| B-200 | 197.7 | 377 | 1.66 | 7 |
| B-201 | 209.3 | 449 | 1.87 | 7 |
| B-202 | nd | 467 | 1.28 | 12 |
| B-203 | nd | 435 | 1.39 | 4 |
| B-204 | 228.8 | 433 | 1.39 | 7 |
| B-205 | 213.8 | 389 | 1.53 | 7 |
| B-206 | nd | 417 | 1.78 | 7 |
| B-207 | 278.3 | 415 | 1.65 | 7 |
| B-208 | 235.1 | 415 | 1.57 | 7 |
| B-209 | 268.7 | 403 | 1.66 | 7 |
| B-210 | 279.9 | 403 | 1.59 | 7 |
| B-211 | 244.9 | 389 | 1.49 | 7 |
| B-212 | 244.5 | 377 | 1.29 | 7 |
| B-213 | nd | 403 | 1.45 | 7 |

Pharmacological Examples

The compounds provided in the present invention are inhibitors of PDE2, particularly of PDE2A, and to a lesser extent of PDE10, particularly of PDE10A, or of PDE2 and PDE10, particularly, of PDE2A and PDE10A. The behaviour of representative PDE2 inhibitors or PDE2 and PDE10 inhibitors according to Formula (I) is shown in Tables 3-5 below.

In Vitro Assay PDE2A

Human recombinant PDE2A (hPDE2A) was expressed in Sf9 cells using a recombinant rPDE10A baculovirus construct. Cells were harvested after 48 h of infection and the hPDE2A protein was purified by metal chelate chromatography on Ni-sepharose 6FF. Tested compounds were dissolved and diluted in 100% DMSO to a concentration 100 fold of the final concentration in the assay. Compound dilutions (0.4 μl) were added in 384 well plates to 20 μl of incubation buffer (50 mM Tris pH 7.8, 8.3 mM $MgCl_2$, 1.7 mM EGTA). 10 μl of hPDE2A enzyme in incubation buffer was added and the reaction was started by addition of 10 μl substrate to a final concentration of 10 μM cGMP and 0.01 μCi $^3$H-cGMP. The reaction was incubated for 45 minutes at room temperature. After incubation, the reaction was stopped with 20 μl of stop solution consisting of 17.8 mg/ml PDE SPA scintillation proximity assay) beads supplemented with 200 mM $ZnCl_2$. After sedimentation of the beads during 30 minutes the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve is fitted by a minimum sum of squares method to the plot of % of control value substracted with blanc value versus compound concentration and the half maximal inhibitory concentration ($IC_{50}$) value is derived from this curve.

In Vitro Assay PDE10A

Rat recombinant PDE10A (rPDE10A2) was expressed in Sf9 cells using a recombinant rPDE10A baculovirus construct. Cells were harvested after 48 h of infection and the rPDE10A protein was purified by metal chelate chromatography on Ni-sepharose 6FF. Tested compounds were dissolved and diluted in 100% DMSO to a concentration 100 fold of the final concentration in the assay. Compound dilutions (0.4 μl) were added in 384 well plates to 20 μl of incubation buffer (50 mM Tris pH 7.8, 8.3 mM $MgCl_2$, 1.7 mM EGTA). 10 μl of rPDE10A enzyme in incubation buffer was added and the reaction was started by addition of 10 μl substrate to a final concentration of 60 nM cAMP and 0.008 μCi $^3$H-cAMP. The reaction was incubated for 60 minutes at room temperature. After incubation, the reaction was stopped with 20 μl of stop solution consisting of 17.8 mg/ml PDE SPA (scintillation proximity assay) beads. After sedimentation of the beads during 30 minutes the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve is fitted by a minimum sum of squares method to the plot of % of control value subtracted with blank value versus compound concentration and the half maximal inhibitory concentration ($IC_{50}$) value is derived from this curve. The results of this test are shown in table 3 below.

TABLE 3

Pharmacological data for compounds according to the invention.

| Co. No. | $pIC_{50}$ PDE2 | $PIC_{50}$ PDE10 |
|---|---|---|
| B-1a | 8.37 | 7.23 |
| B-1b | 7.29 | 6.35 |
| B-2a | 7.53 | 6.53 |
| B-2b | 6.55 | 5.57 |
| B-3a | 8.55 | 7.36 |
| B-3b | 7.22 | 6.72 |
| B-4a | 8.08 | 7.61 |
| B-4b | n.t. | n.t. |
| B-5 | 8.12 | 7.6 |
| B-6a | 8.15 | 5.72 |
| B-6b | 6.85 | <5 |
| B-7 | 7.73 | 5.47 |
| B-8 | 7.69 | 6.42 |
| B-9 | 8.78 | 7.38 |
| B-10 | 9.54 | 7.67 |
| B-11 | 8.79 | 7.47 |
| B-12 | 7.67 | 6.57 |
| B-13 | 8.7 | 7.34 |
| B-14 | 8.15 | 7.43 |
| B-15 | 8.06 | 7.79 |
| B-16 | 8.28 | 7.57 |
| B-17a | 7.9 | 5.32 |
| B-17b | 8.13 | 5.39 |
| B-18 | 8.11 | 5.79 |
| B-19 | 8.64 | 7.47 |

TABLE 3-continued

Pharmacological data for compounds according to the invention.

| Co. No. | $pIC_{50}$ PDE2 | $PIC_{50}$ PDE10 |
|---|---|---|
| B-20 | 7.69 | 6.8 |
| B-21 | 8.19 | 7.38 |
| B-22 | 8.11 | 7.05 |
| B-23 | 8.86 | 7.86 |
| B-24 | 7.4 | 6.28 |
| B-25 | 8.41 | 7.81 |
| B-26 | 7.76 | 5.9 |
| B-27 | 8.63 | 7.53 |
| B-28 | 8.64 | 7.88 |
| B-29 | 7.35 | 6.42 |
| B-30 | 8.24 | 7.61 |
| B-31 | 9.69 | 8.09 |
| B-32 | 9.6 | 8.18 |
| B-33 | 9.55 | 7.91 |
| B-34 | 9.43 | 7.92 |
| B-35 | 9.38 | 8.08 |
| B-36 | 9.34 | 7.95 |
| B-37 | 9.2 | 7.69 |
| B-38 | 9.14 | 7.6 |
| B-39 | 9 | 7.62 |
| B-40 | 8.99 | 7.73 |
| B-41 | 8.87 | 7.35 |
| B-42 | 8.82 | 7.53 |
| B-43 | 8.79 | 7.36 |
| B-44 | 8.75 | 7.45 |
| B-45 | 8.71 | 7.13 |
| B-46 | 8.71 | 7.7 |
| B-47 | 8.69 | 6.84 |
| B-48 | 8.68 | 7.21 |
| B-49 | 8.63 | 7.11 |
| B-50 | 8.63 | 7.96 |
| B-51 | 8.6 | 6.81 |
| B-52 | 8.56 | 7.13 |
| B-53 | 8.51 | 7.43 |
| B-54 | 8.46 | 7.03 |
| B-55 | 8.46 | 7.97 |
| B-56 | 8.4 | 7.35 |
| B-57 | 8.33 | 7.74 |
| B-58 | 8.32 | 5.73 |
| B-59 | 8.31 | 7.63 |
| B-60 | 8.3 | 8.18 |
| B-61 | 8.26 | 7.7 |
| B-62 | 8.26 | 7.71 |
| B-63 | 8.25 | 8.03 |
| B-64 | 8.24 | 7.52 |
| B-65 | 8.23 | 6.6 |
| B-66 | 8.23 | 7.43 |
| B-67 | 8.21 | 7.81 |
| B-68 | 8.21 | 6.75 |
| B-69 | 8.21 | 7.11 |
| B-70 | 8.21 | 6.58 |
| B-71 | 8.2 | 7.72 |
| B-72 | 8.19 | 6.49 |
| B-73 | 8.17 | 7.17 |
| B-74 | 8.16 | 6.89 |
| B-75 | 8.16 | 7.2 |
| B-76 | 8.15 | 7.34 |
| B-77 | 8.13 | 7.11 |
| B-78 | 8.12 | 7.03 |
| B-79 | 8.09 | 5.72 |
| B-80 | 8.07 | 6.13 |
| B-81 | 8.02 | 7.43 |
| B-82 | 8.02 | 7.07 |
| B-83 | 8.01 | 6.99 |
| B-84 | 7.98 | 6.98 |
| B-85 | 7.97 | 6.91 |
| B-86 | 7.96 | 7.42 |
| B-87 | 7.95 | 7.57 |
| B-88 | 7.94 | 5.67 |
| B-89 | 7.93 | 7.3 |
| B-90 | 7.92 | 7.3 |
| B-91 | 7.92 | 6.57 |
| B-92 | 7.92 | 6.33 |
| B-93 | 7.89 | 7.41 |
| B-94 | 7.89 | 7.19 |

TABLE 3-continued

Pharmacological data for compounds according to the invention.

| Co. No. | $pIC_{50}$ PDE2 | $PIC_{50}$ PDE10 |
|---|---|---|
| B-95 | 7.88 | 5.76 |
| B-96 | 7.85 | 6.7 |
| B-97 | 7.85 | 7.11 |
| B-98 | 7.84 | 6.72 |
| B-99 | 7.83 | 7.3 |
| B-100 | 7.83 | 5.91 |
| B-101 | 7.75 | 5.26 |
| B-102 | 7.74 | 6.79 |
| B-103 | 7.73 | 6.75 |
| B-104 | 7.72 | 6.69 |
| B-105 | 7.72 | 5.84 |
| B-106 | 7.71 | 7.05 |
| B-107 | 7.7 | 6.97 |
| B-108 | 7.69 | 7.44 |
| B-109 | 7.69 | 6.07 |
| B-110 | 7.69 | 7.35 |
| B-111 | 7.68 | 5.75 |
| B-112 | 7.66 | 5.83 |
| B-113 | 7.64 | 7.48 |
| B-114 | 7.61 | 6.98 |
| B-115 | 7.61 | 5.95 |
| B-116 | 7.61 | 6.29 |
| B-117 | 7.6 | 6.04 |
| B-118 | 7.59 | 6.93 |
| B-119 | 7.52 | 5.21 |
| B-120 | 7.57 | 5.45 |
| B-121 | 7.47 | 6.84 |
| B-122 | 7.56 | 6.48 |
| B-123 | 7.56 | 6.38 |
| B-124 | 7.56 | 6.45 |
| B-125 | 7.56 | 5.51 |
| B-126 | 7.55 | 5.61 |
| B-127 | 7.54 | 5.74 |
| B-128 | 7.54 | 6.64 |
| B-129 | 7.54 | 6.05 |
| B-130 | 7.54 | 6.01 |
| B-131 | 7.53 | 6.88 |
| B-132 | 7.53 | 5.75 |
| B-133 | 7.52 | 5.91 |
| B-134 | 7.52 | 5.96 |
| B-135 | 7.52 | 6.23 |
| B-136 | 7.5 | 5.9 |
| B-137 | 7.48 | 6 |
| B-138 | 7.47 | 6.15 |
| B-139 | 7.46 | 7.2 |
| B-140 | 7.46 | 6.55 |
| B-141 | 7.45 | 5.8 |
| B-142 | 7.44 | 6.5 |
| B-143 | 7.42 | 5.87 |
| B-144 | 8.35 | 7.5 |
| B-145 | 7.39 | 6.62 |
| B-146 | 7.39 | 5.99 |
| B-147 | 7.35 | 7.06 |
| B-148 | 7.34 | 5.07 |
| B-149 | 7.35 | 5.38 |
| B-150 | 7.31 | <5 |
| B-151 | n.t. | n.t. |
| B-151a | 7.36 | 6.04 |
| B-152 | 7.3 | 5.41 |
| B-153 | 7.28 | <5 |
| B-154 | 7.28 | 6.42 |
| B-155 | 7.22 | 5.04 |
| B-156 | 7.21 | 5.1 |
| B-157 | 7.24 | 6.55 |
| B-158 | 7.22 | 6.22 |
| B-159 | 7.22 | 6.46 |
| B-160 | 7.22 | 5.61 |
| B-161 | 7.22 | 5.06 |
| B-162 | 7.17 | 6.06 |
| B-163 | 7.16 | 5.94 |
| B-164 | 7.16 | 5.6 |
| B-165 | 7.09 | 6.3 |
| B-166 | 7.02 | 6.55 |
| B-167 | 7.02 | 6.58 |
| B-168 | 7.01 | 6.76 |

TABLE 3-continued

Pharmacological data for compounds according to the invention.

| Co. No. | $pIC_{50}$ PDE2 | $PIC_{50}$ PDE10 |
|---|---|---|
| B-169 | 6.99 | 5.55 |
| B-170 | 6.99 | 5.44 |
| B-171 | 6.93 | 6.13 |
| B-172 | 6.9 | 5.11 |
| B-173 | 6.87 | 6.01 |
| B-174 | 6.86 | n.t. |
| B-175 | 6.83 | <5 |
| B-176 | 6.8 | <5 |
| B-177 | 6.79 | n.t. |
| B-178 | 6.71 | <5 |
| B-179 | 6.7 | 5.9 |
| B-180 | 6.69 | 5.75 |
| B-181 | 6.62 | 5.26 |
| B-182 | 6.62 | 5.38 |
| B-183 | 6.5 | n.t. |
| B-184 | n.t. | n.t. |
| B-185 | n.t. | n.t. |
| B-186a | n.t. | n.t. |
| B-186b | n.t | n.t |
| B-187 | n.t. | n.t. |
| B-188 | n.t. | n.t. |
| B-189 | n.t. | n.t. |
| B-190 | n.t. | n.t. |
| B-191 | n.t. | n.t. |
| B-192 | 7.74 | 5.04 |
| B-193 | 7.65 | 5.44 |
| B-194 | 7.53 | 5.11 |
| B-195 | 7.37 | 5.45 |
| B-196 | 7.19 | 5.06 |
| B-197 | 7.13 | 5.03 |
| B-198 | 7.05 | 5.23 |
| B-199 | 7.05 | 5.41 |
| B-200 | 7.04 | <5 |
| B-201 | 7.02 | 5.29 |
| B-202 | 6.93 | <5 |
| B-203 | 6.91 | 5.11 |
| B-204 | 6.88 | 5.09 |
| B-205 | 6.87 | <5 |
| B-206 | 6.87 | <5 |
| B-207 | 6.62 | <5 |
| B-208 | 6.56 | <5 |
| B-209 | 6.52 | <5 |
| B-210 | 6.48 | 5.84 |
| B-211 | 6.46 | <5 |
| B-212 | 6.45 | 5.21 |
| B-213 | 6.43 | <5 |

$pIC_{50}$ corresponds to the -log $IC_{50}$ expressed in mol/L.
n.t. means not tested.

Effect of PDE-Inhibitors

Ex-Vivo Studies in Rat

Upon arrival, the animals (body weight 210-240 g) were housed in groups of 5 and fed normal chow at libitum.

Compounds and/or solvent were administered either orally, subcutaneously or IV. Depending on the experimental setup, the animals were sacrificed by microwave irradiation (Muromachi, MMW-05) for 1.5 sec at 5 kW, either 15, 30, 45 60, 120 or 240 min after drug/solvent administration. After microwave, the rats were decapitated and the heads cooled immediately with ice cold physiological saline. The scalp was opened and the brain, including cerebellum was removed and different brain regions (striatum, hippocampus, cortex and/or cerebellum) were dissected and transferred into pre-weighed homogenization tubes (Collection Micro-tubes cat nr 19560, Qiagen) containing a steel ball (Stainless steel beads 5 mm, cat nr 69989, Qiagen), and kept on dry ice. 10 vol (w/v) of 0.1N HCl were added. The tissue was homogenized for 3 min at 30 Hz using a Tissuelyser from Qiagen.

The homogenate was transferred into an Eppendorf tube (1.5 ml) and after centrifugation for 15 min at 1600 g in a pre-cooled (4C) Eppendorf centrifuge, the supernatant was collected and stored at −80° C. until analysis.

Cyclic-GMP levels were determined on ¼ (striatum, hippocampus, cortex) or 1/10 (cerebellum) diluted samples using the cGMP Complete EIA kit from Enzo Life Sciences (cat nr ADI-900-164).

Cyclic-AMP levels were determined on 1/10 and 1/25 diluted samples using the LANCE Ultra cAMP kit from Perkin Elmer (code TRF0263).

Results were calculated by GraphPadPrism. The results of this test are shown in table 4 below.

The cAMP and cGMP levels were measured in the rat brain (hippocampus and striatum) to establish in vivo target engagement and central pharmacological effect of PDE2 inhibition. PDE2 inhibition results in a marked increase in brain cGMP levels. The NO/cGMP signaling pathway has been shown to play an important role in the process underlying learning and memory, synaptic plasticity and neurogenesis, and in the regulation of corticostriatal synaptic transmission and motor behavior. The measured elevation of cGMP in brain tissue supports the further investigation of the use of PDE2 inhibitors in conditions with impaired NO/cGMP signaling such as cognitive dysfunction in psychiatric disorders, Alzheimer's disease (Mennitti, F. S. et al. Nature Rev. Drug Discovery 2006, 5, 660-669; Baratti, C. M., Boccia, M. M. Behay. Pharmacol. 1999; 10: 731-737; Prickaerts, J. et al. Neuroscience 2002; 113:349-359; Domek-Lopacińska K U, Strosznajder JB MolNeurobiol. 2010; 41(2-3):129-37), major depression (Reierson, G. W. et al. Current Neuropharmacology 2011; 9:715-727) and movement disorders as Parkinson and Huntington disease (West, A. R. and Tseng K. Y. Neuroscience, 2011; 5:55-64; Kumar P, et al. Behav Pharmacol. 2010 May; 21(3):217-30).

TABLE 4 cAMP and cGMP levels measured in the rat brain with compounds according to the invention.

| Compound | Hippocampus | | Striatum | |
|---|---|---|---|---|
| dosed (10 mg/kg s.c., −1 h) | cAMP (% of Control) | cGMP (% of Control) | cAMP (% of Control) | cGMP (% of Control) |
| B-17a | 91 ± 9 | 298 ± 52** | 101 ± 21 | 240 ± 70** |
| B-88 | 117 ± 20 | 150 ± 42 | 88 ± 12 | 121 ± 20 |
| B-197 | 122 ± 10 | 104 ± 32 | 89 ± 6 | 128 ± 26 |

**p < 0.005 student T-test

Reversal of Apomorphine-Induced Agitation in Rats (APO)

Apomorphine (1.0 mg/kg, i.v.)-induced agitation was scored every 5 min over the first hour after injection of apomorphine. The score system was: (3) pronounced, (2) moderate, (1) slight, and (0) absent. Criteria for drug-induced inhibition of agitation: fewer than 6 scores of 3 (0.16% false positives; n=2966), fewer than 6 scores of ≥2 (0.0% false positives) or fewer than 7 scores of ≥1 (0.0% false positives). For the present purpose, the cumulative agitation score over the whole 60-min observation period was used as a measure to describe the maximum effect (Max effect). The results of this test are shown in table 5.

TABLE 5

Reversal of Apomorphine-induced Agitation in Rats data for compounds according to the invention.

| | PO | | | SC | | |
|---|---|---|---|---|---|---|
| Co. No. | LAD | Max effect | Dose at Max Effect | LAD | Max effect | Dose at max effect |
| B-9 | >2.5 | 22 | 2.5 | | | |
| B-104 | | | | >2.5 | 21 | 2.5 |
| B-54 | >2.5 | 22 | 2.5 | | | |
| B-77 | >2.5 | 21 | 2.5 | | | |
| B-1a | >2.5 | 22 | 2.5 | | | |
| B-65 | >10 | 21 | 10 | | | |
| B-10 | >2.5 | 21 | 2.5 | | | |
| B-38 | 2.5 | 19 | 2.5 | | | |
| B-34 | >2.5 | 22 | 2.5 | | | |
| B-52 | 10 | 19 | 10 | | | |
| B-56 | >10 | 21 | 10 | | | |
| B-83 | | | | >10 | 29 | 2.5 |
| B-12 | | | | 10 | 19 | 10 |
| B-45 | | | | >10 | 21 | 10 |
| B-49 | >10 | 24 | 10 | | | |
| B-66 | >10 | 21 | 10 | | | |
| B-35 | >10 | 22 | 10 | | | |
| B-36 | | | | >10 | 21 | 10 |
| B-48 | | | | >10 | 24 | 10 |
| B-46 | >10 | 21 | 10 | | | |
| B-41 | | | | >10 | 22 | 10 |
| B-32 | >10 | 22 | 10 | | | |
| B-40 | >10 | 22 | 10 | | | |
| B-78 | >10 | 21 | 10 | | | |
| B-53 | >10 | 24 | 10 | | | |
| B-47 | | | | >10 | 22 | 10 |
| B-42 | >10 | 22 | 10 | | | |
| B-3b | >10 | 22 | 10 | | | |
| B-3a | >10 | 22 | 10 | | | |
| B-71 | | | | 10 | 15 | 10 |
| B-67 | >10 | 21 | 10 | | | |
| B-13 | 10 | 19 | 10 | | | |
| B-113 | | | | 10 | 8 | 10 |
| B-16 | | | | >2.5 | 21 | 2.5 |
| B-60 | >10 | 21 | 10 | | | |
| B-15 | | | | 2.5 | 10 | 10 |
| B-14 | >10 | 21 | 10 | | | |
| B-107 | | | | >10 | 20.5 | 10 |
| B-44 | >10 | 21 | 10 | | | |
| B-108 | >10 | 19 | 10 | | | |
| B-11 | >10 | 19 | 10 | | | |
| B-43 | 10 | 19 | 10 | | | |
| B-39 | >10 | 21 | 10 | | | |
| B-74 | >10 | 21 | 10 | | | |
| B-19 | | | | 5 | 14 | 5 |
| B-20 | | | | >10 | 21 | 10 |
| B-96 | >10 | 21 | 10 | | | |
| B-51 | >10 | 21 | 10 | | | |
| B-68 | | | | >10 | 22 | 10 |
| B-81 | | | | 10 | 19 | 10 |
| B-76 | | | | 10 | 16 | 10 |
| B-73 | | | | 10 | 19 | 10 |
| B-90 | | | | >10 | 25 | 10 |
| B-50 | | | | >10 | 22 | 10 |
| B-139 | >10 | 22 | 10 | | | |
| B-93 | | | | 10 | 7 | 10 |
| B-110 | | | | >10 | 21 | 10 |
| B-94 | | | | >5 | 24 | 5 |
| B-61 | | | | 10 | 15 | 10 |
| B-62 | | | | >10 | 21 | 10 |
| B-57 | | | | >10 | 22 | 10 |
| B-55 | | | | >10 | 22 | 10 |
| B-59 | | | | 10 | 15 | 10 |
| B-63 | | | | 10 | 19 | 10 |
| B-75 | | | | 2.5 | 15 | 10 |
| B-82 | | | | 2.5 | 9 | 10 |
| B-23 | | | | 0.63 | 1 | 40 |
| B-21 | >10 | 24 | 10 | | | |
| B-89 | | | | >5 | 24 | 5 |
| B-131 | 10 | 17 | 10 | | | |
| B-118 | | | | 10 | 17 | 10 |

TABLE 5-continued

Reversal of Apomorphine-induced Agitation in Rats data for compounds according to the invention.

| | PO | | | SC | | |
|---|---|---|---|---|---|---|
| Co. No. | LAD | Max effect | Dose at Max Effect | LAD | Max effect | Dose at max effect |
| B-114 | >10 | 24 | 10 | | | |
| B-168 | 10 | 16 | 10 | | | |
| B-4a | >10 | 21 | 10 | | | |
| B-167 | 10 | 19 | 10 | | | |
| B-91 | | | | >10 | 21 | 10 |
| B-25 | 10 | 19 | 10 | | | |
| B-85 | >10 | 21 | 10 | | | |
| B-5 | >10 | 21 | 10 | | | |
| B-84 | >10 | 21 | 10 | | | |
| B-97 | | | | 10 | 19 | 10 |
| B-102 | | | | >10 | 21 | 10 |
| B-140 | | | | >10 | 24 | 10 |
| B-142 | | | | >10 | 22 | 10 |
| B-128 | | | | >10 | 21 | 10 |
| B-70 | | | | >10 | 24 | 10 |
| B-145 | | | | >10 | 22 | 10 |
| B-72 | | | | >10 | 23 | 10 |
| B-103 | | | | >10 | 21 | 10 |
| B-121 | | | | >10 | 21 | 10 |
| B-17a | | | | >40 | 23 | 40 |
| B-142 | | | | >10 | 22 | 10 |

LAD means lowest active dose, defined as the lowest dose at which ≥67% tested animals (when ≥3 animals are tested) respond to the criteria for drug-induced inhibition of agitation;
PO means oral route;
SC means subcutaneous route.

PDE2 [$^{18}$F]B-23: Preclinical Data: Biodistribution, Radiometabolite Analysis and μPET Baseline

Biodistribution Study

The biodistribution study was carried out in male Wistar rats (body weight 320-370 g) at 2 min, 10 min and 30 min post injection (p.i.) (n=3/time point). Rats were injected with about 1.1 MBq of the tracer via tail vein under anesthesia (2.5% isoflurane in $O_2$ at 1 L/min flow rate) and sacrificed by decapitation at above specified time points. Blood and major organs were collected in tared tubes and weighed. The radioactivity in blood, organs and other body parts was measured using an automated gamma counter. The distribution of radioactivity in different parts of the body at different time points p.i. of the tracer was calculated and expressed as percentage of injected dose (% ID), and as standardized uptake values (SUV) for the selected organs. % ID is calculated as counts per minute (cpm) in organ/total cpm recovered. SUVs are calculated as (radioactivity in cpm in organ/weight of the organ in g)/(total counts recovered/body weight in g). For calculation of total radioactivity in blood, blood mass was assumed to be 7% of the body mass.

The results are presented in Tables 6 and 7. Table 6 shows the % injected dose (% ID) values at 2 min, 10 min and 30 min p.i. of the radiotracer. The total brain uptake of the tracer at 2 min p.i. was high (~1.2%), with ~1.0% of the ID in the cerebrum and ~0.1% in the cerebellum. At 10 min p.i. the % ID in the brain was decreased to 0.2%. At 30 min p.i. this was 0.1% ID. At 2 min p.i. about 6.7% of the injected dose was present in the blood, and this cleared to 4.1% by 30 min after injection of the tracer. The compound was cleared mainly by hepatobiliary system as there was in total 49% of ID present in the liver and intestines at 30 min after injection of the radiotracer, and to a lesser extent via the renal pathway with 19% ID in the urine and the kidneys at 30 min p.i. Table 7 shows the radiotracer concentration (SUV values) for the studied brain regions and the blood at 2 min, 10 min and 30 min p.i. At the three studied time points the highest radioactivity concentration was observed in the striatum and the lowest concentration in the cerebellum. Table 8 shows the 2 min-to-10 min and the 2 min-to-30 min ratios of SUV values for different regions of the brain and the blood. Fast wash-out was observed for all studied brain regions (ratios >1). The slowest wash-out was observed for the striatum (2 min-to-30 min ratio=7.1), while the cortex had the fastest clearance (2 min-to-30 min ratio=15.7). The wash-out from blood was slow (2 min-to-30 min ratio=1.6)

TABLE 6

Biodistribution in normal rats at 2, 10 and 30 min p.i.

| | % ID [a] | | |
|---|---|---|---|
| Organ | 2 min | 10 min | 30 min |
| Urine | 0.25 ± 0.1 | 0.61 ± 0.5 | 10.80 ± 1.2 |
| Kidneys | 4.68 ± 0.7 | 6.02 ± 1.2 | 8.24 ± 0.3 |
| Liver | 30.79 ± 4.6 | 37.83 ± 3.3 | 29.30 ± 4.8 |
| Spleen + Pancreas | 1.57 ± 0.1 | 0.42 ± 0.0 | 0.32 ± 0.1 |
| Lungs | 2.27 ± 1.2 | 0.68 ± 0.1 | 0.46 ± 0.0 |
| Heart | 0.81 ± 0.0 | 0.23 ± 0.0 | 0.12 ± 0.0 |
| Stomach | 2.44 ± 0.3 | 2.77 ± 0.8 | 4.81 ± 0.3 |
| Intestines | 9.51 ± 1.1 | 10.97 ± 1.5 | 19.75 ± 5.6 |
| Striatum | 0.098 ± 0.010 | 0.031 ± 0.005 | 0.012 ± 0.001 |
| Hippocampus | 0.036 ± 0.002 | 0.006 ± 0.001 | 0.003 ± 0.001 |
| Cortex | 0.086 ± 0.017 | 0.016 ± 0.004 | 0.006 ± 0.003 |
| Rest of cerebrum | 0.809 ± 0.130 | 0.159 ± 0.006 | 0.064 ± 0.024 |
| Cerebrum total | 1.030 ± 0.130 | 0.212 ± 0.006 | 0.084 ± 0.026 |
| Cerebellum | 0.096 ± 0.022 | 0.020 ± 0.002 | 0.011 ± 0.005 |
| Blood | 6.69 ± 0.4 | 6.27 ± 0.5 | 4.10 ± 0.6 |
| Carcass | 42.54 ± 4.8 | 37.39 ± 4.9 | 23.75 ± 1.9 |

Data are expressed as mean ± SD; n = 3 per time point;
[a] Percentage of injected dose calculated as cpm in organ/total cpm recovered

TABLE 7

Tracer concentration in different brain regions and blood at 2, 10 and 30 min p.i.

| | SUV * | | |
|---|---|---|---|
| Organ | 2 min | 10 min | 30 min |
| Striatum | 4.36 ± 0.42 | 1.77 ± 0.08 | 0.61 ± 0.20 |
| Hippocampus | 1.87 ± 0.22 | 0.33 ± 0.04 | 0.14 ± 0.04 |
| Cortex | 2.36 ± 0.48 | 0.53 ± 0.02 | 0.15 ± 0.04 |
| Rest of cerebrum | 2.63 ± 0.41 | 0.57 ± 0.02 | 0.22 ± 0.08 |
| Cerebellum | 1.22 ± 0.23 | 0.27 ± 0.02 | 0.12 ± 0.04 |
| Blood | 0.96 ± 0.05 | 0.90 ± 0.08 | 0.59 ± 0.08 |

Data are expressed as mean ± SD; n = 3 per time point;
* standard uptake values are calculated as (radioactivity in cpm in organ/weight of the organ in g)/(total counts recovered/body weight in g).

TABLE 8

Clearance of the tracer from different regions of the brain and the blood calculated as the 2 min-to-10 min ratio and the 2 min-to-30 min ratio of SUV values.

| | 2 min/10 min | 2 min/30 min |
|---|---|---|
| Striatum | 2.5 | 7.1 |
| Hippocampus | 5.7 | 13.4 |
| Cortex | 4.5 | 15.7 |
| Rest of cerebrum | 4.6 | 11.9 |
| Cerebellum | 4.5 | 10.2 |
| Blood | 1.1 | 1.6 |

Plasma and Brain Radiometabolite Analysis

The metabolic stability of the tracer was studied in normal rats by determination of the relative amounts of parent tracer and radiometabolites in plasma and brain at 2 min and 10 min p.i. of the tracer. After intravenous (i.v.) administration of about 37 MBq of the tracer via tail vein under anesthesia (2.5% isoflurane in $O_2$ at 1 L/min flow rate), rats were sacrificed by decapitation at 2 min p.i. (n=1), blood was collected in lithium heparin containing tubes (4.5 mL LH PST tubes; BD vacutainer, BD, Franklin Lakes, USA) and stored on ice. Brain was dissected and rinsed with saline (decapitation was preferred since it was difficult to have the rat perfused already at 2 min p.i.). For the 10 min timepoint, rats (n=1) were injected with about 37 MBq of tracer and sacrificed at 10 min p.i by administering an overdose of Nembutal (CEVA Sante Animale, 200 mg/kg intraperitoneal). The rats were perfused by injection of saline into the left ventricle until the liver turned pale. During perfusion, blood was collected and stored on ice. Brain was isolated.

For the brain radiometabolite analysis, cerebrum and cerebellum were separated and homogenized in 3 mL and 2 mL of acetonitrile respectively, for about 3 min. A volume of 1 mL of this homogenate was diluted with an equal volume of water and 1 mL of the supernatant was filtered through a 0.22 μm filter (Millipore, Bedford, USA). About 0.5 mL of the filtrate was diluted with 0.1 mL of water and spiked with 10 μL of authentic reference material (1 mg/mL) for identification. A volume of 0.5 mL of the homogenate extracts were injected onto an HPLC system consisting of an analytical XBridge column ($C_{18}$, 3.5 μm, 3 mm×100 mm, Waters) eluted with a mixture of 0.05 M sodium acetate (pH 5.5) and $CH_3CN$ (76:24 v/v) at a flow rate of 0.8 mL/min. The HPLC eluate was collected as 0.8-mL fractions (fraction collection per minute) after passing through the UV detector (254 nm), and radioactivity in the fractions was measured using an automated gamma counter. The peak corresponding to the intact tracer eluted around 10 min, the polar radiometabolite(s) around 5 min. An overview of the results from the rat brain radiometabolite analysis is presented in Table 9. At 2 min p.i., almost all of the recovered radioactivity in cerebrum and in cerebellum was present as intact tracer. At 10 min p.i., the amount of polar radiometabolite(s) in cerebrum was more or less similar as at 2 min p.i., for cerebellum the % of intact tracer was decreased to 82%. No apolar radiometabolites were detected in brain.

TABLE 9

Relative percentages of intact tracer and radiometabolites in perfused rat cerebrum and cerebellum at 2 and 10 min p.i. of the radiotracer (n = 1/time point).

| | 2 min p.i. | | 10 min p.i. | |
|---|---|---|---|---|
| % | Cerebrum | Cerebellum | Cerebrum | Cerebellum |
| polar metabolite(s) | 2 | 4 | 8 | 18 |
| intact tracer | 98 | 96 | 92 | 82 |

For the plasma radiometabolite analysis, the blood was centrifugated for 10 min at 3000 rpm to separate the plasma. A volume of about 0.1 mL of plasma sample was isolated and spiked with about 10 μL of authentic non-radioactive reference material (1 mg/mL) for identification. The plasma was then injected onto an HPLC system consisting of a Chromolith Performance column ($C_{18}$, 3 mm×100 mm, Merck) that was eluted with mixtures of 0.05 M NaOAc pH 5.5 (solvent A) and acetonitrile (solvent B). The following method was used for the analysis: isocratic elution with 100% A for 4 min at a flow rate of 0.5 mL/min, then linear gradient to 90% B by 14 min at a flow rate of 1 mL/min, and isocratic elution with a mixture of 10% A and 90% B at a flow rate of 1 mL/min until 17 min. After passing through an in-line UV detector (254 nm) and over a 3 in. NaI(Tl) scintillation detector connected to a single channel analyzer (Gabi box, Raytest, Straubenhardt Germany), the HPLC eluate was collected per minute using an automatic fraction collector. The radioactivity in all fractions was measured using an automated gamma counter. The peak corresponding to the intact tracer eluted at ~11 min. Polar radiometabolite(s) were eluting from 1 to 3 min. Slightly more polar radiometabolites (relatively to the polarity of the intact tracer) were eluting just before the intact tracer. An overview of the results from the plasma radiometabolite analysis is presented in Table 10. Faster metabolisation is observed in plasma compared to brain. At 2 min p.i., about 70% of the recovered radioactivity was present as intact tracer. Two more polar radiometabolites (M1, M3) were observed of which one (M3) was closely eluting to the intact tracer. At 10 min p.i., the presence of a large amount of a third polar metabolite (M2, also closely eluting to the parent compound) was observed which accounted for about 60% of the recovered radioactivity. At 10 min p.i., only ~20% of the recovered radioactivity was still present as intact tracer. No apolar radiometabolites were detected in plasma.

TABLE 10

Relative percentages of intact tracer and radiometabolites in rat plasma at 2 and 10 min p.i. of the radiotracer (n = 1/time point)

| % in plasma | 2 min | 10 min |
|---|---|---|
| Polar metabolite M1 | 16 | 10 |
| Polar metabolite M2 | — | 61 |
| Polar metabolite M3 | 14 | 12 |
| Intact tracer | 70 | 18 |

MicroPET Imaging Studies

Imaging experiments were performed on a Focus™ 220 microPET scanner (Concorde Microsystems, Knoxyille, Tenn., USA) using male Wistar rats with body weight varying between 200 and 300 g. During all scan sessions, animals were kept under gas anesthesia (2.5% isoflurane in $O_2$ at 1 L/min flow rate). Dynamic scans of 60 min were acquired in list mode. After reconstruction of the images, they were semi-automatically co-registered with a [$^{11}$C] raclopride template of the rat brain, and volumes of interest (VOIs) were generated for different anatomical brain structures (striatum, cerebral cortex and cerebellum) from which time-activity curves (TAC) were constructed for each individual image, using PMOD software (PMOD Technologies Ltd.). Normalization for body weight of the animal and injected dose was done. The radioactivity concentration in the different brain regions was expressed as SUV (standardized uptake value) as a function of time post injection of the radiotracer. Rats (n=4) were injected with about 74 MBq of high specific activity formulation of the tracer via tail vein under anesthesia (2.5% isoflurane in $O_2$ at 1 L/min flow rate) and were scanned baseline for 60 min. High intensity signal was observed in the striatum with only background radioactivity in the cerebellum. After injection of the tracer, there was a high initial uptake of the radiotracer in all studied brain regions in accordance with the results of the biodistribution studies: the highest concentration at 2 min p.i. was observed for striatum followed by hippocampus and cortex, followed by cerebellum. After this initial high uptake due to the blood pool activity, the tracer was cleared from all studied brain regions. Fastest clearance was observed for the cerebellum, the brain region with minimal expression of PDE2. Clearance from hippocampus and cortex were similar and slower compared to the wash-out from the cerebellum. The slowest wash-out was observed for striatum.

The (striatum-cerebellum)/cerebellum ratios (S—C/C ratios) were calculated. This ratio provides the relative difference in tracer uptake between striatum and the 'reference region' cerebellum.

Peak S—C/C ratios (average of 2.8, n=4) were obtained at about 5 min p.i. and these ratios remained around this value until about 15 min p.i., after which the ratio started to decrease due to clearance of the radioactivity from striatum.

Prophetic Composition Examples

"Active ingredient" as used throughout these examples relates to a final compound of formula (I), the pharmaceutically acceptable salts thereof, the solvates and the stereochemically isomeric forms thereof.

Typical examples of recipes for the formulation of the invention are as follows:

| 1. Tablets | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

| 4. Ointment | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound selected from the group consisting of 1-(5-Butoxypyridin-3-yl)-4-methyl-8-(morpholin-4-ylmethyl)[1,2,4]triazolo[4,3-a]quinoxaline, or a hydrochloride salt thereof, or an oxalate salt thereof;

1-(5-Butoxy-2-chlorophenyl)-4-methyl-8-(morpholin-4-ylmethyl)[1,2,4]triazolo[4,3-a]quinoxaline or a hydrochloride salt thereof;

1-(2-Chloro-6-fluorophenyl)-4-methyl-8-(morpholin-4-ylmethyl)[1,2,4]triazolo[4,3-a]quinoxaline;

1-[2-Chloro-6-($^{18}$F)fluorophenyl]-4-methyl-8-(morpholin-4-ylmethyl)[1,2,4]triazolo[4,3-a]quinoxaline;

1-(2-Chloro-5-ethoxyphenyl)-4-methyl-8-(morpholin-4-ylmethyl)[1,2,4]triazolo[4,3-a]quinoxaline or a hydrochloride salt thereof;

1-(5-Butoxy-2-chlorophenyl)-4-methyl-8-(pyrrolidin-1-ylmethyl)[1,2,4]triazolo[4,3-a]quinoxaline or a hydrochloride salt thereof;

4-Methyl-8-(morpholin-4-ylmethyl)-1-(5-propoxypyridin-3-yl)[1,2,4]triazolo[4,3-a]quinoxaline or a hydrochloride salt thereof;

1-[2-Chloro-5-(1-methylethoxy)phenyl]-8-[(4-fluoropiperidin-1-yl)methyl]-4-methyl[1,2,4]triazolo[4,3-a]quinoxaline or a hydrochloride salt thereof;

1-(2-Chloro-5-ethoxyphenyl)-8-[(4-fluoropiperidin-1-yl)methyl]-4-methyl[1,2,4]triazolo[4,3-a]quinoxaline or a hydrochloride salt thereof;

1-(5-Butoxy-2-chlorophenyl)-4-methyl-8-[(4-methylpiperazin-1-yl)methyl][1,2,4]triazolo[4,3-a]quinoxaline or a hydrochloride salt thereof;

1-[5-(2-Fluoroethoxy)pyridin-3-yl]-4-methyl-8-(morpholin-4-ylmethyl)[1,2,4]triazolo[4,3-a]quinoxaline;

1-[5-(Cyclopropylmethoxy)pyridin-3-yl]-8-[(4-fluoropiperidin-1-yl)methyl]-4-methyl[1,2,4]triazolo[4,3-a]quinoxaline or a hydrochloride salt thereof;

1-[5-(Cyclopropylmethoxy)pyridin-3-yl]-4-methyl-8-(morpholin-4-ylmethyl)[1,2,4]triazolo[4,3-a]quinoxaline or a hydrochloride salt thereof;

1-(5-Butoxypyridin-3-yl)-4-methyl-8-(pyrrolidin-1-ylmethyl)[1,2,4]triazolo[4,3-a]quinoxaline or a hydrochloride salt thereof;

1-[5-(Ethoxymethyl)pyridin-3-yl]-4-methyl-8-(morpholin-4-ylmethyl)[1,2,4]triazolo[4,3-a]quinoxaline or a hydrochloride salt thereof;

1-[5-(Cyclopropylmethoxy)pyridin-3-yl]-4-methyl-8-(pyrrolidin-1-ylmethyl)[1,2,4]triazolo[4,3-a]quinoxaline or a hydrochloride salt thereof;

1-[5-(2-Methoxyethoxy)pyridin-3-yl]-4-methyl-8-(morpholin-4-ylmethyl)[1,2,4]triazolo[4,3-a]quinoxaline;

1-(5-Butoxypyridin-3-yl)-8-[(4-fluoropiperidin-1-yl)methyl]-4-methyl[1,2,4]triazolo[4,3-a]quinoxaline or a hydrochloride salt thereof;

1-[5-(2-Methoxyethyl)pyridin-3-yl]-4-methyl-8-(morpholin-4-ylmethyl)[1,2,4]triazolo[4,3-a]quinoxaline or a hydrochloride salt thereof;

1-[5-(2-Methoxyethyl)pyridin-3-yl]-4-methyl-8-(morpholin-4-ylmethyl)[1,2,4]triazolo[4,3-a]quinoxaline or a hydrochloride salt thereof;

1-[5-(3-Fluoropropoxy)pyridin-3-yl]-4-methyl-8-(morpholin-4-ylmethyl)[1,2,4]triazolo[4,3-a] quinoxaline;

1-[5-(3-Methoxypropyl)pyridin-3-yl]-4-methyl-8-(morpholin-4-ylmethyl)[1,2,4]triazolo[4,3-a]quinoxaline or a hydrochloride salt thereof; and 1-(5-Butoxy-6-chloropyridin-3-yl)-4-methyl-8-(morpholin-4-ylmethyl)[1,2,4]triazolo[4,3-a]quinoxaline;

and the stereochemically isomeric forms thereof, the pharmaceutically acceptable salts thereof.

2. A pharmaceutical composition comprising a therapeutically effective amount of a compound according to claim 1 and a pharmaceutically acceptable carrier.

* * * * *